United States Patent
Neilan et al.

(10) Patent No.: US 9,115,359 B2
(45) Date of Patent: Aug. 25, 2015

(54) METHODS FOR PRODUCING SECONDARY METABOLITES

(75) Inventors: Brett A. Neilan, Maroubra (AU); Alex Roberts, Dubbo (AU); Janine Copp, Nelson (NZ)

(73) Assignee: NewSouth Innovations Pty Limited, New South Wales (AU)

( * ) Notice: Subject to any disclaimer, the term of this patent is extended or adjusted under 35 U.S.C. 154(b) by 889 days.

(21) Appl. No.: 12/593,932

(22) PCT Filed: Apr. 2, 2008

(86) PCT No.: PCT/AU2008/000474
§ 371 (c)(1),
(2), (4) Date: Jun. 21, 2010

(87) PCT Pub. No.: WO2008/119134
PCT Pub. Date: Oct. 9, 2008

(65) Prior Publication Data
US 2010/0261218 A1 Oct. 14, 2010

(30) Foreign Application Priority Data

Apr. 2, 2007 (AU) ................................ 2007901738

(51) Int. Cl.
| C12P 7/64 | (2006.01) |
| C12Q 1/02 | (2006.01) |
| C12P 21/06 | (2006.01) |
| C12N 9/12 | (2006.01) |
| C07H 21/04 | (2006.01) |
| C12N 15/52 | (2006.01) |

(52) U.S. Cl.
CPC .............. C12N 15/52 (2013.01); C12N 9/1288 (2013.01)

(58) Field of Classification Search
CPC ........ C12N 15/52; C12N 9/1288; C12N 9/16; C12N 9/14; C12N 15/8247; C12N 15/67; C12N 15/74; C12N 1/26; C12N 5/0693; C12Q 1/48; C12Q 1/18
See application file for complete search history.

(56) References Cited

U.S. PATENT DOCUMENTS

| 4,356,270 | A | 10/1982 | Itakura ............................ 435/317 |
| 5,098,837 | A | 3/1992 | Beckmann et al. ......... 435/172.3 |
| 5,272,474 | A | 12/1993 | Hilliard ..................... 340/825.08 |
| 5,744,350 | A | 4/1998 | Vinci et al. ................ 435/254.11 |
| 6,251,636 | B1 | 6/2001 | Betlach et al. ................... 435/76 |
| 6,303,342 | B1 | 10/2001 | Julien et al. ...................... 435/76 |
| 2003/0073205 | A1* | 4/2003 | Arslanian et al. .............. 435/117 |
| 2005/0191679 | A1 | 9/2005 | Metz et al. ......................... 435/6 |
| 2011/0165633 | A1 | 7/2011 | Gregory et al. ................ 435/119 |

FOREIGN PATENT DOCUMENTS

| EP | 0 791 656 | A2 | 8/1997 |
| EP | 1 792 981 | A1 | 6/2007 |
| WO | WO 93/13663 | A1 | 7/1993 |
| WO | WO 01/27284 | A2 | 4/2001 |
| WO | WO 2006/093411 | A1 | 9/2006 |
| WO | WO 2006/124999 | A2 | 11/2006 |

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36)11643-50.*
Agrawal et al. An AU-box motif upstream of the SD sequence of light-dependent psbA transcripts confers mRNA instability in darkness in cyanobacteria, Nucl. Acids Res. (2001) 29 (9): 1835-1843.*
Accession No. AAW67221, "putative phosphopantetheinyl transferase [Nodularia spumigena NSOR10]," dated Apr. 27, 2006, retrieved from http://www.ncbi.nlm.nih.gov/protein/AAW67221, 1 page.
Accession No. AAY42632, "NhcS [Nodularia spumigena]," dated Nov. 16, 2006, retrieved from http://www.ncbi.nlm.nih.gov/protein/AAY42632, 1 page.
Accession No. BAA10326, "lipopeptide antibiotics iturin a biosynthesis protein [Synechocystis sp. PCC 6803]," dated Dec. 22, 2010, retrieved from http://www.ncbi.nlm.nih.gov/protein/BAA10326, 1 page.
Accession No. NP_442256, "lipopeptide antibiotics iturin a biosynthesis protein [Synechocystis sp. PCC 6803]," dated Nov. 3, 2011, retrieved from http://www.ncbi.nlm.nih.gov/protein/NP442256, 2 pages.
Baker et al., "Monitoring Changing Toxigenicity of a Cyanobacterial Bloom by Molecular Methods," *Applied and Environmental Microbiology* 68(12):6070-6076, 2002.
Beaucage et al., "Deoxynucleoside Phosphoramidites—A New Class of Key Intermediates for Deoxypolynucleotide Synthesis," *Tetrahedron Letters* 22(20):1859-1862, 1981.
Black et al., "Analysis of a Het Mutation in *Anabaena* sp. Strain PCC 7120 Implicates a Secondary Metabolite in the Regulation of Heterocyst Spacing," *Journal of Bacteriology* 176(8):2282-2292, 1994.
Brown et al., "Chemical Synthesis and Cloning of a Tyrosine tRNA Gene," *Methods in Enzymology* 68:109-151, 1979.
Brutlag et al., "Improved sensitivity of biological sequence database searches," *Comp. Appl. Biosci.* 6(3):237-245, 1990.
Burja et al., "*Marine cyanobacteria*—a prolific source of natural products," *Tetrahedron* 57:9347-9377, 2001.

(Continued)

*Primary Examiner* — Iqbal H Chowdhury
(74) *Attorney, Agent, or Firm* — Seed IP Law Group PLLC

(57) ABSTRACT

The invention relates to methods for producing secondary metabolites using transformed *Synechocystis* sp. bacteria, and secondary metabolites produced by transformed *Synechocystis* sp. bacteria. The invention further relates to phosphopantetheinyl transferase enzymes.

19 Claims, 11 Drawing Sheets

(56) References Cited

OTHER PUBLICATIONS

Chang et al., "Biosynthetic Pathway and Gene Cluster Analysis of Curacin A, an Antitubulin Natural Product from the Tropical Marine Cyanobacterium *Lyngbya majuscule*," *J. Nat. Prod.* 67:1356-1367, 2004.

Christiansen et al., "Nonribosomal peptide synthetase genes occur in most cyanobacterial genera as evidenced by their distribution in axenic strains of the PCC," *Arch., Microbiol.* 176:452-458, 2001.

Copp, "Catalysed Activation of Cyanobacterial Biosynthetic Pathways by Phosphopantetheinyl Transferases," Thesis, School of Biotechnology and Biomolecular Sciences, Univeristy of New South Wales, Australia, Dec. 2005, 218 pages.

Copp et al., "The Phosphopantetheinyl Transferase Superfamily: Phylogenetic Analysis and Functional Implications in Cyanobacteria," *Applied and Environmental Microbiology* 72(4):2298-2305, 2006.

Copp et al., "Characterization of $PPT_{NS}$, a Cyanobacterial Phosphopantetheinyl Transferase from *Nodularia spumigena* NSOR10," *Journal of Bacteriology* 189(8):3133-3139, 2007.

Crosby et al., "Polyketide synthase acyl carrier proteins from *Streptomyces*: expression in *Escherichia coli*, purification and partial characterisation," *Biochimica et Biophysica Acta* 1251:32-42, 1995.

Dittmann et al., "Molecular biology of peptide and polyketide biosynthesis in cyanobacteria," *Appl. Microbiol. Biotechnol.* 57:467-473, 2001.

Eaton-Rye, "The Construction of Gene Knockouts in the Cyanobacterium *Synechocystis* sp. PCC 6803," *Methods in Molecular Biology* 274:309-324, 2004.

Edwards et al., "Lyngbyatoxin Biosynthesis: Sequence of Biosynthetic Gene Cluster and Identification of a Novel Aromatic Prenyltransferase," *J. Am. Chem. Soc.* 126:11432-11433, 2004.

Ehrenreich et al., "Distribution and Diversity of Natural Product Genes in Marine and Freshwater Cyanobacterial Cultures and Genomes," *Applied and Environmental Microbiology* 71(11):7401-7413, 2005.

Elovson et al., "Acyl Carrier Protein—X. Acyl Carrier Protein Synthetase," *The Journal of Biological Chemistry* 243(13):3603-3611, 1968.

Extended European Search Report, for European Application No. 08733308.4, dated Dec. 8, 2010, 4 pages.

Fernandes et al., "Cloning, sequencing and characterization of a fatty acid synthase-encoding gene from *Mycobacterium tuberculosis* var. *bovis* BCG," *Gene* 170:95-99, 1996.

Finking et al., "Characterization of a New Type of Phsophopantetheinyl Transferase for Fatty Acid and Siderophore Synthesis in *Pseudomonas aeruginosa*," *The Journal of Biological Chemistry* 277(52):50293-50302, 2002.

Foerg et al., "Isolation of characterization of two sequence-specific endonucleases from the cyanobacterium *Synechocystis* sp. PCC 6308," *FEMS Microbiology Letters* 69:105-108, 1990.

Fortman et al., "Utilizing the Power of Microbial Genetics to Bridge the Gap Between the Promise and the Application of Marine Natural Products," *ChemBioChem* 6:960-978, 2005.

GenBank Accession No. AATP01000008, "*Fulvimarina pelagi* HTCC2506 1100011000312, whole genome shotgun sequence," dated Sep. 15, 2006, retrieved Nov. 28, 2011, from http://www.ncbi.nlm.nih.gov/nuccore/AATP01000008.1, 52 pages.

GenBank Accession No. AY646183, "*Nodularia spumigena* NSOR10 putative phosphopantetheinyl transferase (PPT) gene, complete cds," dated Apr. 27, 2006, retrieved Nov. 28, 2011, from http://www.ncbi.nlm.nih.gov/nuccore/AY646183, 1 page.

GenBank Accession No. AY836561, "*Nodularia spumigena* hetMNI biosynthetic gene locus, partial sequence," dated Nov. 16, 2006, retrieved Nov. 28, 2011, from http://www.ncbi.nlm.nih.gov/nuccore/AY836561, 2 pages.

GenBank Accession No. CP000843, "*Acaryochloris marina* MBIC11017 plasmid pREB6, complete sequence," dated Feb. 21, 2008, retrieved Nov. 28, 2011, from http://www.ncbi.nlm.nih.gov/nuccore/CP000843, 56 pages.

GenBank Accession No. CP000325, "*Mycobacterium ulcerans* Agy99, complete genome," dated Feb. 2, 2007, retrieved Nov. 28, 2011, from http://www.ncbi.nlm.nih.gov/nuccore/CP000325, 2 pages.

GenBank Accession No. CP000951, "*Synechococcus* sp. PCC 7002, complete genome," dated Mar. 14, 2008, retrieved Nov. 28, 2011, from http://www.ncbi.nlm.nih.gov/nuccore/CP000951, 1 page.

GenBank Accession No. NC_000962, "*Mycobacterium tuberculosis* H37Rv, complete genome," dated Sep. 16, 2011, retrieved Nov. 28, 2011, from http://www.ncbi.nlm.nih.gov/nuccore/NC_000962, 2 pages.

GenBank Accession No. NC_003155, "*Streptomyces avermitilis* MA-4680, complete genome," dated Aug. 29, 2011, retrieved Nov. 28, 2011, from http://www.ncbi.nlm.nih.gov/nuccore/NC_003155, 1 page.

GenBank Accession No. NC_003450, "*Corynebacterium glutamicum* ATCC 13032, complete genome," dated Nov. 21, 2011, retrieved Nov. 28, 2011, from http://www.ncbi.nlm.nih.gov/nuccore/NC_003450, 2 pages.

GenBank Accession No. NC_003888, "*Streptomyces coelicolor* A3(2) chromosome, complete genome," dated Nov. 3, 2011, retrieved Nov. 28, 2011, from http://www.ncbi.nlm.nih.gov/nuccore/NC_003888, 2 pages.

GenBank Accession No. NC_008611, "*Mycobacterium ulcerans* Agy99, complete genome," dated Feb. 14, 2011, retrieved Nov. 28, 2011, from http://www.ncbi.nlm.nih.gov/nuccore/NC_008611, 2 pages.

GenBank Accession No. NC_009725, "*Bacillus amyloliquefaciens* FZB42, complete genome," dated Nov. 12, 2011, retrieved Nov. 28, 2011, from http://www.ncbi.nlm.nih.gov/nuccore/NC_009725, 1 page.

GenBank Accession No. NC_010162, "*Sorangium cellulosum* 'So ce 56', complete genome," dated Oct. 28, 2011, retrieved Nov. 28, 2011, from http://www.ncbi.nlm.nih.gov/nuccore/NC_010162, 2 pages.

GenBank Accession No. NC_010184, "*Bacillus weihenstephanensis* KBAB4 chromosome, complete genome," dated Nov. 10, 2011, retrieved Nov. 28, 2011, from http://www.ncbi.nlm.nih.gov/nuccore/NC_010184, 2 pages.

GenBank Accession No. NZ_AAN001000000, "*Synechococcus* sp. WH 5701, whole genome shotgun sequencing project," dated Jun. 8, 2010, retrieved Nov. 28, 2011, from http://www.ncbi.nlm.nih.gov/nuccore/NZ_AANO00000000, 1 page.

GenBank Accession No. NZ_AAVW01000000, "*Nodularia spumigena* CCY 9414, whole genome shotgun sequencing project," dated Feb. 3, 2010, retrieved Nov. 28, 2011, from http://www.ncbi.nlm.nih.gov/nuccore/NZ_AAVW00000000, 1 page.

GenBank Accession No. X65866, "*Aspergillus nidulans* wA gene for polyketide synthase," dated Nov. 14, 2006, retrieved Nov. 28, 2011, from http://www.ncbi.nlm.nih.gov/nuccore/X65866, 4 pages.

Hoffmann et al., "Sequence analysis and biochemical characterization of the nostopeptolide A biosynthetic gene cluster from *Nostoc* sp. GSV224," *Gene* 311:171-180, 2003.

Hopwood et al., "Molecular Genetics of Polyketides and its Comparison to Fatty Acid Biosynthesis," *Annu. Rev. Genet.* 24:37-66, 1990.

International Preliminary Report of Patentability, for International Application No. PCT/AU2008/000474, dated Sep. 1, 2009, 7 pages.

International Search Report, for International Application No. PCT/AU2008/000474, mailed Jul. 4, 2008, 5 pages.

Joshi et al., "Cloning, Expression, and Characterization of a Human 4'—Phosphopantetheinyl Transferase with Broad Substrate Specificity," *The Journal of Biological Chemistry* 278(35):33142-33149, 2003.

Kaneko et al., "Sequence Analysis of the Genome of the Unicellular Cyanobacterium *Synechocystis* sp. strain PCC6803. I. Sequence Features in the 1 Mb Region from Map Positions 64% to 92% of the Genome," *DNA Research* 2:153-166, 1995.

Kealey et al., "Production of a polyketide natural product in nonpolyketide-producing prokaryotic and eukaryotic hosts," *Proc. Natl. Acad. Sci. USA* 95:505-509, 1998.

Koksharova et al., "Genetic tools for cyanobacteria," *Appl. Microbiol. Biotechnol.* 58:123-137, 2002.

(56) References Cited

OTHER PUBLICATIONS

Kotani et al., "Lessons from Sequencing of the Genome of a Unicellular Cyanobacterium, *Synechocystis* Sp. PCC6803," *Annu. Rev. Plant Physiol. Plant Mol. Biol.* 49:151-171, 1998.
Lambalot et al., "Cloning, Overproduction, and Characterization of the *Escherichia coli* Holo-acyl Carrier Protein Synthase," *The Journal of Biological Chemistry* 270(42):24658-24661, 1995.
Lambalot et al., "A new enzyme superfamily—the phosphopantetheinyl transferases," *Chemistry & Biology* 3:923-936, 1996.
Lee et al., "Tyrocidine Synthetase System," *Methods in Enzymology* 43:585-602, 1975.
Lee et al., "Population Dynamics and the Toxicity of Blue-Green Algae in the Naktong River, Korea," *Journal of Phycology* 37(Supplement 3):30, Abstract No. 76, 2001.
Li et al., "Expression of *hetN* during heterocyst differentiation and its inhibition of hetR up-regulation in the cyanobacterium *Anabaena* sp. PCC 7120," *FEBS Letters* 517:87-91, 2002.
Luesch et al., "The Cyanobacterial Origin of Potent Anticancer Agents Originally Isolated from Sea Hares," *Current Medicinal Chemistry* 9:1791-1806, 2002.
Magarvey et al., "Biosynthetic Characterization and Chemoenzymatic Assembly of the Cryptophycins. Potent Anticancer Agents from *Nostoc* Cyanobionts," *ACS Chemical Biology* 1(12):766-779, 2006.
Mayorga et al., "Isolation and Molecular Characterization of the *Aspergillus nidulans wA* Gene," *Genetics* 126:73-79, 1990.
McAllister et al., "Acyl Carrier Protein Synthases from Gram-Negative, Gram-Positive, and Atypical Bacterial Species: Biochemical and Structural Properties and Physiological Implications," *Journal of Bacteriology* 188(13):4737-4748, 2006.
McDaniel et al., "Genetic Approaches to Polyketide Antibiotics. 1," *Chem. Rev.* 105:543-558, 2005.
Moffitt et al., "Characterization of the Nodularin Synthetase Gene Cluster and Proposed Theory of the Evolution of Cyanobacterial Hepatotoxins," *Applied and Environmental Microbiology* 70(11):6353-6362, 2004.
Mofid et al., "Recognition of Hybrid Peptidyl Carrier Proteins/Acyl Carrier Proteins in Nonribosomal Peptide Synthetase Modules by the 4'-Phophopantetheinyl Transferases AcpS and Sfp," *The Journal of Biological Chemistry* 277(19):17023-17031, 2002.
Moore, "Cyclic peptides and depsipeptides from cyanobacteria: a review," *Journal of Industrial Microbiology* 16:134-143, 1996.
Nagle et al., "Chemical defense of a marine cyanobacterial bloom," *Journal of Experimental Marine Biology and Ecology* 225:29-38, 1998.
Namikoshi et al., "Bioactive compounds produced by cyanobacteria," *Journal of Industrial Microbiology* 17:373-384, 1996.
Narang et al., "Improved Phosphotriester Method for the Synthesis of Gene Fragments," *Methods in Enzymology* 68:90-98, 1979.
Needleman et al., "A General Method Applicable to the Search for Similarities in the Amino Acid Sequence of Two Proteins," *J. Mol. Biol.* 48:443-453, 1970.
Neilan et al., "16S Ribosomal RNA Gene Sequence and Phylogeny of Toxic *Microcystis* sp. (Cyanobacteria)," *DNA Sequence—The Journal of Sequencing and Mapping* 4:333-337, 1994.
Neilan et al., "Genetic Diversity and Phylogeny of Toxic Cyanobacteria Determined by DNA Polymorphisms within the Phycocyanin Locus," *Applied and Environmental Microbiology* 61(11):3875-3883, 1995.
Okino, "Heterocycles from Cyanobacteria," *Top Heterocycl. Chem.* 5:1-19, 2006.
Pfeifer et al., "Biosynthesis of Complex Polyketides in a Metabolically Engineered Strain of *E. coli*," *Science* 291:1790-1792, 2001.
Provasoli et al., "The Development of Artificial Media for Marine Algae," *Archiv Für Mikrobiologie* 25:392-428, 1957.
Qi et al., "Application of the *Synechococcus nirA* Promoter to Establish an Inducible Expression System for Engineering the *Synechocystis* Tocopherol Pathway," *Applied and Environmental Microbiology* 71(10):5678-5684, 2005.
Quadri et al., "Characterization of Sfp, a *Bacillus subtilis* Phosphopantetheinyl Transferase for Peptidyl Carrier Protein Domains in Peptide Synthetases," *Biochemistry* 37:1585-1595, 1998.
Reuter et al., "Crystal structure of the surfactin synthetase-activating enzyme Sfp: a prototype of the 4'-phosphopantetheinyl transferase superfamily," *The EMBO Journal* 18(23):6823-6831, 1999.
Sánchez et al., "Cloning and characterization of a phosphopantetheinyl transferase from *Streptomyces verticillus* ATCC15003, the producer of the hybrid peptide-polyketide antitumor drug bleomycin," *Chemistry & Biology* 8:725-738, 2001.
Schümann et al., "Advances in cloning, functional analysis and heterologous expression of fungal polyketide synthase genes," *Journal of Biotechnology* 124:690-703, 2006.
Simmons et al., "Marine natural products as anticancer drugs," *Molecular Cancer Therapeutics* 4(2):333-342, 2005.
Singh et al., "Bioactive Compounds from Cyanobacteria and Microalgae: An Overview," *Critical Reviews in Biotechnology* 25:73-95, 2005.
Smith et al., "Comparison of Biosequences," *Advances in Applied Mathematics* 2:482-489, 1981.
Supplementary European Search Report, for European Application No. 08 73 3308, dated Nov. 2, 2010, 2 pages.
Tillett et al., "Structural organization of microcystin biosynthesis in *Microcystis aeruginosa* PCC7806: an integrated peptide-polyketide synthetase system," *Chemistry & Biology* 7:753-764, 2000.
Walsh et al., "Polyketide and Nonribosomal Peptide Antibiotics: Modularity and Versatility," *Science* 303:1805-1810, 2004.
Wattanachaisaereekul et al., "Optimization of Heterologous Production of the Polyketide 6-MSA in *Saccharomyces cerevisiae*," *Biotechnology and Bioengineering* 97(4):893-900, 2007.
Weissman et al., "Identification of a Phosphopantetheinyl Transferase for Erythromycin Biosynthesis in *Saccharopolyspora erythraea*," *ChemBioChem* 5:116-125, 2004.
Wenzel et al., "Recent developments towards the heterologous expression of complex bacterial natural product biosynthetic pathways," *Current Opinion in Biotechnology* 16:594-606, 2005.
Williams, "Construction of Specific Mutations in Photosystem II Photosynthetic Reaction Center by Genetic Engineering Methods in *Synechocystis* 6803," *Methods in Enzymology* 167:766-778, 1988.
Yamamoto et al., "Importance of interspecific competition in the abundance of *Aphanizomenon flos-aquae* (Cyanophyceae)," *Limnology* 7:163-170, 2006.
Zhang et al., "Antiproliferative and Immunosuppressive Properties of Microcolin A, a Marine-Derived Lipopeptide," *Life Sciences* 60(10):751-762, 1997.

* cited by examiner

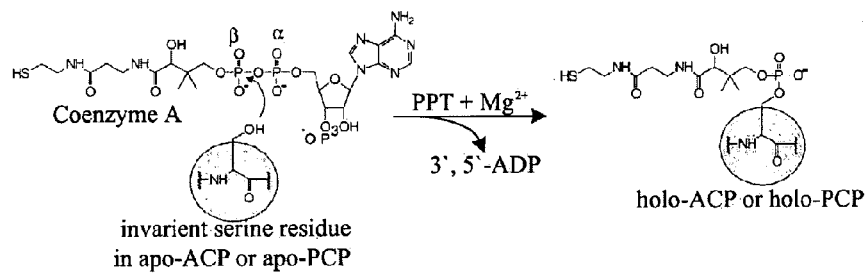

Figure 1

| Cyanobacterial species | Source of PPT sequence | Primers Utilised | Accession number | |
|---|---|---|---|---|
| Anabaena cylindrica. NEIS 19 | This study | PPTF/R | AY646191 | (SEQ ID NO: 50) |
| Anabaena variabilis ATCC29413 | Genome | N/a | ZP_00161864 | (SEQ ID NO: 51) |
| Croccosphaera watsonii WH8501 | Genome | N/a | ZP_00176116 | (SEQ ID NO: 52) |
| Cylindrospermum CENA 33 | This study | PPTF/R | AY646192 | (SEQ ID NO: 53) |
| Gleoebacter violaceus PCC7421 | Genome | N/a | BAC89892 | (SEQ ID NO: 54) |
| Gleoebacter violaceus PCC7421 | Genome | N/a | BAC92166 | (SEQ ID NO: 55) |
| Gleoebacter violaceus PCC7421 | Genome | N/a | BAC90792 | (SEQ ID NO: 56) |
| Nodularia harveyana UTEX-B2093 | This study | PPT2F/2R | AY646190 | (SEQ ID NO: 57) |
| Nodularia spumigena BY1 | This study | PPT2F/2R | AY646186 | (SEQ ID NO: 58) |
| Nodularia spumigena L575 | This study | PPT2F/2R | AY646189 | (SEQ ID NO: 59) |
| Nodularia spumigena NSBR01 | This study | PPT2F/2R | AY646184 | (SEQ ID NO: 60) |
| Nodularia spumigena NSLA01 | This study | PPT2F/2R | AY646187 | (SEQ ID NO: 61) |
| Nodularia spumigena NSLA02A4 | This study | PPT2F/2R | AY646188 | (SEQ ID NO: 62) |
| Nodularia spumigena NSOR10 | This study | PPT2F/2R | AY677619 | (SEQ ID NO: 63) |
| Nostoc piscale CENA 21 | This study | PPTF/R | AY646193 | (SEQ ID NO: 64) |
| Nostoc punctiforme ATCC29133 | Genome | N/a | ZP_00107102 | (SEQ ID NO: 65) |
| Nostoc punctiforme ATCC29133 | Genome | N/a | ZP_00110098 | (SEQ ID NO: 66) |
| Nostoc punctiforme ATCC29133 | Genome | N/a | ZP_00110892 | (SEQ ID NO: 67) |
| Nostoc sp. PCC7120 | Genome | N/a | P37695 | (SEQ ID NO: 68) |
| Prochlorococcus marinus CCMP1375 | Genome | N/a | AAP99138 | (SEQ ID NO: 69) |
| Prochlorococcus marinus CCMP1986 | Genome | N/a | CAE18537 | (SEQ ID NO: 70) |
| Prochlorococcus marinus MIT9313 | Genome | N/a | CAE21796 | (SEQ ID NO: 71) |
| Synechococcus elongatus PCC7942 | Genome | N/a | ZP_00164844 | (SEQ ID NO: 72) |
| Synechococcus PCC7002 | Genome | N/a | | |
| Synechococcus WH8102 | Genome | N/a | CAE08676 | (SEQ ID NO: 73) |
| Synechocystis PCC6803 | Genome | N/a | BAA10326 | (SEQ ID NO: 74) |
| Synechocystis PCC7008 | This study | PPTF/R | AY646194 | (SEQ ID NO: 75) |
| Thermosynechococcus elongatus BP1 | Genome | N/a | BAC09281 | (SEQ ID NO: 76) |
| Trichodesmium erytheaum IMS101 | Genome | N/a | | |

| Carrier protein (CP) | Expected mass (Da) | Observed apo-CP mass (Da) | Observed holo-CP mass (Da)* | % holo-CP (estimated)† |
|---|---|---|---|---|
| NpArCP glycolipid synthase | 15,751 | 15,749 | ND | 0% |
| MPCP microcystin NRPS | 21,978 | 21,978 | 22,319 | 8% |
| NpACP nostopeptolide PKS | 20,812 | 20,812 | 21,153 | 5% |
| TycPCP tyrocidine NRPS | 9,970 | 9,973 | 10,313 | 54% |

```
NhcS     1  MTALKRLNLPVPTNLTLLPNDVHIWRIHLDVPEAQQQNLLATLSGDELTRANRFHFQEHR
all5359     --MLQRTWLPKPPNLTLLSDVHLWRIPLDQPESQLQDLAATLSSDELARANRFYFPEHR
slr0495     -------MLPQE----------QRWLCPTDRP--LIPGYQALLSSEEKARGERYQRPQDK
Sfp         ------MCLSSNVN---QHNDTTVVVGTISSLHGRKESLVSYLSSDERQRAERMKSSVYA NhcS    61  QRFLAGRGILRSILGCYLGIPFQRVLEDTQERGKPILADSLAKSGLNFNLSHSQGLALCA
all5359     RRFTAGRGILRSLLGCYLGVPFQVVPDNESRGKPILGDRFAKSGLLFNLSHSQNLALCA
slr0495     QRFLTMRLALPILLARQHDCLPQLQFTYGPQGKPELVDRERRS-PWFNVAHSGNYGLIG
Sfp         ERRKLIRCYLPFLLSTVLALPRNQLHITYCKYGKPIVEN----NDYFFNVSHAKDYFLIG 2                                   3
NhcS   121  VNYENRICIDLEYIRRMSDYEALAKRFFLPREYDVVRSLSDHQQQEIFFRYWTCKEAYLK
all5359     VNYTRQIGIDLEYLRPTSDLESLAKRFFLPREYELLRSLPDEQKQKLFFRYWTCKEAVLK
slr0495     LSTEGEIGVDLQIMLPKPHYLKLAKRFFAPQEVQQLESLEGEKRTKLFYQLWTAKEAFLK
Sfp         LHETAVLGCDIRCPREFP---PKVHPFFYHQDEINLLASVDPDQKMRLWLSLWTRKEALGK NhcS   181  ATGEGLAQ-LEQVEYLLNFTEPAGLQTSESWSLFGLRA-------AEDYFAAVVVEGSGC
all5359     ATGEGIAK-LEKIELALTFTEPAKLQTAPAWSLLELVE-------DDNCVAAVAVAGFGW
slr0495     ATGKGISGGLNQVIPDEGLAKYQYLPDSGDTNHWRDSSQPADQGSNDNYWMAIAWCTNEV
Sfp         AVGEGLSS---NIGKQSVLSDTINYNGRREYVLETQHDE--------SVVKTICLEGKSV NhcS   233  NLQCMDY----------------          SEQ ID NO: 1
all5359     QPKFLNV----------------  (81%)  SEQ ID NO: 47
slr0495     NQVESNLLPNIQPFQWPRNLDSLP (58%)  SEQ ID NO: 48
Sfp         Q---------------------- (55%)  SEQ ID NO: 49
```

Figure 14

METHODS FOR PRODUCING SECONDARY METABOLITES

CROSS-REFERENCE TO RELATED APPLICATIONS

This application is a U.S. National Phase Application of International Application No. PCT/AU2008/000474, filed Apr. 2, 2008; which claims the benefit of Australian Patent Application No. 2007901738 filed Apr. 2, 2007. These applications are incorporated herein by reference in their entirety.

TECHNICAL FIELD

The invention relates to methods for producing secondary metabolites using transformed *Synechocystis* sp. bacteria, and secondary metabolites produced by transformed *Synechocystis* sp. bacteria. The invention further relates to phosphopantetheinyl transferase enzymes.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690159_401_USPC_SEQUENCE_LISTING.txt. The text file is approximately 13 KB, was created on Nov. 4, 2012, and is being submitted electronically via EFS-Web.

BACKGROUND

Non-ribosomal synthesis allows microorganisms to produce a diverse range of novel compounds including carboxy acids, heterocyclic rings, fatty acids and non-proteinogenic modified amino acids. Small polypeptides are assembled by peptide synthetases just as other compounds, like fatty acids, are linked by other synthetases during synthesis on the ribosome.

Non-ribosomal synthesis provides a pathway of synthesizing compounds which would be expensive or unobtainable using synthetic chemical methods. Nonribosomally synthesised peptides share certain characteristics. These small bioactive peptides are usually between 2 and 50 amino acid residues long and possess potent biological activities. Most examples of these compounds are also highly resistant to physical and chemical degradation making them ideal for use as oral therapeutics. The valuable products of microbial non-ribosomal peptide synthesis include the immunosuppressant cyclosporin A and antibiotics such as penicillin, gramicidin S, vancomycin, cephalosporin, and surfactins.

Such compounds are synthesized by complex secondary metabolism pathways involving polyketide synthases (PKS), non-ribosomal peptide synthetases (NRPS) and fatty acid synthases (FAS). These enzymes are activated by phosphopantetheinyl transferases (PPTs). PPTs activate carrier proteins that are essential for PKS, NRPS and FAS activity. PPTs convert inactive carrier proteins to their active, cofactor-bearing holo-forms via transfer of the essential prosthetic 4' phosphopantetheine moiety from co-enzyme A (CoA) (FIG. 1).

Cyanobacteria constitute a rich source of secondary metabolites with the majority being derived from PKS, NRPS and FAS. Due to their broad intergeneric distribution of integrated enzyme systems, cyanobacteria provide a source of many uncharacterised amino acid activating and modifying peptide synthetase modules. Consequently freshwater and marine cyanobacteria have been screened for bioactivity revealing natural products with novel biological applications and clearly implicating cyanobacteria as a rich source of potentially useful compounds.

Analysis of cyanobacterial non-ribosomal peptide, polyketide and fatty acid synthesis pathways has revealed unforeseen biochemical structures displaying the potential for novel products from cyanobacteria. However the strains of cyanobacteria which synthesize natural compounds are usually strains associated with slower growth or complicated culture requirements. Thus species which produce natural products may be excluded in culture-based screening. Furthermore current natural product screening relies on organism propagation. As less than 1% of microorganisms are estimated to be culturable, however, the bulk of potential bioactivities present in nature is not detectable. Alternatively, time-consuming organic syntheses have been used to create a modified natural product. Although molecular methods may yield the genetic information, recombinant expression in a suitable host organism is required to allow the isolation and production of novel compounds.

The ability to heterologously express and biochemically characterize recombinant proteins and biosynthesis pathways remains a significant problem with respect to cyanobacteria.

SUMMARY

The cyanobacterium *Synechocystis* sp. PCC6803 does not produce any secondary metabolites even though it possesses a PPT that could potentially allow the production of active carrier proteins. The *Synechocystis* PPT has broad substrate specificity and is capable of activating PKS, NRPS and FAS despite the fact that this species does not naturally encode either nonribosomal peptide or polyketide genes. This null background allows for the rapid identification of products potentially produced by heterologous expression in this species. This indicates the potential of *Synechocystis* as a suitable and efficient microorganism for the production of novel non-ribosomal peptides and polyketides.

According to a first aspect there is provided a method for the production of secondary metabolites, the method comprising the steps of transforming *Synechocystis* sp. bacteria with one or more of a peptide synthetase gene, a polyketide synthase gene, or a fatty acid synthase gene required for production of secondary metabolites, culturing the *Synechocystis* sp. bacteria under conditions suitable for the expression of the one or more genes required for production of the secondary metabolites, and purifying the secondary metabolites from the bacteria.

In one embodiment, the method further comprises prior to step (c), the step of screening the *Synechocystis* sp. bacteria for the production of secondary metabolites. In one embodiment, the screening step comprises high performance liquid chromatography or mass spectrometry.

In one embodiment, the *Synechocystis* sp. bacteria is *Synechocystis* sp. PCC6803. Preferably the secondary metabolite is a peptide, a polyketide, a fatty acid, or a derivative thereof. In one embodiment the peptide, polyketide, fatty acid or a derivative thereof is a bioactive compound selected from the group consisting of an anti-microbial agent, an anti-viral agent, an anti-fungal agent, an anti-cancer agent, an immunosuppressive agent, an anaesthetic, an analgesic, an antitumour product, an antibiotic, an anti-cholesterolemic, an anti-parasitic agent, a veterinary therapeutic agent, an agrochemical and a cosmetic.

In one embodiment, the one or more synthetase genes is operably linked to a promoter active in *Synechocystis* sp.

Preferably the promoter is an inducible promoter, such as a promoter inducible by varying the light intensity to which the bacteria are exposed during culture.

In one embodiment, the one or more synthetase genes is in a plasmid, phosmid or cosmid. In one embodiment, transformation of the *Synechocystis* sp bacteria is transposon-mediated. In one embodiment, the bacteria are transformed with multiple peptide synthetase, polyketide synthase, or fatty acid synthase genes forming a biosynthetic gene cluster.

In one embodiment, the *Synechocystis* sp. bacteria express an exogenous phosphopantetheinyl transferase (PPT). Preferably, the exogenous PPT is stably integrated into the *Synechocystis* sp. genome. Preferably, the exogenous PPT is a cyanobacterial PPT, such as a PPT from *Nodularia spumigena*. In one embodiment, the PPT is from *Nodularia spumigena* NSOR10. Preferably, the PPT comprises the amino acid sequence as set forth in SEQ ID NO: 1 or a variant of fragment thereof.

In another aspect there is provided a secondary metabolite produced in accordance with the method of the first aspect.

In another aspect, there is provided a transformed *Synechocystis* sp. bacteria comprising one or more of a peptide synthetase gene, a polyketide synthase gene, or a fatty acid synthase gene required for production of secondary metabolites.

In another aspect, there is provided use of *Synechocystis* sp. bacteria for the production of secondary metabolites, wherein the *Synechocystis* sp. are transformed with one or more of a peptide synthetase gene, a polyketide synthase gene or a fatty acid synthase gene required for production of secondary metabolites, and the *Synechocystis* sp. bacteria are cultured under conditions suitable for the expression of the one or more genes required for production of the secondary metabolites.

In one embodiment, the *Synechocystis* sp. bacteria is *Synechocystis* sp. PCC6803. In one embodiment the *Synechocystis* sp. bacteria express an exogenous PPT. In one embodiment the exogenous PPT is stably integrated into the *Synechocystis* sp. genome. In one embodiment, the exogenous PPT is a cyanobacterial PPT, such as a PPT from *Nodularia spumigena*. In one embodiment, the PPT is from *Nodularia spumigena* NSOR10. More preferably, the PPT comprises the amino acid sequence as set forth in SEQ ID NO: 1, or a variant of fragment thereof.

In another aspect, there is provided a phosphopantetheinyl transferase comprising the amino acid sequence set forth in SEQ ID NO: 1, or a variant or fragment thereof.

In another aspect, there is provided a phosphopantetheinyl transferase comprising the amino acid sequence set forth in SEQ ID NO: 2, or a variant or fragment thereof.

In one embodiment, the phosphopantetheinyl transferase encoded by the amino acid set forth in SEQ ID NO: 1 or SEQ ID NO: 2 or a functional variant of fragment thereof is provided in a vector. The vector may be provided in a host cell. The host cell may be a *Synechocystis* sp. host cell, such as *Synechocystis* sp. PCC6803.

Also provided are vectors comprising sequences of the invention, and host cells comprising the sequences and vectors of the invention. The invention also provides pharmaceutical compositions comprising at least one secondary metabolite prepared in accordance with the invention, together with a pharmaceutically acceptable carrier, excipient, adjuvant or vehicle.

BRIEF DESCRIPTION OF THE DRAWINGS

FIG. 1 is a diagram showing PPT activation of apo-carrier proteins. A PPT catalyzes the nucleophilic attack of the hydroxyl side chain of the conserved carrier protein serine residue on the 5'-β pyrophosphate linkage CoA. This causes the transfer of the phosphopantetheinyl moiety of CoA to the side chain of the conversed serine residue, converting the carrier protein from an inactive apo-form to an active holo-form (shown on the right of FIG. 1).

FIG. 2 is a table listing the source of cyanobacterial PPT sequences utilised by the inventors. Cyanobacterial PPTs were obtained from published database sequences (genome), or amplified from degenerate primers. N/a (not applicable)—refers to sequences obtained from online genome databases.

FIG. 3 shows a box shade amino acid sequence alignment of representatives of the "Sfp-like" PPT family. Black shading indicates identical residues while the grey shading indicates similar residues. Two subfamilies are shown. F/KES (top alignment) and W/KEA (lower alignment) sequences are separated and a consensus (cons) line is shown beneath. Sequences include; Pse, *Pseudomonas aeruginosa*, AAG04554; Xan, *Xanthomonas albicans*, AAG28384; Vib, *Vibrio cholerae*, AAD48884; Pho, *Photorhabdus luminescens*, AAK16071; Bac, *Bacillus subtilis*, P39135; Syn, *Synechocystis* PCC6803, BAA10326; Cae, *Caenorhabdus, elegans*, A89451; Dro, *Drosphilia melanogaster*, AAM12253. PPT motifs are boxed and numbered, including 1* as described. Numbering for Sfp from *Bacillus subtilis* is shown in brackets.

FIG. 5A shows colonies of *Synechocystis* sp. PCC6803 wildtype Sppt knockouts; FIG. 5B shows colonies of *Synechocystis* sp. PCC6803 wildtype chloramphenicol resistance plasmid positive control; FIG. 5C shows colonies of *N. punctiform* phosphopantetheinyl transferase complemented (ΔNsPPT$^+$) Sppt knockouts; FIG. 5D shows a ΔNsPPT$^+$ negative control which did not produce any colonies.

FIG. 9A shows the effect of pH on phosphopantetheinyl transferase activity as measured by HPLC assay. FIG. 9B shows the effect of CoA, the 4'-phosphopantetheinyl group donor, on Sppt activity.

FIG. 14 shows a boxshade amino acid alignment of PPT representative sequences. The NhcS PPT from *N. spumigena* NSOR10 was aligned with the all5359 from *Nostoc* sp. PCC7120 (P37695), slr0495 from *Synechocystis* sp. PCC 6803 (BAA10326) and Sfp from *B. subtilis* (P39135). NhcS numbering is shown and percentage similarity to NchS is displayed in brackets. PPT motifs are boxed and numbered.

FIG. 16A is a photograph of a gel showing of southern hybridisations of PPT probes to *N. spumigena* NSOR10. A "+" indicates a band was detected by chemiluminescence, the "−" indicates no bands were visible. Positive controls utilised linearised plasmid DNA. FIG. 16B is a table summarising the results of the southern hybrisation experiments. Bracketed numbering in the table shown in FIG. 16B corresponds to the lanes shown in the gel of FIG. 16A. Slr0495 refers to the PPT (BAA10326) from *Synechocystis* sp. PCC 6803, Nppt (ZP_00110892) refers to a PPT from *N. punctiforme* ATCC29133 and nchS is the PPT found in *N. spumigena* NSOR10.

FIG. 17A: mass spectrum of Arcp[1]. FIG. 17B: Mass spectrum of pantetheinylated Arcp after incubation with NhcS. FIG. 17C: mass spectrum of Mpcp[2]. FIG. 17D: mass spectrum of pantetheinylated Mpcp after incubation with NhcS. FIG. 17E: mass spectrum of Nppcp[3]. FIG. 17F: mass spectrum of pantetheinylated Nppcp after incubation with NhcS.

DEFINITIONS

Figure 4:
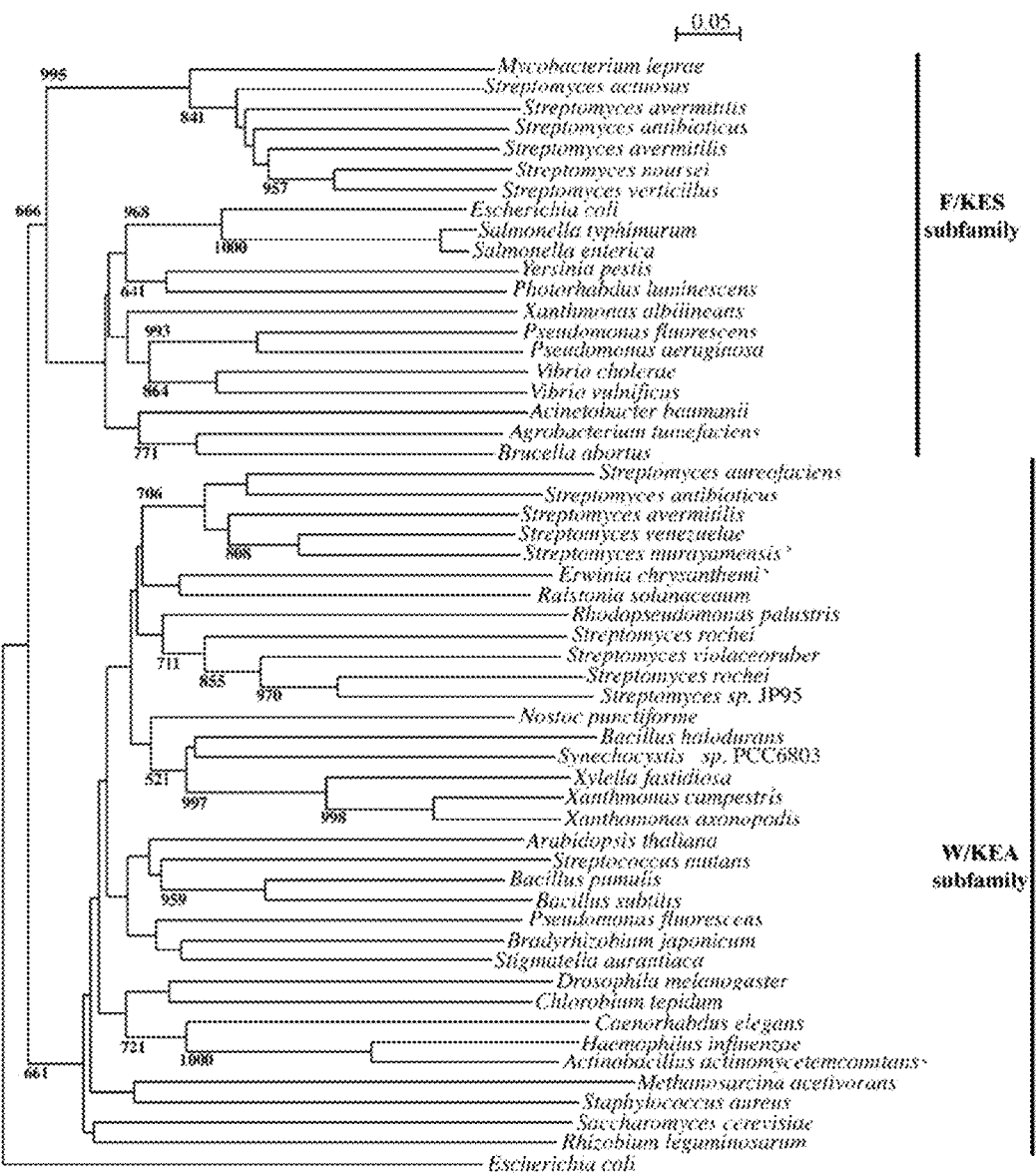
FIG. 4 is a phylogenetic tree diagram showing analysis of a selection of Sfp-like PPTs. The tree shows AcpS and Sfp-like PPT clades with accession numbers given in parenthesis. Significant bootstrap data (over 500 out of 1000 repeats) are displayed. *E. coli* AcpS was chosen as an outgroup for the Sfp-like PPT Glade. Two subgroups were observed and distinguished as the W/KEA and FACES clades respectively. Letters/symbols in superscript refer to PKS biosynthesis (P); NRPS biosynthesis (N); hybrid PKS/NRPS biosynthesis (H); siderophore biosynthesis (S); sequences obtained through the translation of contiguous sequences from unfinished genome projects (*); Sfp-like PPTs found in genomes without an AcpS (A–); cyanobacterial PPTs associated with heterocyst glycolipid synthesis (HET); and PPTs associated with lysine biosynthesis (L).

In the context of this specification, the term "comprising" means "including principally, but not necessarily solely". Furthermore, variations of the word "comprising", such as "comprise" and "comprises", have correspondingly varied meanings.

Throughout this specification, reference to "a" or "one" element does not exclude the plural, unless context determines otherwise. For instance, reference to "a nucleic acid construct" should not be read as excluding the possibility of multiple copies of such nucleic acid constructs.

The term "at least one" when used in the context of a group of selectable elements includes any and all members of the group individually selected and includes any combination of the members of the group. Similarly, the term "at least two" when used in the context of a group of selectable elements includes any selection of two or more members of the group in any combination.

As used herein, a "bioactive compound" is a compound which influences the biological structure, function, or activity of a cell or tissue of a living organism. A bioactive compound may, in general, elicit a biological response or effect or activity within the targeted end-user. For example, a bioactive compound may have a beneficial effect on the metabolism of a human, plant or animal, and/or provide therapeutic and/or cosmetic effects. Examples of bioactive compounds include, but are not limited to anti-viral agents, anti-fungal agents, anti-cancer agents, immunomodulatory agents, immunosuppressive agents, anaesthetics, analgesics, antitumour products, antibiotics, anti-cholesterolemics, anti-parasitic agents, veterinary therapies, agrochemicals, cosmetic agents, polynucleotides, proteins, peptides, polysaccharides, hormones, drugs, vitamins, steroids, anti oxidants, anti-inflammatory agents, moisturizers, carotenoids, UV absorbing agents, UV protecting agents and the like.

To the extent that it is permitted, all references cited herein are incorporated by reference in their entirety.

DETAILED DESCRIPTION OF THE PREFERRED EMBODIMENTS

The invention relates to methods for producing secondary metabolites, and in some embodiments to secondary metabolites produced by the methods of the invention. Despite having a null background and not naturally encoding either non-ribosomal peptide synthetase or polyketide synthase genes, cyanobacteria *Synechocystis* sp. can produce secondary metabolites when transformed with a peptide synthetase, polyketide synthase and/or fatty acid synthase gene. Consequently *Synechocystis* sp. provides excellent potential as a heterologous host in which to produce secondary metabolites.

In one aspect, there is provided a method for the production of secondary metabolites, the method comprising transforming *Synechocystis* sp. bacteria with one or more of a peptide synthetase gene, a polyketide synthase gene or a fatty acid synthase gene required for production of secondary metabolites, culturing the *Synechocystis* sp. bacteria under conditions suitable for the expression of the one or more genes required for production of the secondary metabolites and purifying the secondary metabolites from the bacteria. The peptide synthetase gene may be a non-ribosomal peptide synthetase gene.

The *Synechocystis* sp. bacteria may be selected from any suitable species or strain, or derivative thereof. For example, the *Synechocystis* sp. bacteria may be strains PCC6301, 6307, 6701, 6906, 7008, or 9632 (see *Archives of Microbiology*, Christiansen et al. 2001). In a particular embodiment, the *Synechocystis* sp. is PCC6803 (Pasteur Culture Collection, Paris). It is envisaged that the method may be suitable for production of any secondary metabolites such as a peptide or polyketide, fatty acid or a derivative thereof. The peptide may be a non-ribosomal peptide. The secondary metabolites may further comprise an anti-microbial agent, an anti-viral agent, an anti-fungal agent, an anti-cancer agent, an immunosuppressive agent, an anaesthetic or an analgesic, antitumour products, antibiotics, anti-cholesterolemics, anti-parasitic agents, veterinary therapies and agrochemicals and cosmetics. Specific examples of such agents include, but are not limited to vancomycin, microcystin, nodularin, saxitoxin, cyclosporin, and penicillin. The *Synechocystis* sp. bacteria may be selected from any suitable species or strain, or derivative thereof. For example, the *Synechocystis* sp. bacteria may be strains PCC6301, 6307, 6701, 6906, 7008, or 9632 (see *Archives of Microbiology*, Christiansen et al. 2001). In a particular embodiment, the *Synechocystis* sp. is PCC6803 (Pasteur Culture Collection, Paris). It is envisaged that the method may be suitable for production of any secondary metabolites such as a peptide, polyketide, fatty acid or derivatives or combinations thereof. The peptide may be a non-ribosomal peptide. The secondary metabolites may further comprise an anti-microbial agent, an anti-viral agent, an anti-fungal agent, an anti-cancer agent, an immunosuppressive agent, an anaesthetic or an analgesic, antitumour products, antibiotics, anti-cholesterolemics, anti-parasitic agents, veterinary therapies and agrochemicals and cosmetics. Specific examples of such agents include, but are not limited to vancomycin, microcystin, nodularin, saxitoxin, cyclosporin, and penicillin.

The peptide synthetase gene, polyketide synthase gene and/or fatty acid synthase gene used to transform *Synechocystis* sp. bacteria may be derived from any suitable source. For example, peptide synthetase, polyketide synthase and fatty acid synthase genes may be derived from various other bacteria and/or fungi. Examples of potential organisms from which the genes may be derived include, but are not limited to microalgae such as rhodophytes, chlorphytes, chromophytes and cyanobacteria (e.g. Chroocales, Chamaesiphonales, Nostcales, Nostocacaea, Rivulariaceae, Scytonemataceae, Stigonematales), *Streptomyces, Bacillus*, and various marine bacteria including as well as microbial symbionts of animals and plants.

By way of a non-limiting example only, suitable nucleotide sequences of peptide synthetase, polyketide synthase and/or fatty acid synthase genes and their corresponding protein sequences may be obtained from a cyanobacterial source, such as *Sorangium cellulosum* (obtainable through GenBank accession number NC_010162), *Acaryochloris marina* MBIC11017 (obtainable through GenBank accession number CP000843), *Synechoccus* sp. PCC 7002 (obtainable through GenBank accession number CP000951), *Nodularia spumigena* CCY 9414 (obtainable through GenBank accession number NZ_AAVW00000000), *Fulvimarina pelagi* HTCC2506 (obtainable through GenBank accession number AATP01000000) and *Synechococcus* sp. WH 5701 (obtainable through GenBank accession number NZ_AANO00000000).

By way of an additional non-limiting example, suitable nucleotide sequences of peptide synthetase, polyketide synthase and/or fatty acid synthase genes and their corresponding protein sequences may be obtained from *Streptomycetaceae* such as *Mycobacterium ulcerans* Agy99 (obtainable through GenBank accession number NC_008611), *Streptomyces avermitilis* MA-4680 (obtainable through GenBank accession number NC_003155), *Mycobacterium ulcerans* Agy99 4680 (obtainable through GenBank accession number CP000325), *Mycobacterium tuberculosis* H3Rv (obtainable through GenBank accession number NC_000962) and *Streptomyces coelicolor* A3 (2) (obtainable through GenBank accession number NC_003888).

By way of a further non-limiting example, suitable nucleotide sequences of peptide synthetase, polyketide synthase and/or fatty acid synthase genes and their corresponding protein sequences may be obtained from *Bacillus* sp. such as *Bacillus weihenstephanensis* KBAB4 (obtainable through GenBank accession number NC_010184), *Bacillus amyloliquefaciens* FZB42 (obtainable through GenBank accession number NC_009725) and *Corynebacterium glutamicum* ATCC 13032 (obtainable through GenBank accession number NC_003450).

By way of a further non-limiting example, a suitable polyketide synthase gene or protein sequence may be derived from *Aspergillus niger* and/or *Aspergillus nidulans* (wA gene, Mayorga et. al., Genetics 126 (1990) 73-79 (obtainable through GenBank accession number X65866).

The skilled addressee will understand that each of the accession numbers stated herein incorporate by reference all sequences and accession numbers obtainable through the stated number, such as specifically identified nucleotide and protein sequences of peptide synthetase, polyketide synthase and/or fatty acid synthase genes.

The *Synechocystis* sp. bacteria may be transformed or transfected with one or more of a peptide synthetase gene, a polyketide synthase gene or a fatty acid synthase gene using any suitable method. Such methods are generally known in the art and are described in, for example, *Molecular Cloning: A Laboratory Manual* (Joseph Sambrook, David W Russell, 3$^{rd}$. Edition, Cold Spring Harbour Press 2001), *Current Protocols in Molecular Biology* (Ausubel F. M. et al. (Eds), John Wiley and Sons, Inc 2007), *Molecular Cloning* (Maniatis et al., Cold Spring Harbor Laboratory, Cold Spring Harbor, N.Y., 1982) and *Current Protocols in Microbiology* (Coico et al (Eds), John Wiley and Sons, Inc, 2007), the entire contents of which are incorporated herein by cross-reference.

In particular embodiments, the peptide synthetase, polyketide synthase or fatty acid synthase gene may be cloned into a vector. The vector may be a plasmid vector, a viral vector, a phosmid, a cosmid or any other suitable vehicle construct for the insertion of foreign sequences, their introduction into cells and the expression of the introduced sequences. The vector may be an expression vector comprising expression control and processing sequences such as a promoter, an enhancer, polyadenylation signals and transcription termination sequences.

The construct may also include a selectable marker, for example, an antibiotic-resistance gene such as chloramphenicol or tetracycline. Genetic material for insertion into the construct may be generated, for example, by performing polymerase chain reaction (PCR) assays on target DNA. The resulting nucleic acids may then be inserted into the construct, for example, by restriction-ligation reactions or by the TA cloning method.

Suitable methods for the introduction of vector constructs and other foreign nucleic to acid material into *Synechocystis* sp. bacteria are generally known in the art, and described, for example, in *Current Protocols in Molecular Biology*, Ausubel et al. (Eds), New York: John Wiley & Sons, 2007) and *Molecular Cloning: A Laboratory Manual*, (Sambrook et al. 3rd Ed., Cold Spring Harbor Laboratory Press, Cold Spring Harbor, N.Y., 2001). By way of example, *Synechocystis* sp. may be transformed by the "heat shock" method. Under this method the cells are chilled in the presence of divalent cations such as $Ca^{2+}$, which causes cell wall permeability. Cells are incubated on ice with the construct and briefly heat shocked (e.g. at 42° C. for 0.5-2 minutes) causing the vector construct to enter the cell. Alternatively, *Synechocystis* sp. may be transformed with the vector construct by electroporation, a method involving briefly shocking the cells with an electric field causing the cells to briefly develop holes through which the construct may enter the cell. Natural membrane-repair mechanisms rapidly close these holes after the shock.

The peptide synthetase, polyketide synthase or fatty acid synthase gene/s may be inserted into the *Synechocystis* sp. genome by means of one or more transposons, or other mobile elements. These have been shown to mobilise large DNA fragments up to 59 kb in size. Mobilisation of transposons is mediated by transposases, usually resulting in the insertion of the DNA into target sequences in the genome. Putative transposases have been found to be associated with several biosynthetic gene clusters such as the microcystin and nodularin biosynthesis gene clusters. The ability of transposons to mobilise large gene clusters provides a DNA transfer system suitable for the transfer engineered biosynthetic gene clusters into null hosts for the expression of secondary metabolites.

Following entry of the construct into the cell, the *Synechocystis* sp. bacteria may be cultured under conditions suitable to facilitate reproduction. Methods for the culture of bacteria are well known in the art and described in, for example, *Current Protocols in Microbiology*, (Coico, et al. (Eds), John Wiley & Sons, Inc., 2007). The culture may be performed in medium containing a substrate which facilitates the identification of transformed strains, for example, an antibiotic such as chloramphenicol, kanamycin or tetracycline.

Transformed *Synechocystis* sp. strains may be selected and propagated. For example, if the target vector contains one or more selectable markers, the transformed *Synechocystis* sp. bacterial cells may be identified by expression of the marker or markers. Using the example of a drug resistance gene such as a chloramphenicol resistance gene, *Synechocystis* sp. transformants that grow in the selection media containing chloramphenicol can be identified as transformants. In the case of *Synechocystis* sp. transformants expressing more than one selectable marker, double transformants may be identified by the ability to grow in the selection media containing multiple selection determinants.

For the purpose of exemplification only, a specific method that may be utilised to transform *Synechocystis* sp. bacteria is as follows. *Synechocystis* sp. bacteria may be transformed with a gene deletion construct comprising sequences that are homologous to *Synechocystis* DNA sequences flanking the peptide synthetase, polyketide synthase or fatty acid synthase gene/s of interest. DNA is added to a 0.1-0.5 ml volume of concentrated *Synechocystis* culture, followed by incubation for 1-6 hours and plating out. After 20-24 hours selective conditions can be applied. Colonies of transformants come up in about one week, and may then be restreaked on plates with increasingly higher concentration of the antibiotic for which a resistance marker has been introduced. If a pure mutant phenotype is required, all wild-type genome copies need to be replaced. Two factors are important to readily obtain segregation: (1) a gradual increase in antibiotic selection pressure, and (2) selection of growth conditions under which the mutant phenotype has a competitive advantage or is not very much impaired when compared with the wild type. A convenient and rapid method to screen for segregation of wild-type and mutant genotypes is to prepare DNA from propagated *Synechocystis* transformants and to amplify the region of the mutation by PCR.

It will be appreciated that in accordance with the methods disclosed herein, the *Synechocystis* sp. bacteria may be transformed with multiple peptide synthetase, polyketide synthase and/or fatty acid synthase genes, allowing the generation of a biosynthetic gene cluster in the transformed *Synechocystis* sp. bacterial host. The biosynthetic cluster may comprise a hybrid of one or more peptide synthetase, polyketide synthase and/or fatty acid synthase genes. The polyketide synthase gene of the cluster or hybrid may be a non-ribosomal polyketide synthase gene.

Regulation of the expression of the peptide synthetase, polyketide synthase and/or fatty acid synthase gene sequences may be achieved by the use of regulatory sequences. For example, an expression vector may be used comprising expression control and processing sequences such as a promoter, an enhancer, polyadenylation signals and transcription termination sequences. Promoters may include inducible promoters (where expression of a polynucleotide sequence operably linked to the promoter is induced by an analyte, cofactor, regulatory protein, etc.), repressible promoters (where expression of a polynucleotide sequence operably linked to the promoter is repressed by an analyte, cofactor, regulatory protein, etc.), and constitutive promoters. The regulatory sequence may be regulated by an external stimulus. For example, light-inducible promoters are particularly useful due to the photosynthetic nature of *Synechocystis* sp. bacteria. The present invention is not limited in this respect and various inducible promoters may be used as known to the person skilled in the art. Such promoters include promoters induced by low temperature and by the action of a chemical compound such as tryptophan-inducible promoters, salt-inducible promoters, nitrite-inducible promoters, tyrosine-inducible promoters, and arabinose-inducible promoters.

*Synechocystis* sp. bacteria transformed with one or more of a peptide synthetase gene, a polyketide synthase gene or fatty acid synthase gene may be screened for production of the secondary metabolites. The secondary metabolites may then be purified. Any suitable methods of screening or purification may be used, taking into account various factors such as structural, enzymatic, functional, size features of the desired secondary metabolite. Methods and assays suitable for screening of transformed *Synechocystis* sp. bacteria and the purification of secondary metabolites are known in the art, and are described, for example, in *Current Protocols in Protein Science*, Coligan et al., (Eds) John Wiley and Sons, Inc. 2007). The screening and purification step may comprise, for example, chromatography methods, accelerated solvent extraction, or mass spectrometry or a combination thereof. Chromatography methods may include, for example, reverse phase chromatography, normal phase chromatography, affinity chromatography, thin layer chromatography, counter current chromatography, ion exchange chromatography and reverse phase chromatography. Examples of other methods include precipitation with ammonium sulphate, PEG, antibodies and the like or by heat denaturation, followed by centrifugation, isoelectric focusing, gel electrophoresis, selective precipitation techniques, and combinations of those and other techniques.

Secondary metabolites produced in accordance with the methods described herein may also be genetically engineered to contain various affinity tags or carrier proteins that aid purification. For example, the use of histidine and protein tags engineered into an expression vector comprising a peptide synthetase gene, a polyketide synthase gene and/or a fatty acid synthase gene may facilitate purification by, for example metal-chelate chromatography (MCAC) under either native and denaturing conditions. The purification of secondary metabolites may also be "scaled-up" for large-scale production purposes.

By way of exemplification only, a sample of *Synechocystis* sp. bacteria transformed with one or more peptide synthetase, a polyketide synthase and/or fatty acid synthase genes may be chemically screened by analysis using LC/MS coupled to UV photodiode array detection. Separation is performed and UV spectra are recorded and molecular weight information is obtained by MS with thermospray, continuous-flow fast atom bombardment, atmospheric pressure chemical ionization or electrospray ionization. Fragment information is obtained by tandem MS/MS or multiple stage $MS^n$ experiments while LC/NMR is used for confirmation of compound identity. Purification may also be performed by other methods known in the art such as solid phase extraction.

The skilled addressee will appreciate that the methods described herein are not limited by the methods of screening or purification described above and that any other method may be used to identify and/or isolate secondary metabolites derived from the transformed *Synechocystis* sp. bacteria.

In accordance with the methods disclosed herein, the secondary metabolite may be any compound derived from expression of the one or more peptide synthetase, polyketide synthase or fatty acid synthase genes used for transformation of the *Synechocystis* sp. bacterial host. The genes may be expressed alone or in combination. The expression of one or more of the peptide synthetase, polyketide synthase or fatty acid synthase genes may be combined to produce a hybrid product. Non-limiting examples of the secondary metabolites that may be produced in accordance with the methods disclosed herein are described in the Dictionary of Natural Products (Chapman & Hall, John Buckingham, Chapman & Hall/CRC, England CRC Press 1994), the entire contents of which are incorporated herein by cross-reference.

In certain embodiments, the secondary metabolite is a bioactive compound. Accordingly, the methods disclosed herein encompass the production of secondary metabolites including peptides, polyketides, fatty acids and hybrids or derivatives thereof that are bioactive compounds. In general, a bioactive compound is a compound which influences the biological structure, function, or activity of a cell or tissue of a living organism. The inventors have identified that in some species of *Synechocystis* sp., for example PCC6803, the production of secondary metabolites may be improved further through the use of exogenous/heterologous PPT. Preferably, the exogenous PPT is stably integrated into the *Synechocystis* sp. bacterial genome. For example, as shown herein, the *Nodularia spumigena* PPT is capable of being engineered to act in each of fatty acid synthesis, heterocyst glycolipid synthesis and biosynthesis of secondary metabolites. The inventors have demonstrated that the *N. spumigena* PPT phosphopantetheinylates carrier proteins from the microcystin synthetase gene cluster in *M. aeruginosa* PCC7806 and the nostopeptolide biosynthesis gene cluster in *N. punctiforme*.

Other PPTs may be suitable for transformation into *Synechocystis* sp., bacterial hosts, examples of which are shown in but not limited to those PPTs provided in the figures herein.

Examples of secondary metabolites that may be produced by the methods disclosed herein include, but are not limited to amino acids, fatty acids, macrolides, amides and lipopeptides or hybrids or derivatives thereof.

Fatty acids that may be produced include, but are not limited to omega 3-polyunsaturated fatty acids such as eicosapentanoic acid (EPA).

Lipopeptides produced by the methods disclosed herein generally comprise one or more amino acid derived fragments linked to one or more fatty acid derived portions. The lipopeptide may be cyclic or linear. An example of a lipopeptide that may be produced is hapalosin, a compound which is known to reverse multi-drug resistance derived from P-glycoprotein. The lipopeptides may be cytotoxic, antitumour, antiviral, antibiotic, antimalarial, antimycotic, multi-drug resitance reversing, antifeedants, herbicides, immunosuppressive agents, improved metabolism, cholesterol lowering effects, antioxidant properties.

Other non-limiting examples of smetabolites that may be obtained in accordance with the methods disclosed herein include the antibiotic erythromycin, the immunosuppressant FK506, and the antitumor compound epothilone. See also PCT patent publication No. 93/13663 (erythromycin); U.S. Pat. No. 6,303,342 B1 (epothilone); U.S. Pat. No. 6,251,636 B1 (oleandolide); PCT publication WO 01/27284 A2 (megalomicin); U.S. Pat. No. 5,098,837 (tylosin); U.S. Pat. No. 5,272,474 (avermectin); U.S. Pat. No. 5,744,350 (triol polyketide); and European patent publication No. 791,656 (platenolide), each of which is entirely incorporated herein by cross-reference.

Other non-limiting examples of metabolites that may be produced in accordance with the methods disclosed herein include cyanovirin-N, borophycin, cryptophycin, docosahexaenoic acid, β-Carotene, phycobiliprotein, phycocyanin, polysaccharides and protease inhibitors (e.g. micropeptins, aerugenosins, microginins, anabaenopeptins and microverdins)

Secondary metabolites produced in accordance with the methods disclosed herein may possess synergistic activity.

The PPTs disclosed herein include, but are not limited to those comprising the polypeptides set forth SEQ ID NO: 1 or SEQ ID NO: 2, or a variant or fragment thereof. The skilled addressee will appreciate that sequence variations, including both natural variations and engineered variations, may be made to the PPT-encoding polypeptides. Accordingly it will be appreciated that the sequences disclosed herein, including for example the PPT sequences provided in SEQ ID NOS: 1 and 2, encompass variants and/or fragments thereof.

The term "variant" as used herein refers to a substantially similar sequence. Polynucleotide and polypeptide sequence variants may share at least 40%, 45%, 50%, 55%, 60%, 65%, 70%, 75%, 80%, 85%, 90%, 95%, 96%, 97%, 98% or 99% sequence identity with the reference sequence. In general, polypeptide sequence variants possess qualitative biological activity in common. Polynucleotide sequence variants generally encode polypeptides which generally possess qualitative biological activity in common. Also included within the meaning of the term "variant" are homologues of polynucleotides and polypeptides of the invention. A polynucleotide homologue is typically from a different bacterial species but sharing substantially the same function or biological activity as the corresponding polynucleotide disclosed herein. A polypeptide homologue is typically derived from a different species but sharing substantially the same function or biological activity as the corresponding polypeptide disclosed herein. For example, homologues of the polynucleotides and polypeptides disclosed herein include, but are not limited to those from different species of cyanobacteria.

Further, the term "variant" also includes analogues of the polypeptides disclosed herein. A polypeptide "analogue" is a polypeptide which is a derivative of a polypeptide disclosed herein, which derivative comprises addition, deletion, substitution of one or more amino acids, such that the polypeptide retains substantially the same function. The term "conservative amino acid substitution" refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

In general, the degree of sequence homology between the sequences of the invention and a "variant" can be determined conventionally using known computer programs include, including, but not limited to: CLUSTAL in the PC/Gene program (available from Intelligenetics, Mountain View, Calif.); the ALIGN program (Version 2.0) and GAP, BEST-FIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters.

The BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman to find the best segment of homology between two sequences (Advances in Applied Mathematics 2:482-489 (1981)). When using BESTFIT or any other sequence alignment program to determine the degree of homology between sequences, the parameters may be set such that the percentage of identity is calculated over the full length of the reference nucleotide sequence and that gaps in homology of up to 5% of the total number of nucleotides in the reference sequence are allowed.

GAP uses the algorithm described in Needleman and Wunsch (1970) J. Mol. Biol. 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP presents one member of the family of best alignments.

Another method for determining the best overall match between a query sequence and a subject sequence, also referred to as a global sequence alignment, can be determined using the FASTDB computer program based on the algorithm of Brutlag and colleagues (Comp. App. Biosci. 6:237-245 (1990)). In a sequence alignment the query and subject sequences are both DNA sequences. An RNA sequence can be compared by converting U's to T's. The result of said global sequence alignment is in percent identity.

Also within the scope of the invention are fragments of the polypeptides disclosed herein. A polypeptide "fragment" is a molecule that comprises a constituent or is a constituent of a polypeptide disclosed herein or a variant thereof. Typically a polypeptide fragment possesses qualitative biological activity in common with the polypeptide of which it is a constituent. The polypeptide fragment may be between about 5 to about 1000 amino acids in length, between about 5 to about 750 amino acids in length, between about 5 to about 500 amino acids in length, between about 5 to about 270 amino acids in length, between about 5 to about 250, between about 5 to about 200 amino acids in length, between about 5 to about 150 amino acids in length, between about 5 to about 100 amino acids in length, between about 5 to about 50 amino acids in length, or between about 5 to about 10 amino acids in length. The fragment may be derived from the full-length PPT or alternatively may be synthesised by some other means, for example chemical synthesis.

Fragments of the polynucleotide sequences set forth herein are also included within the scope of the invention. A polynucleotide "fragment" is a polynucleotide molecule that encodes a constituent or is a constituent of a polynucleotide of the invention or variant thereof. Fragments of a polynucleotide do not necessarily need to encode polypeptides which retain biological activity. The fragment may, for example, be useful as a hybridization probe or PCR primer. The term "primer" as used herein means a single-stranded oligonucleotide capable of acting as a point of initiation of template-directed DNA synthesis. An "oligonucleotide" is a single-stranded nucleic acid typically ranging in length from 2 to about 100 bases. The precise length of a primer will vary according to the particular application, but typically ranges from 15 to 30 nucleotides. A primer need not reflect the exact sequence of the template but must be sufficiently complementary to hybridize to the template. Polynucleotide fragments may be derived from a polynucleotide of the invention. Alternatively, polynucleotide fragments, primers and oligonucleotide probes may be synthesized by some other means, for example chemical synthesis methods (see for example Narang S. A. et al. (1979) Meth. Enzymol. 68:90; Brown, E. L. et al. (1979) Meth. Enzymol. 68:109; and U.S. Pat. No. 4,356,270), Beaucage S. L. et al. (1981) Tetrahedron Letters, 22:1859-1862).

The skilled addressee will understand that the sequences disclosed herein and variants and fragments thereof may be used to screen other organisms or nucleic acid samples for the presence of useful PPTs.

Despite the absolute requirement for PPTs in a wide range of important and fundamental biosynthetic pathways, these enzymes have remained elusive due to their low sequence identity and lack of proximity to their respective biosynthetic clusters. This has hampered many efforts to express polyketide and non-ribosomal peptide products in heterologous host systems, largely due to the inability of the intrinsic *E. coli* PPTs to activate foreign substrates. This difficulty is further complicated by the observation that cyanobacterial biosynthetic gene clusters do not predominantly encode co-localised PPTs. For example, the *Lyngbya majuscula* gene clusters encoding barbamide, lyngbyatoxin and curacin A do not encode the essential PPT required for their synthesis.

The prototype PPT for the activation of secondary metabolite gene clusters is from *Bacillus subtilis*, Sfp. This PPT is required for the activation of carrier proteins incorporated within the biosynthetic pathway responsible for the production of surfactin. Members of this family are approximately 230 amino acids in length and are often found associated with the biosynthetic pathway in which they act. They display a broad range of specificities and the relaxed specificity of this family has been harnessed and manipulated in diverse applications, such as Sfp catalysed phagemid display and Sfp-labelling of carrier proteins.

Sequence alignment and phylogenetic analyses reveals that the PPT from *Synechocystis* sp. PCC6803 is closely related to the broad range PPT Sfp, and despite the lack of complex secondary metabolite production in *Synechocystis* sp PCC6803, the intrinsic PPT was predicted to be able to activate the carrier proteins of such metabolic pathways. The activity of the heterologously expressed *Synechocystis* sp. PPT Slr0495 has now been shown via nanospray mass spectrometry to comprise an additional mass of 355 Da corresponding to the phosphopantetheinyl arm of CoA when transferred to an acyl carrier protein. Preliminary experiments have shown Slr0495 to activate *Bacillus subtilis* peptidyl carrier proteins from a nonribosomal peptide synthetase, and *Nostoc punctiforme* PCC73102 acyl carrier proteins from a polyketide synthase.

Modules in peptide synthetases are several hundred amino acids long with the corresponding genes comprising the largest open reading frames known. Each module within a peptide synthetase contains core sequences responsible for amino acid recognition, modification and chain elongation. These core sequences result in a significant diversity of molecules of peptide synthetase origin. Possible modifications include activation, acyladenylation, thioesterification, methylation and racemisation of individual amino acid precursors. In addition, the final peptide may be linear, branched, cyclised or may be integrated with a polyketide side chain. To date more than 300 modified amino acids, including L- and D-forms, have been characterised arising from thiotemplate peptide formation. It has been shown that the genes involved in producing these large enzyme complexes are also modular and contain domains responsible for substrate recognition and modification. These operons encoding peptide synthetases may be manipulated to produce new novel peptides as has been shown for the genetic engineering of polyketides.

Peptide synthetase genes are coupled to strong promoters such as the PpsbA promoter, in specially tailored vectors for high expression. The inventors have developed and used such vectors for the heterologous expression of pili genes. Constructs are designed such that expression may also be regulated by a specific external stimulus, such as light intensity. Using the natural DNA uptake trait (transformability) of *Synechocystis* sp. PCC6803, these genetic constructs are introduced into the genome via homologous recombination. As the efficiency of this process is dependent on DNA insert size, optimization experiments are carried out to develop a protocol to enable the integration of various sized gene clusters encoding different compounds, which can range from about 10 kb to about 40 kb. Insertion sites target pili genes, which are responsible for both transformability and motility in this cyanobacterium. Insertion of genetic constructs into these sites render the strain non-motile and/or non-transformable, which serve as an intrinsic 'reporter phenotype' in addition to antibiotic selection. PCR and northern hybridizations are used in order to confirm stable integrants. Downstream experiments optimize expression of the newly integrated genes. Alternative strategies include the utilisation of phosmid based expression vectors and transposon-based gene transfer.

Transposons and other mobile elements have been shown to mobilise large DNA fragments up to 59 kb in size. Mobilisation of transposons is mediated by transposases, usually resulting in the insertion of the DNA into target sequences in the genome. Putative transposases have been found to be associated with several biosynthetic gene clusters such as the microcystin and nodularin biosynthesis gene clusters. Utilising the ability of transposons to mobilise large gene clusters, a DNA transfer system is suitable for the transfer engineered biosynthetic gene clusters into null hosts for the expression of novel compounds. The ability of the transposases to mobilise gene clusters is determined via activity assays, such as mating-out conjugations. Cyanobacterial transposases found to be active may be used to optimise a DNA transfer system for the introduction of heterologous DNA into the *Synechocystis* host.

Also provided herein is the use of *Synechocystis* sp. bacteria for the production of secondary metabolites, wherein the *Synechocystis* sp. are transformed with one or more of a peptide synthetase, a polyketide synthase or a fatty acid synthase gene required for production of secondary metabolites, and the *Synechocystis* sp. bacteria are cultured under conditions suitable for the expression of the one or more genes required for production of the secondary metabolites.

The *Synechocystis* sp. bacteria may be transformed with multiple peptide synthetase, polyketide synthase and/or fatty acid synthase genes, allowing the generation of a biosynthetic gene cluster in the transformed *Synechocystis* sp. bacterial host. The biosynthetic cluster may comprise a hybrid of one or more peptide synthetase, polyketide synthase and/or fatty acid synthase genes. The polyketide synthase gene of the cluster or hybrid may be a non-ribosomal polyketide synthase gene.

The *Synechocystis* sp. bacteria may be *Synechocystis* sp. PCC6803. The *Synechocystis* sp. bacteria may also expresses an exogenous PPT, which may be stably integrated into the *Synechocystis* sp. genome. The exogenous PPT may be a cyanobacterial PPT, and may be derived from *Nodularia spumigena*. In one embodiment, the PPT is from *Nodularia spumigena* NSOR10.

It will be understood that the description relating to the methods of producing secondary metabolites with transformed *Synechocystis* sp. bacteria provided herein are similarly applicable to the use of *Synechocystis* sp. bacteria for the production of secondary metabolites.

The present invention also includes pharmaceutical compositions comprising at least one secondary metabolite produced according to the invention, together with a pharmaceutically acceptable carrier, excipient, adjuvant of vehicle.

In general, suitable compositions may be prepared according to methods which are known to those of ordinary skill in the art and accordingly may include a pharmaceutically acceptable carrier, diluent and/or adjuvant.

These compositions can be administered by standard routes. In general, the compositions may be administered by the parenteral (e.g., intravenous, intraspinal, subcutaneous or intramuscular), oral or topical route. More preferably administration is to by the parenteral route.

The carriers, diluents and adjuvants must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

In order that the invention may be more clearly understood preferred forms will be described with reference to the following examples. It will be understood that these examples are intended to be illustrative of and not limiting to the invention.

EXAMPLES

Example 1

Phylogenetic Analyses (1) Creation of the sfp-Like Database

Sequences were collected by word-based ENTREZ searches, using any combination of words relating to phosphopantetheinyl transferases, e.g., Acyl carrier protein synthetase, Sfp, pantetheine. The output data of BLAST (Basic Local Alignment Search Tool) PSI-protein searches were utilised to extend the sequence set, and identify sequences that were not recognised through word-based searches. Available (completed and partial) genomes from the National Centre for Biotechnology Information (NCBI), Joint Genome Institute (JGI) and Cyanobase (www.kazusa.or.jp/cyano/cyano.html) were subjected to multiple BLAST screens with a variety of known PPT sequences from different bacterial genera.

(2) Multiple Alignments and Phylogenetics

The sequences were aligned using a program pileup from GCG and the multiple-sequence alignment tool from CLUSTAL X. The Neighbour Joining (N-J) method of Saitou and Nei was used to generate trees in CLUSTAL X. The data sets were bootstrapped (1000 resampling events), and the resulting trees were visualised using NJ plot and Treeview X. Alignments were created for publication via boxshade.

(3) Extraction, Amplification and Sequencing

Cyanobacterial strains (FIG. 2) were obtained from the UNSW Cyanobacterial Culture Collection. Genomic DNA was extracted from cyanobacterial cultures as previously described (Neilan et al., *Applied and Environmental Microbiology* (1995) "*Genetic diversity and phylogeny of toxic cyanobacteria determined by DNA polymorphisms within the phycocyanin locus*" 61: 3875-83). Amplification of cyanobacterial PPT fragments was performed using the primers PPTF [5'-CAGGAGTAYGGNAARCC-3'] (SEQ ID NO: 3) and PPTR [5'-TTCTCGATRTCDATNCC-3' (SEQ ID NO: 4) that were specifically designed to correspond to motifs 3 and 4 respectively. Heterocyst PPT sequences were amplified utilising PPT2F [5'-GCCCGTGGTAAACAAATATTAG-3'] (SEQ ID NO: 5) and PPT2R [5-'GCCTCTTTACAAGTCCA-3'] (SEQ ID NO: 6). Thermal cycling was performed in a GeneAmp PCR 2400 thermocycler (Perkin Elmer, Norwalk, Conn.) as previously published (Neilan et al., *Applied and Environmental Microbiology* (1995), *Genetic diversity and phylogeny of toxic cyanobacteria determined by DNA polymorphisms within the phycocyanin locus.* 61:3875-83) with an annealing temperature of 45-55° C. depending on the primer pair utilized. Automated sequencing was performed using the PRISM Big Dye cycle sequencing system and a model 373 sequencer (Applied Biosystems Inc., USA). Sequence analysis was performed using Applied Biosystems Autoassembler software.

(4) Sequence Conservation within the Sfp-Like Family

Figure 3:
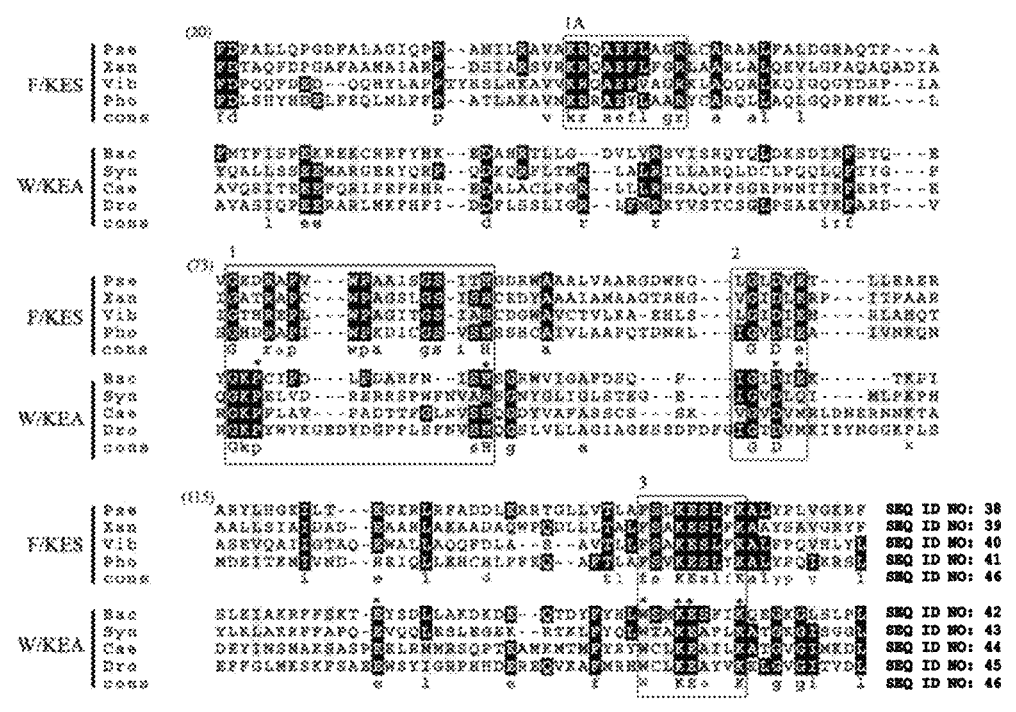

The resulting alignments reveal additional examples of sequences diverging from the amino acids considered critical for PPT function. For example, it is noted that $H^{90}$ from Motif 2, associated with binding the 3'-phosphate of CoA, is absent in several sequences including all *Methanosarcina*, some *Staphylococcus* sp., and a *Streptomyces* sp. An alignment of Sfp-like PPT representatives is shown in FIG. 3. Two distinct subfamilies were observed. Motif 4 of the first subfamily is depicted as F(S/C)KES (hereafter referred to as "the F/KES subfamily"). The second subfamily included the Sfp sequence from *B. subtilis*. This group displays the peptide sequence W(T/C)KEA as motif 4 (hereafter referred to as "the W/KEA subfamily").

(5) Phylogenetic Analysis

The phylogenetic trees presented show distinct, novel clades and support the subfamilies observed in alignment analyses. The Sfp-like PPT subfamilies were separated and supported by bootstrap data (FIG. 4). The AcpS PPT was utilized to serve as an outlier.

Representatives that harbour multiple Sfp-like PPTs were shown to have PPTs falling within both F/KES and W/KEA branches of the phylogeny, including *Streptomyces, Escherichia, Microbacterium, Pseudomonas, Xanthomonas,* and *Salmonella* (FIG. 4). Sfp-like PPTs from organisms without an AcpS-like PPT are also present in both clades. For example, *Pseudomonas aeruginosa* and *Haemophilus influenzae* (AAC21831) were observed in the F/KES and W/KEA subfamilies respectively. PPTs found in hybrid (PKS-NRPS) biosynthetic clusters are also represented in both subfamilies.

The F/KES subfamily encompassed the majority of PPTs associated with peptide synthetases and siderophore synthesis, including all enterobactin EntD enzymes and the subset of *Streptomyces* PPTs described in Weissman et al., (2004) *Identification of a phosphopantetheinyl transferase for erythromycin biosynthesis in Saccharopolyspora erythraea*", *ChemBioChem* 5:116-25.

The second subfamily of W/KEA subgroup included the *B. subtilis* PPT Sfp. This phylotype included the diverse heterocyst glycolipid biosynthetic PPTs the lysine biosynthesis PPTs and invertebrate and eukaryotic PPT sequences. PPT enzymes involved in polyketide biosynthesis are predominant in the W/KEA group, such as MupN (AAM12928) associated with mupirocin production in *Pseudomonas fluorescens*.

Example 2

Gene Disruption of *Synechocystis* PPT (Sppt)

Sppt was insertionally inactivated to determine whether it was the only enzyme capable of phosphopantetheinylation in *Synechocystis* sp. PCC6803. Genomic DNA for PCR amplification was extracted as previously described (Moffitt, M. C. and B. A. Neilan. 2004. *Characterization of the nodularin synthetase gene cluster and proposed theory of the evolution of cyanobacterial hepatotoxins. Appl Environ Microbiol* 70:6353-62). All restriction enzymes were supplied by New England Biolabs (Ipswich, Mass.) or Promega (Madison, Wis.).

A 2.5 kb fragment including Sppt (slr0495, Swissprot accession number Q55185) was amplified with the primers sirup (5'-GTAAACTCCATTAACGCTGGC-3') (SEQ ID NO: 7) and slrdn (5'-GGTGCAAATCCGTTACATGGA-3') (SEQ ID NO: 8). This fragment was cloned into pGEM-T-Easy (Promega) and digested with the restriction enzyme AvaI. A chloramphenicol (Chl$^R$) resistance cassette was ligated into this site and the resulting plasmid, pGCSlr, was naturally transformed into *Synechocystis* sp. PCC6803 to insertionally inactivate Sppt using methods described in Eaton-Rye, J., 2004 *The construction of gene knockouts in the cyanobacterium Synechocystis* sp. PCC 6803, *Methods Mol. Biol.*; 274:309-24. The *Synechocystis* sp. PCC6803 wildtype (WT) was also transformed with a chloramphenicol resistance knockout plasmid as a positive control for strain viability. Briefly, approximately 2 ml *Synechocystis* sp. PCC6803 cells were centrifuged and washed in BG-11 media. After resuspension in 300 µA BG-11, 3 µg ml$^{-1}$ plasmid was added and the cells were incubated at 25° C. in 30 µmol m$^{-2}$ sec$^{-1}$ constant light for 6 hours. The cells were spread onto sterile nitrocellulose filters (0.45 µm, Millipore, Billerica Mass.) on non-selective BGTS plates (BG-11, 10 mM TES, 0.3% sodium thiosulfate, 1% agar). After 36 hours, the filters were transferred to selective BGTS plates with 10 µg ml$^{-1}$ chloramphenicol.

Figure 5:
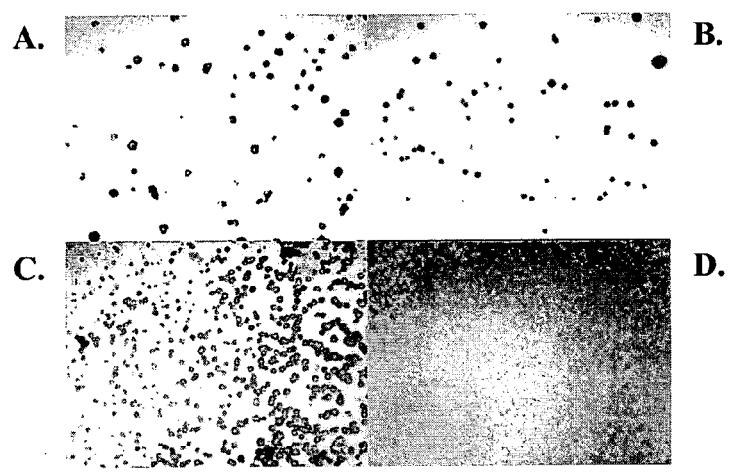
FIG. 5 is a photograph showing *Synechocystis* sp. PCC6803 Sppt knockout transformants on BGTS plates with chloramphenicol.
Figure 6:
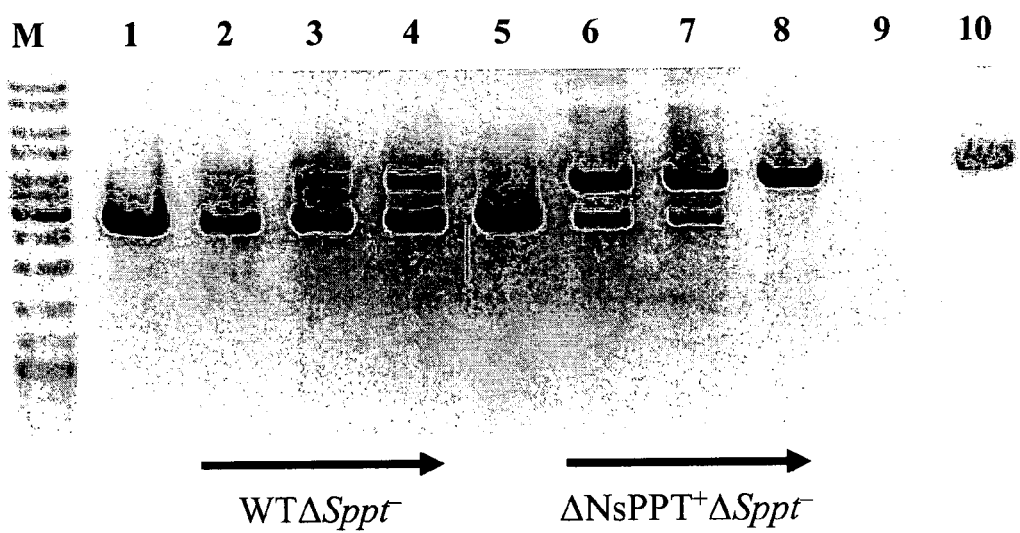
FIG. 6 is a photograph of a gel used for electrophoresis of PCR screening products of Sppt disrupted and NsPPT-complemented *Synechocystis* sp. PCC6803 strains. Lane M, molecular weight marker; Lane 1, *Synechocystis* sp. PCC6803 WT Sppt gene; Lanes 2-4, *Synechocystis* sp. PCC6803 wildtype (WT) Sppt knockout heterozygous mutant with repeated subculturing on selective media; Lane 5, ΔNsPPT$^+$ complemented Sppt gene; Lanes 6-7, ΔNsPPT$^+$ complemented Sppt heterozygous mutant with repeated subculturing on selective media; Lane 8, ΔNsPPT$^+$ fully segregated Sppt knockout mutant; Lane 9, negative PCR control; Lane 10, knockout plasmid, pGCSlr, with chloramphenicol cassette inserted into Sppt gene. Arrows indicate segregation of Sppt into chromosomal copies of the genome with repeated subculturing.

Initial transformants were visible on selective chloramphenicol plates and were subcultured repeatedly under increasing selection (FIG. 5A). However, PCR screening of these transformants revealed that the insertionally inactivated Sppt gene could not completely segregate throughout the multiple genome copies (FIG. 6, lane 4). In contrast, Sppt was effectively disrupted in the NsPPT-complemented strain (ΔNsPPT$^+$), (FIG. 6, lane 8). Transformation of the ΔNsPPT$^+$ strain with ddH$_2$O showed that this strain was not resistant to chloramphenicol before gene disruption with pGCSlr (FIG. 5D).

The lack of complete segregation of Sppt throughout the multiple chromosomes suggests that Sppt is essential for phosphopantetheinylation in fatty acid synthesis. Complementation with the broad range activity NsPPT from *Nodularia spumigena* NSOR10 allowed for the successful disruption of Sppt. This confirms Sppt is required for primary metabolism in *Synechocystis* sp. PCC6803. It also shows, for the first time, the ability of NsPPT to activate non-cognate carrier proteins in vivo.

Example 3

Expression and Purification of Sppt and SACP

Sppt and SACP were expressed and purified to determine the activity of Sppt via phosphopantetheinylation assays. Sppt was amplified by the primer pair SynPpF (5'-TGTT-TAAACTCACCTG-3') (SEQ ID NO: 9) and SynPpR (5'-CCCAAGGTTACGAAAC-3') (SEQ ID NO: 10). The resulting PCR product was cloned into pGEM-T (Promega), digested with the restriction enzymes SacI and EcoRV and ligated into pET30 (Novagen, San Diego, Calif.). The *Synechocystis* sp. PCC6803 fatty acid synthesis (FAS) ACP, designated SACP (AcpP BA000022), was amplified by the primer pair ssl2084Efw (5'-GGAATTCTGAATCAG-GAAATTT-3') (SEQ ID NO: 11) and ssl12084 Hry (5'-CTCGGCTCCAAAAAGCTTTGGG-3') (SEQ ID NO: 12), digested with the restriction enzymes EcoRI and HindIII, and cloned into pET30. A truncated SACP, SACP3, was cloned and expressed for HPLC kinetic analysis using the primers 2084NdeF (5'-GCATATGAATCAGGAAATTT-3') (SEQ ID NO: 13) and 2083XhoR (5'-CCTCGAGTAATTTACTTTC-GATATGCTCAAC-3') (SEQ ID NO: 14).

The constructs were transformed into BL21(DE3) Rosetta (Novagen) for expression. Sppt was expressed at 37° C., with an induction concentration of 1 mM isopropyl-beta-D-thiogalactopyranoside (IPTG), for 3 hours. SACP and SACP3 were expressed at 37° C. with 1 mM IPTG for 20-40 min. Cultures were harvested at 5,000×g and cell pellets were stored at −80° C. Cell pellets were resuspended in Hepes buffer (Hepes 50 mM, NaCl 150 mM pH 7.4) and passaged three times through a cooled French pressure cell at 200 psi (Paton Scientific, Victor Harbor, South Australia).

After centrifugation at 20,000×g for 30 min, proteins were purified using HiTrap affinity columns (Amersham Biosciences, Piscataway, N.J.) using a 300 mM imidazole gradient as previously described in Copp J. N., Roberts A. A., Marahiel M. A., Neilan B. A., 2007, *Characterization of PPTNs, a cyanobacterial phosphopantetheinyl transferase from Nodularia spumigena NSOR10. J. Bacteriol.*:189(8): 3133-9. Fractions containing the purified proteins were desalted with Amicon centrifuge columns (Millipore) and snap frozen with 8% glycerol for storage at −80° C.

The protein concentrations were determined based on the calculated extinction coefficients: SACP 6,970 cm$^{-1}$M$^{-1}$, Sppt 53,110 cm$^{-1}$M$^{-1}$. Due to the absence of aromatic amino acids in SACP3, the concentration of this protein was established using molecular imaging (FUJIFILM LAS-3000) compared to a standard curve of known BSA concentration.

Figure 8:
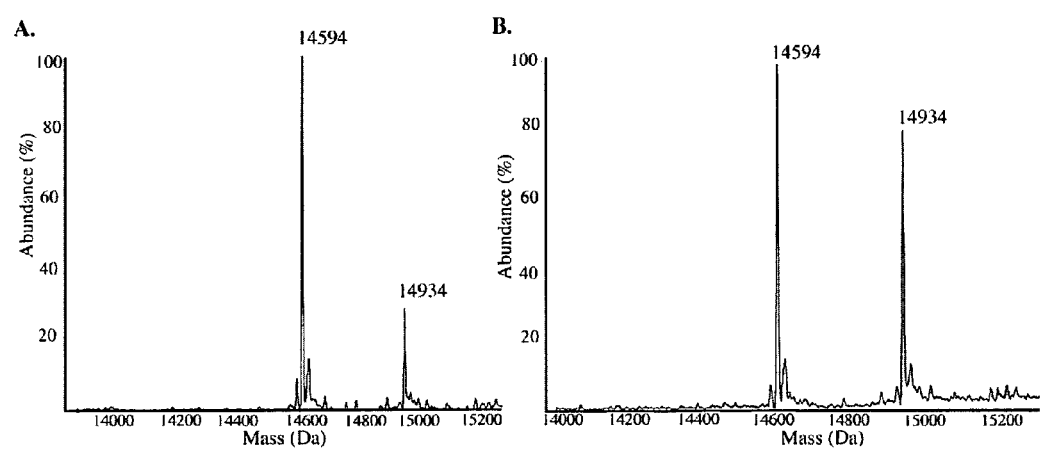
FIG. 8 shows mass spectra of SACP (FIG. 8A) and SACP after a phosphopantetheinylation assay with Sppt (FIG. 8B).

SACP was expressed and purified as an approximately 17 kDa protein, as determined by SDS-PAGE. However, mass spectrometry analysis revealed this protein to be 14.7 kDa, which corresponded to the theoretical mass. Unusual migration of ACPs, as visualised by SDS-PAGE, has been previously described in the expression of a *Streptomyces* sp. PKS ACP (Crosby et al. (9995) *Polyketide synthase acyl carrier proteins from Streptomyces: expression in Escherichia coli, purification and partial characterisation, Biochim Biophys Acta.* 16:32-42). Mass spectrometry analysis of purified SACP3 showed species present in the apo-, holo- and dimerised holo-form (data not shown). The appearance of phosphopantetheinylated SACP results from the partial conversion of apo- to holo-SACP by the intrinsic PPTs within the *E. coli* host. Phosphopantetheinylation activity of Sppt was confirmed with the further conversion of apo- to holo-SACP in a 10 min assay (FIG. 8B).

Example 4

Sppt in vitro Phosphopantetheinylation of SACP

Sppt activity towards SACP was determined in a 10 min phosphopantetheinylation assay at 37° C. as previously described in Copp J. N., Roberts A. A., Marahiel M. A., Neilan B. A., 2007, *Characterization of PPTNs, a cyanobacterial phosphopantetheinyl transferase from Nodularia spumigena NSOR10. J Bacteria* 189(8):3133-9. Briefly, the 100-200 µl reactions comprised of 50 mM Tris-HCl pH 7.4, 12.5 mM MgCl2, 0.5 mM CoA, 2 µM DTT, 100 µM carrier protein and 300 nM Sppt. Reactions were incubated for 10 min at 37° C., terminated by the addition of 1 ml trichloroacetic acid and precipitated overnight at −20° C. before centrifugation for 15 min at 18,000×g. Samples were dissolved in water:acetonitrile:formic acid (50:49:1). Phosphopantetheinylation was observed by an increase in mass of 340 Da as visualised by electrospray ionisation mass spectrometry (ESI-MS). Spectra were acquired using an API Qstar Pulsar i hybrid tandem mass spectrometer (Applied Biosystems) as previously described in Copp J. N., Roberts A. A., Marahiel M. A., Neilan B. A., 2007, *Characterization of PPTNs, a cyanobacterial phosphopantetheinyl transferase from Nodularia spumigena NSOR*10. *J Bacteriol.*: 189(8): 3133-9.

Figure 7:
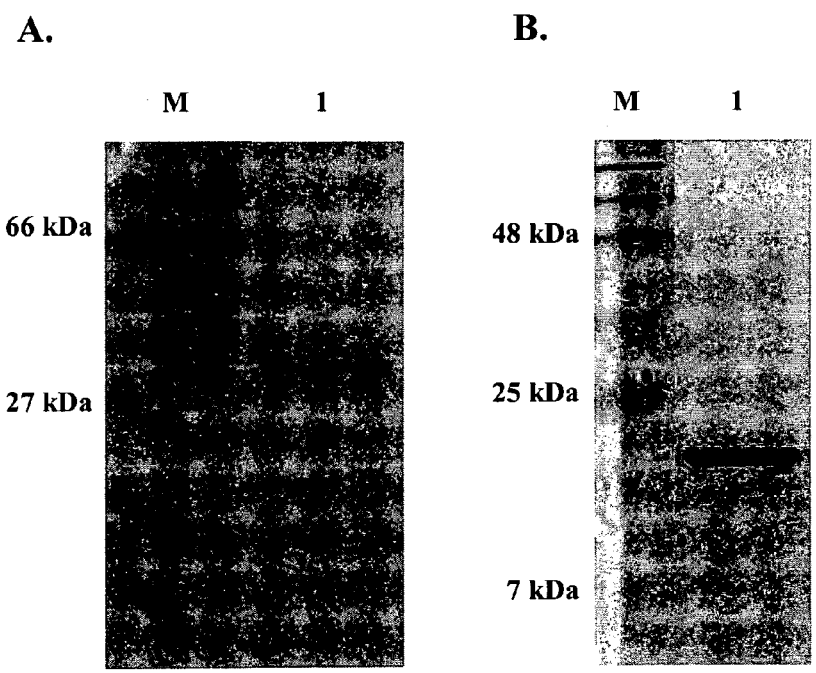
FIG. 7 is a photograph of an SDS-PAGE gel of purified *Synechocystis* sp. PCC8603 phosphopantetheinyl (sPPT) (FIG. 7A) and *Synechocystis* sp. PCC8603 fatty acid synthesis carrier protein (SACP) (FIG. 7B). M: Broadrange and Prestained Markers (New England Biolabs).

Although sodium dodecyl sulphate polyacrylamide gel electrophoresis (SDS-PAGE) analysis shows the purified SACP at an observed molecular weight of 17 kDa (FIG. 7), mass spectrometry revealed the purified protein to be 14.594 kDa (FIG. 8A), corresponding to a loss of the N-terminal methionine residue when compared to the theoretic mass of 14.73 kDa. The ratio of holo- to apo-carrier protein after heterologous expression in *E. coli* was analysed by mass spectrometry. SACP was partially phosphopantetheinylated after heterologous expression in *E. coli*, with a holo:apo ratio of 70:30. After in vitro incubation with Sppt, SACP showed an increased abundance of phosphopantetheinylated carrier protein, indicating that Sppt can activate the cognate SACP (FIG. 8B).

Example 5

Kinetic Analysis of Sppt Activity

The CoA inhibition and pH activity range for Sppt was determined using in vitro phosphopantetheinylation assays with the truncated SACP3. Assays were carried out as above in 200 µL reactions comprising of 75 mM MES (pH 5.5-6.5), Tris (pH 7-8.5) or CAPSO (pH 9-10) and 1-3 mM CoA. After precipitation, the pellets were resuspended in 30 µl 55% Solvent B (acetonitrile, 0.1% trifluoroacetic acid). An Alltech 5 µm Nucleosil C18 column (250×4.6 mm) was equilibrated with 55% Solvent B at 45° C. before sample injection. Samples were eluted with a linear gradient from 55% to 68% Solvent B over 15 min with 0.9 ml min$^{-1}$ flow rate. The absorbance at 200 nm was constantly monitored. The amount of holo-SACP3 formed was determined by comparative analysis of the holo-ACP peak area of control assays without PPT. Holo-SACP3 present after heterologous expression in *E. coli*, was subtracted from the total amount phosphopantetheinylated.

Figure 9:
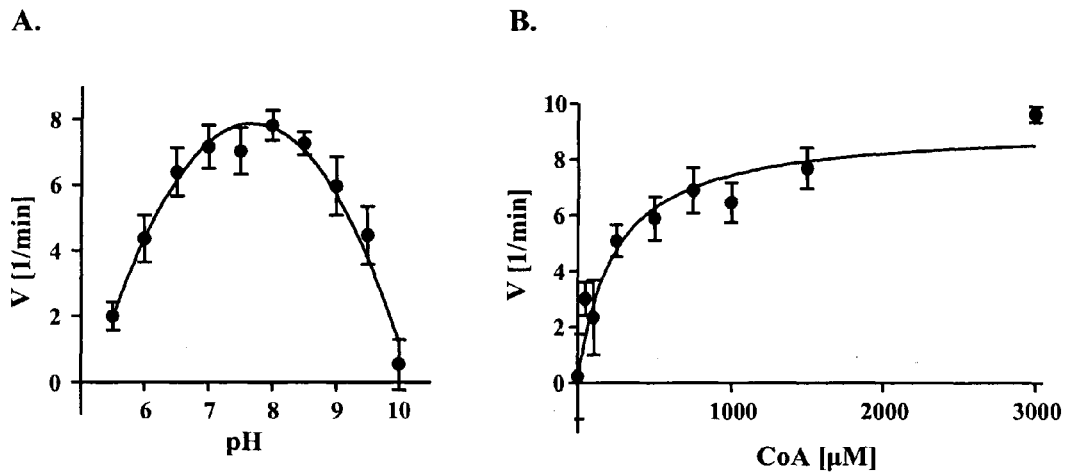
FIG. 9 provides graphs showing the enzymatic characterisation of Sppt with respect to SACP3.

Phosphopantetheinylation assays, and subsequent HPLC analysis, were carried out to determine the pH and CoA activity range of Sppt towards its cognate SACP3 carrier protein The optimum activity for Sppt was approximately pH 7.7, with a relatively broad pH activity range where approximately 25% of the activity was retained at pH 5.5 and 9.8 (FIG. 9). Sppt activity increased with increasing CoA concentrations and reached a maximum activity with concentrations greater than 1500 µM. The Michaelis-Menten fit of the experimental data yielded a $K_m$ value of 169.17±37.48 µM for Sppt with respect to CoA and a $k_{cat}$ value of 28.41±2.12 min$^d$. The catalytic efficiency of Sppt for CoA was 0.168 µM$^{-1}$ min$^{-1}$.

Sppt behaves similar to AcpS-like PPTs with specific carrier protein activation, a high pH optimum and low catalytic efficiencies with respect to CoA. Although most characterised PPTs show significantly higher catalytic efficiencies, Sppt has similar values to AcpS from *E. coli* which has reported $K_m$ values of 50 or 150 µM and a $k_{cat}$ value of approximately 10 min$^d$ (21,40). Sfp-like PPTs such as the *B. subtilis* Sfp and *P. aeruginosa* PcpS have pH optima between 6-7 while the Sppt optimum is more similar to the *B. subtilis* and *E. coli* AcpS PPTs with pH optima between 8-9. This high pH requirement may allow for appropriate electrostatic interactions between Sppt and the acidic SACP; and may explain its poor activation of the neutral MPCP. Optimum Sppt activity at higher pH's may also reflect the environmental conditions (pH 7-9) that favour cyanobacterial bloom formation over phytoplankton growth. Sppt's pH range is broader than other characterised PPTs, which may reflect the dynamic pH of cyanobacterial environments during eutrophication and subsequent bloom cycles.

Example 6

Sppt in vitro Phosphopantetheinylation of Non-Cognate Carrier Proteins

The ability of Sppt to activate carrier proteins from a range of secondary metabolism pathways was tested, including those from unicellular and filamentous, heterocyst-forming cyanobacteria. The carrier proteins tested were the *N. punctiforme* ATCC29133 PKS aryl carrier protein (ArCP) from HetM of glycolipid synthesis (NpArCP) and PKS ACP of nostopeptolide biosynthesis (NpACP); and the *M. aeruginosa* PCC7806 NRPS PCP from the loading module (McyG) of microcystin synthesis (MPCP). The *Bacillus brevis* ATCC8185 NRPS PCP involved in tyrocidine biosynthesis (TycPCP) was also used to test the ability of Sppt to phosphopantetheinylate carrier proteins from alternative bacterial kingdoms.

The *M. aeruginosa* PCC7806, peptidyl carrier protein, MPCP; and the *N. punctiforme* ATCC29133 aryl carrier protein, NpArCP, and acyl carrier protein, NpACP, were expressed and purified as previously described in Copp J. N., Roberts A. A., Marahiel M. A., Neilan B. A., 2007, *Characterization of PPTNs, a cyanobacterial phosphopantetheinyl transferase from Nodularia spumigena NSOR*10. *J. Bacteriol.*: 189(8):3133-9. The *Bacillus brevis* ATCC8185 TycPCP was expressed and purified according to the methods of Reuter et al. (1999), *Crystal structure of the surfactin synthetase-activating enzyme sfp: a prototype of the 4'-phosphopantetheinyl transferase superfamily*, EMBO J. 18:6823-6831. Protein concentrations were determined based on the calculated extinction coefficients: NpArCP 8,250 cm$^{-1}$M$^{-1}$, NpACP 13,940 cm$^{-1}$M$^{-1}$, MPCP 6,970 cm$^{-1}$M$^{-1}$ and TycPCP 9,530 cm$^{-1}$M$^{-1}$. Phosphopantetheinylation assays were carried out in 30 min reactions and analysed by ESI-mass spectrometry described in Example 4 above.

No phosphopantetheinylation of NpACP, MPCP, NpArCP and TycPCP by the *E. coli* PPTs was detected after heterologous expression.

Figure 10:
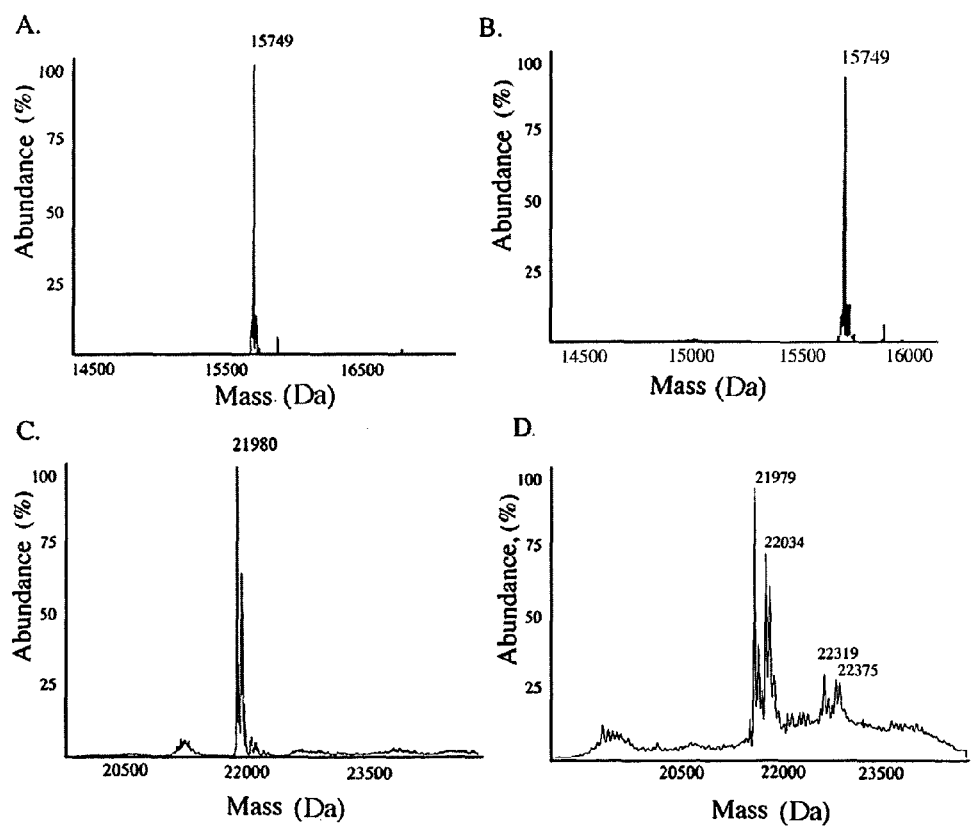
FIG. 10 shows mass spectra of *N. punctiforme* ATCC29133 aryl carrier protein (NpArCP) control (FIG. 10A), NpArCP after incubation with Sppt (FIG. 10B), *M. aeruginosa* PCC7806, peptidyl carrier protein (MPCP) control (FIG. 10C); and MPCP after incubation with Sppt (FIG. 10D).
Figures 11, 12:
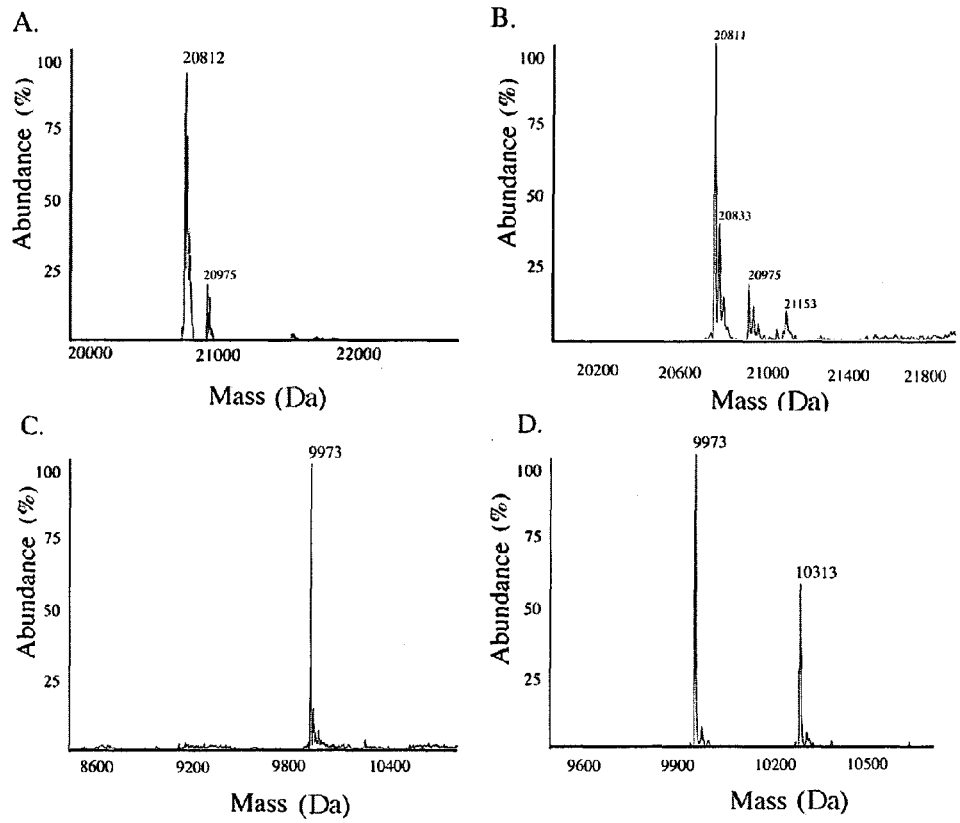
FIG. 11 shows mass spectra of *N. punctiforme* ATCC29133 acyl carrier protein (NpACP) control (FIG. 11A), NpACP with Sppt (FIG. 11B), *Bacillus brevis* ATCC8185 nonribosomal peptide synthetase peptidyl-carrier protein (TycPCP) control (FIG. 11C) and TycPCP after incubation with Sppt (FIG. 11D).
FIG. 12 is a table showing phosphopantetheinylation of non-cognate carrier proteins by the *Synechocystis* sp. PCC6803 PPT, Sppt. * Holo-CP was detected by the mass addition of a phosphopantetheinyl moiety (340 Da) via mass spectrometry. † The % holo-CP was estimated by comparison of holo- and apo-CP abundance in mass spectra. ND: not detected.

Sppt was unable to phosphopantetheinylate the *N. punctiforme* ATCC29133 NpArCP as shown by mass spectrometry (FIG. 10B). The spectrum of *M. aeruginosa* PCC7806MPCP, after incubation with Sppt, showed a small mass peak corresponding to the addition of a 340 Da phosphopantetheinyl moiety (22,319 Da) (FIG. 10D). This low intensity peak was consistently present in repeated experiments. Phosphopantetheinylated NpACP was not reproducibly detected after incubation with Sppt (FIG. 11B) and the mass peak of 20,153 Da was only slightly above that of the spectrum background. In contrast, approximately 54% of the *P. aeruginosa* PAO1 NRPS TycPCP was phosphopantetheinylated by Sppt (FIG. 11D, FIG. 12).

The inability of Sppt to activate non-cognate carrier proteins from other species was shown with the *N. punctiforme* ATCC29133 glycolipid synthesis NpArCP. This result was not surprising as *Synechocystis* sp. PCC6803 is unable to form heterocysts or fix nitrogen. The ability of Sppt to phosphopantetheinylate carrier proteins within NRPS and PKS pathways was also analysed using MPCP from microcystin synthesis in *M. aeruginosa* PCC7806 and NpACP from nostopeptolide synthesis in *N. punctiforme* ATCC29133.

Phosphopantetheinylation of MPCP and NpACP was detected, but only slightly above that of the spectrum background. NpACP phosphopantetheinylation could not be consistently reproduced in replicate assays. The inability of Sppt to activate carrier proteins from secondary metabolite pathways correlates with the lack of natural products synthesised by *Synechocystis* sp. PCC6803. However, the presence of an Sfp-like PPT in a species that only encodes carrier proteins for FAS raises interesting questions regarding the evolution of PPTs and secondary metabolite synthesis in cyanobacteria.

The ability of Sppt to phosphopantetheinylate the *Bacillus brevis* ATCC8185 carrier protein TycPCP was incongruous to the lack of activity towards other cyanobacterial carrier proteins. This may be explained by the size of the expressed TycPCP which is less than half the size of NpACP and MPCP. Therefore, the inability to phosphopantetheinylate the larger MPCP and NpACP carrier proteins could be due to electrostatic considerations and poor accessibility of active sites in these larger recombinant proteins.

Example 7

HetMNI Gene Cluster

Cyanobacterial PPTs present an interesting group of PPTs due to the presence of multiple secondary metabolites including polyketide, peptide synthetase and hybrid polyketide/peptide synthetase biosynthesis, PPTs associated with development of specialist cells for nitrogen fixation (heterocysts), Sfp-like PPTs with the notable absence of an AcpS-like PPT, and integrated Sfp-like PPTs within polyketide clusters. The majority of sequenced cyanobacterial genomes contain a singular Sfp-like PPT, However *Nostoc punctiforme* ATCC 2913 and *Gloeobacter violaceus* PCC 7421 both display three distinct PPTs within their respective genome sequences.

The divergent range of PPTs within cyanobacteria required more rigorous sequence analysis. A cyanobacterial screen for PPT enzymes was performed utilizing the available sequence data from published genomes. Conserved motif alignments (motif 3 and 4) from Sfp-like PPTs were targeted for the design of degenerate PCR primers. Novel cyanobacterial PPT genes were isolated from toxic, non-toxic, unicellular, and filamentous, heterocyst-forming cyanobacterial species. A phylogenetic tree constructed from published and partial cyanobacterial PPT sequences (FIG. 13) revealed the new phylotypes designated A and B. All cyanobacterial PPT fall in the W/KEA subfamily of Sfp-like PPTs.

Figure 13:
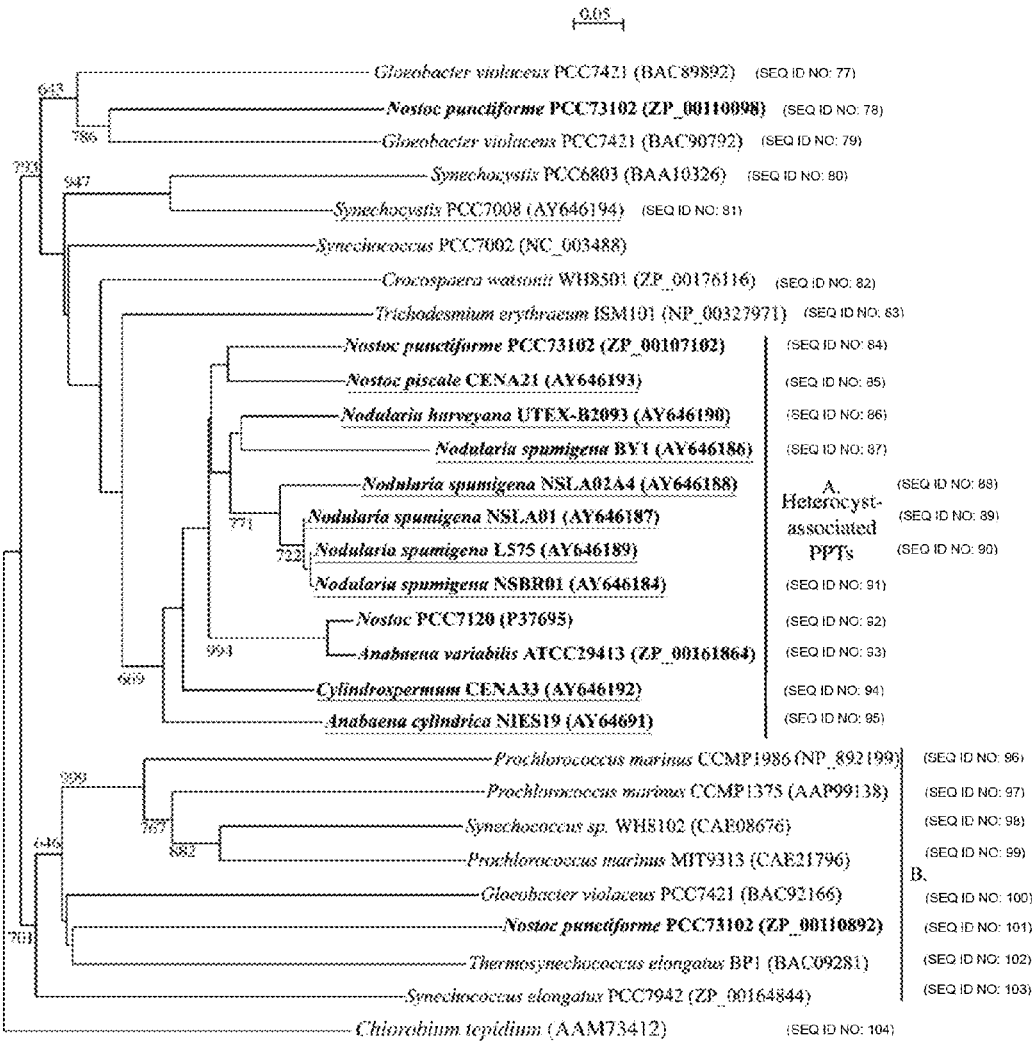
FIG. 13 is a phylogenetic tree diagram showing analysis of cyanobacterial PPTs. Accession numbers given in parenthesis, and underlined sequences indicate those isolated during this study. Significant bootstrap data (greater than 500 out of 1000 repeats) is shown. The PPT from the green sulphur bacterium *Chlorobium tepidium* was chosen as an outgroup. Distinct phylotypes are observed and depicted as subgroup A (associated with heterocyst forming cyanobacteria) and B respectively.
Figure 15:
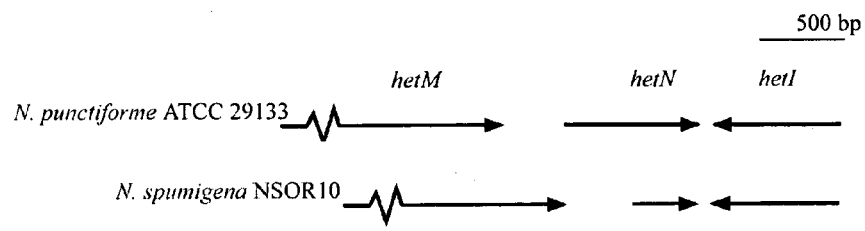
FIG. 15 is a diagram showing a comparison of the hetMNI loci from *Nostoc punctiforme* ATCC29133 and *Nodularia spumigena* NSOR10. Arrows indicate gene direction. A partial segment of the 1520 base pair (bp) hetM sequence is depicted by the broken arrow.

PPTs from known heterocyst-forming cyanobacteria formed a distinct Glade supported by bootstrap data and were designated het-type PPTs (A in FIG. 13). The heterocyst-forming *Nostoc punctiforme* PCC73102 species harbours three PPTs from the W/KEA subfamily within its genome. The *N. punctiforme* PPT associated with the heterocyst HET-MNI gene loci falls in the Het-type Glade, whereas the other two PPTs fall in alternative clades.

A second Glade (B in FIG. 13) includes PPTs from *Prochlorococcus, Synechococcus, Gloeobacter* and *N. punctiforme* species. Several of the sequences within this group were located adjacent to an ATPase gene. Alternatively, the *G. violaceus* and *N. punctiforme* PPTs in this group were both associated with polyketide biosynthetic clusters.

Sequencing of the *N. spumigena* HetMNI Locus

The *N. spumigena* PPT fragment identified by phylogenetic analysis as a het-type PPT potentially associated with heterocyst synthesis was subsequently selected for characterization. A flanking region of 3450 by was sequenced to allow analysis of the surrounding genomic region, revealing a heterocyst related HetMNI gene cluster (Genbank Accession No. AY836561).

Functional classification has not previously been observed in PPT phylogenetics. Analysis of the divergent range of cyanobacterial PPTs has allowed the designation of PPTs associated with heterocyst formation. Using gene alignments to screen PPT sequences has allowed the detection of heterocyst-associated PPTs within cyanobacterial genomes and the characterisation of a heterocyst biosynthesis locus in *N. spumigena* NSOR10.

Example 8

Isolation of *N. Spumigena* PPT (1) Media/Culturing

*N. spumigena* NSOR10 was cultured at room temperature on a 24 hour light/dark cycle in ASM media (see Provasoli, L., et al. 1957. *The development of artificial media for marine algae. Arch Mikrobiol* 25:392-428). DNA was extracted as previously described in (Moffitt, M. C. and B. A. Neilan. 2004. *Characterization of the nodularin synthetase gene cluster and proposed theory of the evolution of cyanobacterial hepatotoxins. Appl Environ Microbiol* 70:6353-62).

(2) DNA Amplification, Sequencing and Analysis

PCR and sequencing reactions were performed as previously described in Neilan, B. A. et al. 1994, *16S ribosomal RNA gene sequence and phylogeny of toxic Microcystis* sp. (cyanobacteria). *DNA Seq* 4:333-7. Panhandle-based gene walking by adaptor based and specific primers (Moffitt, M. C. and B. A. Neilan. 2004. *Characterization of the nodularin synthetase gene cluster and proposed theory of the evolution of cyanobacterial hepatotoxins. Appl Environ Microbiol* 70:6353-62) was utilised at the annealing temperature of 45-55° C. to amplify the unknown genomic regions flanking the *N. spumigena* PPT fragment (SEQ ID NO: 1). The output from BLAST (Basic Local Alignment Search Tool), Pileup from GCG and the multiple-sequence alignment tool from CLUSTAL X were utilized for the analysis and alignment of sequences. Automated sequencing was performed using the PRISM Big Dye cycle sequencing system and a model 373 sequencer (Applied Biosystems Inc., USA). Sequence analysis was performed using Applied Biosystems Autoassembler software.

(3) Southern Hybridisation Methods

Pure genomic DNA samples from *Nodularia spumigena* NSOR10 (~10 µg) were digested overnight with Xba I or Xmn I as per manufacturers recommendations (Promega, Australia). Digests and positive controls (0.5-1.0 ng of linearised plasmid pGEM-T-Easy (Promega) were separated on 0.8% agarose gels at 60 mV for approximately 2.5 hours and vacuum-blotted to a nylon membrane (Amersham). The DIG-High Prime DNA labelling kit (Roche, Australia) was utilised for Southern hybridisations. PPT probes were amplified with specific primers as follows. The primer pair slrup (5'-TGTT-TAAACTCACCTGTG-3') (SEQ ID NO: 15) and slrdn (5'-CCCAAGGTAACGAAACGA-3') (SEQ ID NO: 16) was utilised to amplify Slr0495 from *Synechocystis* sp. PCC 6803. The primer pair Npunfw (GGATCCGCGATCGCCAGTCT-GAGTTC) (SEQ ID NO: 17) and Npunry (GAGCTCTTTGTGTAGTAGCGAATTATC) (SEQ ID NO: 18) was utilised to amplify a PPT from *Nostoc punctiforme* ATCC 29133. The primer pair NpptF (5'-CATGAAAGATAT-CACGGCGCTT-3') (SEQ ID NO: 19) and NpptR (5'-GAA-GATAACAAGCTTGTATTGCC-3') (SEQ ID NO: 20) was used to amplify nchS from *Nodularia. spumigena*. Probes were labelled by PCR with digoxigenin (DIG) as per manufacturer's instructions (Roche) and tested for efficiency from 100 fg to 10 ng. Hybridisations were performed with overnight at 40° C., stringency washes were performed with 0.5% SSC with 0.1% SDS at 65° C. and signals were analysed by chemiluminescent detection with CPSD by a FUJIFILM Luminescent Image Analyzer LAS-3000.

(4) Creation of Expression Plasmids

The *N.* sp. heterocyst carrier protein synthase (hereafter nhcS) from *N. spumigena* NSOR10 (AY836561) was amplified by the primer pair NpptF and NpptR (as described in "(3) Southern Hybridisation Methods") above). The 720 bp PCR-amplified product was cloned into pGEM-T (Promega) and this plasmid was then digested and the appropriate fragment ligated into pET30 (Novagen) to yield the expression plasmid pNhcS.

The *N. punctiforme* PCC73102 HetM was amplified from the heterocyst hetMNI locus encoding the ArCP/ketoreductase HetM (ZP_00107100). The primer pair HetMF (5'-GC-CATGGCTATAAAACAGTCTTTC-3') (SEQ ID NO: 21) and HetMR (5'-GGGATCCGAGATTCAAGAAACC-3') (SEQ ID NO: 22) were utilised to amplify a 1.7 Kb fragment, which was cloned into the pGEM staging vector. Subsequent restriction and cloning into the pET30 expression vector created pHetM. The pArCP expression vector was constructed in a similar manner utilising the primers HetMF (as above) and ArCPR (5'-TAGCTCGAGAACCATCTTGCAC-3') (SEQ ID NO: 23), to amplify and clone the 260 bp ArCP domain of hetM and create pArCP.

The *N. spumigena* NSOR10 peptidyl carrier protein (hereafter PCP) and acyl carrier protein (hereafter ACP) (hereby called Npcp and Nacp) were amplified from the hybrid NRPS-PKS ndaC (AA064404) within the ndaS gene cluster responsible for the production of the hepatotoxin Nodularin (see Moffitt, M. C. and B. A. Neilan. 2004. *Characterization of the nodularin synthetase gene cluster and proposed theory of the evolution of cyanobacterial hepatotoxins. Appl Environ Microbiol* 70:6353-62). The primer pairs NpcpF (5'-CTC-GAGCAGCCTCTACAACTGCA-3') (SEQ ID NO: 24) and NpcpR (5'-GGATCCGCCAGGAGAACGGCGG-3') (SEQ ID NO: 25) and NacpF (GGAGCTCTTTTCCAAACAT-TCT) (SEQ ID NO: 26) and NacpR (5'-GGGATC-CTCTAAGCATTCCATCAGTC-3') (SEQ ID NO: 27) were utilised. The resulting fragments were manipulated as described above to yield pNACP and pNPCP respectively.

The *Synechocystis* sp. fatty acid synthesis acyl carrier protein (hereafter FAS ACP), hereby called Sacp (BA000022), was constructed from the primer pair 2084NdeF (5'-GCATATGAATCAGGAAATTT-3') (SEQ ID NO: 28) and 2084XhoR (5'-CCTCGAGTAATTTACTTTCGATATGCT-CAAC-3') (SEQ ID NO: 29) and cloned as above to yield pSACP.

The *Microcystis aeruginosa* PCP was amplified from the hybrid NRPS-PKS mcyG (AAX73195) from the mcyS gene cluster responsible for the production of the hepatotoxin microcystin (see Tittett, D., et al. 2000. *Structural organization of microcystin biosynthesis in Microcystits aeruginosa PCC7806: an integrated peptide-polyketide synthetase system. Chem. Biol* 7:753-64). The PCR primers MpcpF (5'-GGATCCTGAACAGGGA-3') (SEQ ID NO: 30) and MpcpR (5'-CTCGAGATGGCGACGGCTCC-3') (SEQ ID NO: 31) were used to construct the expression vectors as outlined above to create pMPCP.

The *Nostoc punctiforme* NSOR10 NRPS PCP, from this point called Nppcp, (ZP_00110897) was amplified from an uncharacterised gene cluster. This locus is hypothesised to be responsible for nostopeptolide production in *N. punctiforme* ATCC29133 due to its similarity to the characterised gene cluster in *Nostoc* sp. GSV224 (see Hoffmann, D., et al. 2003. *Sequence analysis and biochemical characterization of the nostopeptolide A biosynthetic gene cluster from Nostoc* sp. GSV224. *Gene* 311:171-80). NosA, a large NRPS gene within this cluster, comprises of four NRPS modules. The C-terminal NosA PCP was amplified from the putative nostopeptolide biosynthetic cluster utilising the primer pairs NppcpBF (5'-GGATCCTAAAATCTAGGCTAG-3') (SEQ ID NO: 32) NppcpSR (5'-GAGCTCAAATTGTTATTTCTT-3') (SEQ ID NO: 33) and cloned as above to yield pNpPCP.

(5) Protein Expression, Purification and Enzyme Activity Analysis

Expression plasmids were separated, transfected into *E. coli* as host cells and expression analysis performed as follows. Sacp was expressed at 37° C. for 2 hours with 1 mM IPTG (isopropyl-beta-D-thiogalactopyranoside). NhcS, Arcp and Mpcp were expressed at 30° C. for 4 h with 0.2 mM IPTG. Nppcp was expressed at 22-24° C., 0.1 mM IPTG for 6 hours. HetM was expressed at 18° C., overnight with 0.1 mM IPTG, visualised as a soluble 63.3 kDa protein and verified via western blot as per manufacturer's instructions (Qiagen). However, analysis of HetM via nanospray ion trap mass spectrometry could not be performed due to inadequate yields. The plasmid encoding the ArCP domain of hetM was therefore constructed and the 15.6 kDa Arcp was subsequently expressed in adequate yields. Attempts to resolve the low solubility of the Nacp and Npcp carrier proteins included variations in expression time (2-24 hours), temperature (18-37° C.) and IPTG concentration (0.1-1 mM). After expression cells were pelleted at 4,000 rpm and frozen at −80° C. overnight. Pellets were then thawed on ice, resuspended in 5 ml 50 mM Hepes (Sigma) pH 7.4 and either subjected to 3 passages through a cooled French press at 1000 psi or sonicated at 4° C., 30% amplitude, for 25 seconds with a 0.5 second pulse. The soluble fraction was collected after centrifugation at 20,000 g for 30 min at 4° C. An Amersham HighTrap Ni-chelating column was utilised for purification of the recombinant proteins. Fractions containing the desired protein (as determined by SDS-PAGE) were pooled, desalted and snap frozen (with 8% glycerol) in liquid nitrogen for storage at −80° C. Concentration of the purified proteins was calculated using the absorbance at $OD_{280}$ and the respective absorbance factors of the recombinant proteins (NhcS 37650, HetM 67430, ArCP 8250, Sacp 6970, Mpcp 6970 and Nppcp 13940).

PPT assays were carried out as previously described in Finking, R., et al., (2002) *Characterization of a new type of phosphopantetheinyl transferase for fatty acid and siderophore synthesis in Pseudomonas aeruginosa. J Biol Chem* 277:50293-302). In brief, a 100-400 µL reaction comprising of 50 mM Tris-HCl pH 7.4, 12.5 mM MgCl, 0.5 mM CoA, 2 µM DTT, 30 µg of the respective carrier proteins (CPs) and 300 nM of PPT was incubated at 37° C. for 30 minutes. Reactions were terminated by the addition of 1 ml of 10% TCA. Assays were precipitated overnight at −20° C. before at centrifugation 4° C., for 15 mins at 16,000 g. Protein pellets were analysed by electrospray ionisation mass spectrometry (ESI-MS). Spectra were acquired using an API QStar Pulsar i hybrid tandem mass spectrometer (Applied Biosystems, Foster City Calif.). Samples (~200-400 fmol) were dissolved in water:acetonitrile:formic acid (50:49:1), loaded (1 µl) into nanospray needles (Proxeon, Denmark) and the tip positioned ~10 mm from the orifice. Nitrogen was used as curtain gas and a potential of 900 V applied to the needle. A T of MS scan was acquired (m/z 550-2000, 1 second) and accumulated for ~1 minute into a single file. Spectra were deconvoluted using the Bayesian reconstruction method contained within the Analyst QS software.

(6) Activation of NpACP by Coexpression with NPPT in *E. coli*.

The *Nodularia spumigena* PPT, NPPT, was amplified by PCR using the primers NpptF (5'-TGCATATGACGGCGCT-TAATCATT-3') (SEQ ID NO: 34) and NpptR (5'TCTC-GAGTCAGTATTGCCAACAC-3') (SEQ ID NO: 35) and was subsequently cloned into pGEM-T-Easy (Promega). NPPT was then subcloned into the expression vector pET30a (Novagen) by digestion with NcoI and XhoI (New England Biolabs) to yield pNPPT2. NPPT, complete with the T7 promoter and transcriptional terminator originally from pET30a, was released from pNPPT2 with DraIII and SphI (New England Biolabs) and blunt-ended with Klenow enzyme (Promega). The fragment was subsequently cloned into AvaI-linearised, blunt-ended and phosphorylated pRARE (Novagen) to yield pNPPT3.

The constructs pNPPT3 and pNpACP were sequentially transformed into BL21(DE3) (Novagen) for coexpression of the NPPT and NpACP proteins. In the control experiments, NpACP was expressed with pRARE only. NpACP proteins which were coexpressed with pNPPT3 or pRARE were purified on a Hi-Trap nickel column and precipitated with 10% trichloracetic acid. Molecular masses were determined with Nanospray-MS analysis.

Example 9

Activity of nhcS (1) Sequencing and Analysis of the HetMNI Locus

Flanking regions of the partial PPT gene fragment were amplified to allow sequencing of 3450 by of the *N. spumigena* NSOR10 hetMNI locus (AY836561). Sequence analysis revealed the 240aa nhcS PPT, a 27,555 Da protein with an isoelectric point (pI) of 6.1. NhcS displayed 81% similarity to HetI of *Nostoc* sp. PCC 7120, 58% similarity to the *Synechocystis* sp. PCC 6803 Slr0495 and 55% similarity to Sfp from *B. subtilis* (FIG. 14). This PPT is encoded in reverse orientation to the hetM and hetN genes, as observed in the hetMNI locus of the heterocyst forming cyanobacteria *Nostoc* sp. PCC 7120, *A. variabilis* ATCC 29413, and N. punctiforme ATCC 29133 (FIG. 14).

The predicted protein products of the genes downstream of nhcS in the hetMNI loci were also analysed and compared to homologous proteins. The partial fragment of the *N. spumigena* iterative PKS gene hetM was sequenced and showed 90% similarity to the corresponding fragment of *N. punctiforme* hetM (also called hglB). The *N. spumigena* HetN is a 126-residue protein that displayed 83% similarity to the C-terminal half of *A. variabilis* HetN (a 263 residue protein). This domain encodes a unique reductase protein that has a role in heterocyst suppression via inhibition of HetR (Li et al., 2002 "Expression of hetN during heterocyst differentiation and its inhibition of hetR up-regulation in the cyanobacterium *Anabaena* sp. PCC7120" FEBS Letters 517:87-91). No ORFs were detected in the sequenced region extending 900 by upstream of nhcS.

(2) Southern Hybridisation

Figure 16:
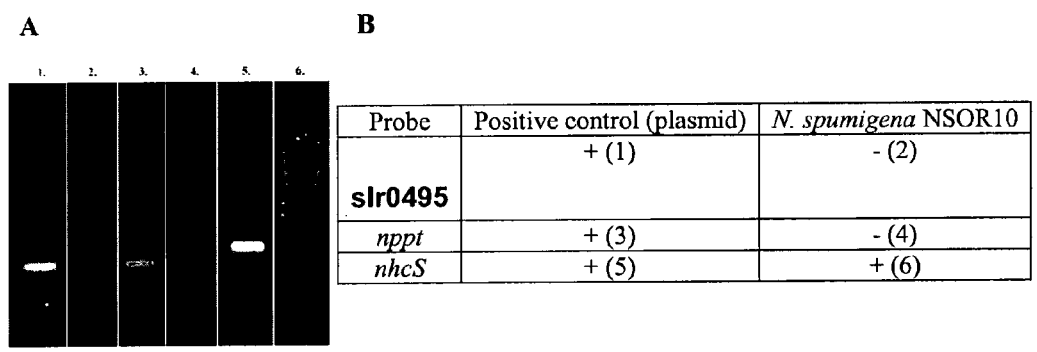
FIG. 16 shows *N. spumigena* NSOR10 southern hybridisation data.

Southern probes were utilised to ascertain the number of PPTs encoded within the *N. spumigena* NSOR10 genome. Probes were constructed from a diverse range of cyanobacterial PPTs including nhcS, slr0495 from *Synechocystis* sp. PCC 6803 (BAA10326) and a PPT from *Nostoc punctiforme* ATCC 29133 (ZP_00110892). These PPTs are placed in distinct cyanobacterial phylogenetic clades. Probe efficiency and specificity was detected to 10 pg as verified through controls (not shown). Hybridisations performed with the nhcS probe revealed a singular band from *N. spumigena* NSOR10 (FIG. 16) and no hybridisation was detected with the slr0495 or nppt probes. Together, these experiments suggest that nhcS is the single PPT encoded by *N. spumigena* NSOR10.

(3) Expression and Purification of Recombinant Proteins

In order to confirm the pantetheinyl transferase activity of nhcS, this enzyme was expressed as a 27.6 kDa His-tagged, soluble protein. The Arcp from the hetMNI locus in *N. punctiforme* ATCC29133 was chosen due to the similarity of the hetMNI genes to *N. spumigena* NSOR10. No ArCP pantetheinylation was seen after heterologous expression in *E. coli*. Sacp was expressed as a 14.8 kDa protein. After expression of the ACP in *E. coli* 40% of the protein was in the holo form. Production of soluble Nacp and Npcp from *N. spumigena* NSOR10, despite multiple variations in expression parameters, did not yield soluble protein for analysis as deduced by western blot (not shown). Mpcp and Nppcp were expressed as 22.0 kDa and 20.8 kDa proteins respectively; no pantetheinylation was seen after expression in *E. coli*.

(4) Analysis of nhcS Activity

Figure 17:
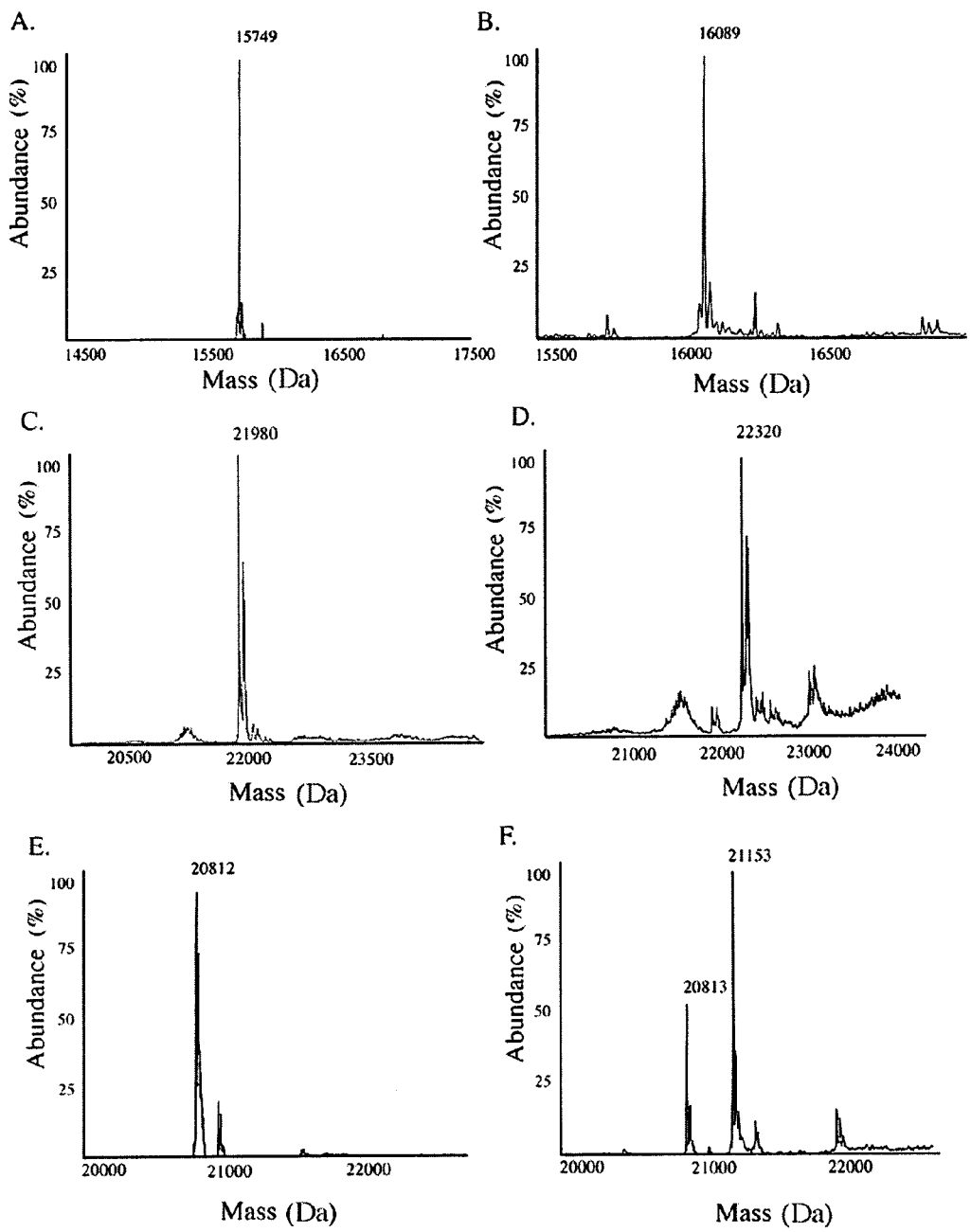
FIG. 17 shows spectra derived from nanospray mass spectrometry of aryl carrier protein (ArCP), peptidyl carrier protein (PCP) and acyl carrier protein (ACP) pantetheinylation.

Activity was detected by ionisation mass spectrometry through the mass addition of 350 da, relating to the incorporation of the pantetheinyl arm of CoA transferred by the PPT to the CP (FIG. 17).

NhcS activity was initially confirmed utilising the cognate HetM ArCP from the associated hetMNI gene cluster (in *N. punctiforme* ATCC29133). The conversion of the apo-ArCP (15.75 kDa) to the holo-ArCP (16.05 kDa) is seen in FIG. 17B), and shows the role of this enzyme in the synthesis of heterocyst glycolipids.

Enzymatic analysis of NhcS activity toward secondary metabolite PCPs from NRPS was tested with Nppcp and Mpcp. Mass spectroscopy analyses show the 350 Da addition of the pantetheinyl moiety from CoA to each of the respective CPs tested. The successful expression of the PCP from the Nostopeptolide (nosA) and the Microcystin (mcyG) biosynthetic gene clusters allowed the detection and analysis of nhcS phosphopantetheinylation in secondary metabolism. Complete pantetheinylation of Mpcp was achieved in a 30 min assay. Nppcp was pantetheinylated, showing that nhcS can activate carrier proteins from biosynthetic pathways that are not present in *N. spumigena* NSOR10.

Control reactions were performed without nhcS. There was no detectable pantetheinylation of the PCPs after heterologous expression in *E. coli*.

NhcS can therefore act in each of FAS, heterocyst glycolipid synthesis and biosynthesis of secondary metabolites such as the hybrid polyketide/non-ribosomal peptide nodularin. The ability of nhcS to activate non-cognate secondary metabolite CPs has great potential for application in biotechnological fields. Pantetheinylation of non-cognate carrier proteins from alternative hosts demonstrates the application of this PPT for active synthesis of biosynthetic clusters from a diverse range of species.

Example 10

Complementation of *Synechocystis* sp. PCC6803 with NsPPT

The *Nodularia spumigena* NSOR10 PPT, NsPPT (Genbank accession number AY646183), was expressed under the control of a nitrate inducible promoter, PnirA, from *Synecho*-

*coccus* sp. strain PCC7942, to complement Sppt activity in vivo (34). PnirA was amplified with the primers nirAF (5'-TTCTAGATCCCTCTCAGATCAAAAAG-3') (SEQ ID NO: 36) and nirAR (5'TGCATATGGGATTCATCTGCCTAC-3') (SEQ ID NO: 37) and the fragment was cloned into pET30a with XbaI and NdeI to yield pPnirA (Novagen). NsPPT, was amplified by with the primers NpptF (5'-TGCATATGACGGCGCTTAATCATT-3') (SEQ ID NO: 34) and NpptR (5'-TCTCGAGTCAGTATTGCCAACAC-3') (SEQ ID NO: 35) and was subsequently cloned into pPnirA with NdeI and XhoI. NsPPT, complete with the PnirA promoter and T7 transcriptional terminator, was released from this construct with DraIII and SphI and blunt-ended with Klenow enzyme (Promega) for ligation into PstI-linearised pKW1188, which harbours the slr0168 photosystem II gene flanking regions and a kanamycin resistance cassette. The resulting plasmid was naturally transformed into *Synechocystis* sp. PCC6803 for homologous recombination into slr0168.

Transformants were selected on BGTS plates supplemented with 10 μml$^{-1}$ kanamycin. The NsPPT-complemented strain was designated *Synechocystis* sp. PCC6803 ΔNsPPT$^+$ (ΔNsPPT$^+$). The Sppt knockout plasmid, pGCSlr, was naturally transformed into this strain for disruption of the Sppt gene. ddH$_2$O was also transformed into ΔNsPPT$^+$ as a negative control. NsPPT-complementated colonies were PCR-screened for complete segregation of Sppt gene disruption using the primers slrup and slrdown. Complementation and knockout experiments were carried out three times in duplicate.

While the invention has been described in the manner and detail as above, it will be appreciated by persons skilled in the art that numerous variations and/or modifications including various omissions, substitutions, and/or changes in form or detail may be made to the invention as shown in the specific embodiments without departing from the spirit or scope of the invention as broadly described. The present embodiments are, therefore, to be considered in all respects as illustrative and not restrictive.

Any description of prior art documents herein, or statements herein derived from or based on those documents, is not an admission that the documents or derived statements are part of the common general knowledge of the relevant art in Australia or elsewhere.

The invention claimed is:

1. A method for the production of secondary metabolites, the method comprising:
    (a) transforming *Synechocystis* sp. bacteria with one or more bacterial peptide synthetase genes required for production of secondary metabolites;
    (b) culturing the *Synechocystis* sp. bacteria under conditions suitable for expression of the one or more genes required for production of secondary metabolites; and
    (c) purifying the secondary metabolites from the bacteria, wherein said *Synechocystis* sp. bacteria express a *Nodularia* sp. phosphopantetheinyl transferase (PPT) that is needed for the production of the secondary metabolite, wherein said *Synechocystis* sp. bacteria comprise an inactivated endogenous phosphopantetheinyl transferase (Sppt) gene.

2. The method of claim 1, further comprising prior to step (c), the step of screening the *Synechocystis* sp. bacteria for production of secondary metabolites.

3. The method of claim 2, wherein the screening step comprises high performance liquid chromatography, mass spectrometry or a combination thereof.

4. The method of claim 1 wherein the secondary metabolite is a peptide or an analogue thereof which retains substantially the same function as the peptide.

5. The method of claim 4, wherein the peptide or analogue thereof is a bioactive compound.

6. The method of claim 5, wherein the bioactive compound is an anti-microbial agent, an anti-viral agent, an anti-fungal agent, an anti-cancer agent, an immunosuppressive agent, an anaesthetic, an analgesic, an antitumour product, an antibiotic, an anti-cholesterolemic, an anti-parasitic agent, a veterinary therapeutic agent, an agrochemical, or a cosmetic.

7. The method of claim 1 wherein said gene required for production of secondary metabolites is operably linked to a promoter active in *Synechocystis* sp.

8. The method of claim 7, wherein the promoter is inducible.

9. The method of claim 8, wherein the promoter is inducible by varying intensity of light to which the bacteria are exposed during culture.

10. The method of claim 1 wherein said gene required for production of secondary metabolites is in a plasmid, phosmid or cosmid.

11. The method of claim 1 wherein said transforming is transposon-mediated.

12. The method of claim 1 wherein the bacteria are transformed with multiple bacterial peptide synthetase genes forming a biosynthetic peptide synthetase gene cluster.

13. The method of claim 1 wherein the exogenous PPT is encoded by a gene that is stably integrated into a *Synechocystis* sp. genome.

14. The method of claim 1, wherein the exogenous PPT is a cyanobacterial PPT.

15. The method of claim 1, wherein the PPT is from *Nodularia spumigena*.

16. The method of claim 1, wherein the PPT is from *Nodularia spumigena* NSOR10.

17. The method of claim 16, wherein the PPT comprises the amino acid sequence as set forth in SEQ ID NO: 1, or a variant or fragment thereof having PPT activity.

18. The method of claim 1 wherein the *Synechocystis* sp. is *Synechocystis* sp. PCC6803.

19. The method of claim 1, wherein the one or more bacterial peptide synthetase genes are cyanobacterial peptide synthetase genes.

* * * * *

SEQUENCE LISTING

```
<160> NUMBER OF SEQ ID NOS: 104

<210> SEQ ID NO 1
<211> LENGTH: 239
<212> TYPE: PRT
<213> ORGANISM: Nodularia spumigena NSOR10

<400> SEQUENCE: 1

Met Thr Ala Leu Asn His Leu Trp Leu Pro Val Pro Thr Asn Leu Thr
1               5                   10                  15

Leu Leu Pro Asn Asp Val His Ile Trp Arg Ile His Leu Asp Val Pro
            20                  25                  30

Glu Ala Gln Gln Asn Leu Leu Ala Thr Leu Ser Gly Asp Glu Leu
        35                  40                  45

Thr Arg Ala Asn Arg Phe His Phe Gln Glu His Arg Gln Arg Phe Ile
    50                  55                  60

Ala Gly Arg Gly Ile Leu Arg Ser Ile Leu Gly Ser Tyr Leu Gly Ile
65                  70                  75                  80

Glu Pro Gln Arg Val Leu Phe Asp Tyr Gln Glu Arg Gly Lys Pro Ile
                85                  90                  95

Leu Ala Asp Ser Leu Ala Lys Ser Gly Leu Trp Phe Asn Leu Ser His
            100                 105                 110

Ser Gln Gly Leu Ala Leu Cys Ala Val Asn Tyr His Asn Arg Ile Gly
        115                 120                 125

Ile Asp Leu Glu Tyr Ile Arg Arg Met Ser Asp Val Glu Ala Leu Ala
    130                 135                 140

Lys Arg Phe Phe Leu Pro Arg Glu Tyr Asp Val Val Arg Ser Leu Ser
145                 150                 155                 160

Asp His Gln Gln Gln Glu Ile Phe Phe Arg Tyr Trp Thr Cys Lys Glu
                165                 170                 175

Ala Tyr Leu Lys Ala Thr Gly Glu Gly Leu Ala Gln Leu Glu Gln Val
            180                 185                 190

Glu Val Leu Leu Asn Pro Thr Glu Pro Ala Gln Leu Gln Thr Ser Glu
        195                 200                 205

Ser Trp Ser Leu Phe Glu Leu Arg Ala Ala Glu Asp Tyr Phe Ala Ala
    210                 215                 220
```

Val Val Val Glu Gly Ser Gly Cys Asn Leu Gln Cys Trp Gln Tyr
225                 230                 235

<210> SEQ ID NO 2
<211> LENGTH: 277
<212> TYPE: PRT
<213> ORGANISM: Synechocystis sp. PCC6803

<400> SEQUENCE: 2

Met Ala Ile Ser Ala Glu Phe Ala Leu Cys Leu Asn Ser Pro Val Leu
1               5                   10                  15

Pro Gln Pro Gln Ile Trp Leu Cys Pro Thr Asp Arg Pro Leu Ile Pro
            20                  25                  30

Gly Tyr Gln Ala Leu Leu Ser Ser Glu Glu Met Ala Arg Gly Glu Arg
        35                  40                  45

Tyr Gln Arg Pro Gln Asp Lys Gln Arg Phe Leu Thr Met Arg Leu Ala
    50                  55                  60

Leu Arg Ile Leu Leu Ala Arg Gln Leu Asp Cys Leu Pro Gln Gln Leu
65                  70                  75                  80

Gln Phe Thr Tyr Gly Pro Gln Gly Lys Pro Glu Leu Val Asp Arg Glu
                85                  90                  95

Arg Arg Ser Pro Trp Phe Asn Val Ala His Ser Gly Asn Tyr Gly Leu
            100                 105                 110

Ile Gly Leu Ser Thr Glu Gly Glu Ile Gly Val Asp Leu Gln Ile Met
        115                 120                 125

Leu Pro Lys Pro His Tyr Leu Lys Leu Ala Lys Arg Phe Phe Ala Pro
130                 135                 140

Gln Glu Val Gln Gln Leu Glu Ser Leu Glu Gly Lys Arg Thr Lys
145                 150                 155                 160

Leu Phe Tyr Gln Leu Trp Thr Ala Lys Glu Ala Phe Leu Lys Ala Thr
                165                 170                 175

Gly Lys Gly Ile Ser Gly Gly Leu Asn Gln Val Ile Pro Asp Glu Asn
            180                 185                 190

Leu Ala Lys Tyr Gln Tyr Leu Pro Asp Ser Gly Asp Thr Asn His Trp
        195                 200                 205

Arg Leu Ser Ser Gln Pro Leu Leu Ala Asp Gln Gly Ser Asn Asp Asn
210                 215                 220

Tyr Trp Met Ala Ile Ala Trp Cys Thr Asn Glu Val Asn Gln Val Glu
225                 230                 235                 240

Ser Asn Tyr Leu Pro Asn Ile Gln Pro Phe Gln Trp Pro Arg Asn Leu
                245                 250                 255

His Ser Leu Pro Ser Phe Arg Tyr Leu Gly Lys Gly Glu Phe Gln His
            260                 265                 270

Thr Gly Gly Arg Tyr
        275

<210> SEQ ID NO 3
<211> LENGTH: 17
<212> TYPE: DNA
<213> ORGANISM: Artificial
<220> FEATURE:
<223> OTHER INFORMATION: Based on cyanobacterial PPT sequence
<220> FEATURE:
<221> NAME/KEY: misc_feature
<222> LOCATION: (12)..(12)
<223> OTHER INFORMATION: n is a, c, g, or t

<400> SEQUENCE: 3
caggagtayg gnaarcc                                                        17

<210> SEQ ID NO 4
<211> LENGTH: 17
<212> TYPE: DNA
<213> ORGANISM: Artificial
<220> FEATURE:
<223> OTHER INFORMATION: Based on cyanobacterial PPT sequence
<220> FEATURE:
<221> NAME/KEY: misc_feature
<222> LOCATION: (15)..(15)
<223> OTHER INFORMATION: n is a, c, g, or t

<400> SEQUENCE: 4
ttctcgatrt cdatncc                                                        17

<210> SEQ ID NO 5
<211> LENGTH: 22
<212> TYPE: DNA
<213> ORGANISM: Artificial
<220> FEATURE:
<223> OTHER INFORMATION: Based on heterocyst PPT sequence

<400> SEQUENCE: 5
gcccgtggta aacaaatatt ag                                                  22

<210> SEQ ID NO 6
<211> LENGTH: 17
<212> TYPE: DNA
<213> ORGANISM: Artificial
<220> FEATURE:
<223> OTHER INFORMATION: Based on heterocyst PPT sequence

<400> SEQUENCE: 6
gcctctttac aagtcca                                                        17

<210> SEQ ID NO 7
<211> LENGTH: 21
<212> TYPE: DNA
<213> ORGANISM: Artificial
<220> FEATURE:
<223> OTHER INFORMATION: Based on Synechocystis sp. PCC6803 sequence

<400> SEQUENCE: 7
gtaaactcca ttaacgctgg c                                                   21

<210> SEQ ID NO 8
<211> LENGTH: 21
<212> TYPE: DNA
<213> ORGANISM: Artificial
<220> FEATURE:
<223> OTHER INFORMATION: Based on Synechocystis sp. PCC6803 sequence

<400> SEQUENCE: 8
ggtgcaaatc cgttacatgg a                                                   21

<210> SEQ ID NO 9
<211> LENGTH: 16
<212> TYPE: DNA
<213> ORGANISM: Artificial
<220> FEATURE:
<223> OTHER INFORMATION: Based on Synechocystis sp. PCC6803 sequence

<400> SEQUENCE: 9
tgtttaaact cacctg                                                         16

<210> SEQ ID NO 10
<211> LENGTH: 16
<212> TYPE: DNA
<213> ORGANISM: Artificial
<220> FEATURE:
<223> OTHER INFORMATION: Based on Synechocystis sp. PCC6803 sequence

<400> SEQUENCE: 10
cccaaggtta cgaaac                                                    16

<210> SEQ ID NO 11
<211> LENGTH: 22
<212> TYPE: DNA
<213> ORGANISM: Artificial
<220> FEATURE:
<223> OTHER INFORMATION: Based on Synechocystis sp. PCC6803 fatty acid
      synthesis (SACP) sequence (AcpP BA000022)

<400> SEQUENCE: 11
ggaattctga atcaggaaat tt                                             22

<210> SEQ ID NO 12
<211> LENGTH: 22
<212> TYPE: DNA
<213> ORGANISM: Artificial
<220> FEATURE:
<223> OTHER INFORMATION: Based on the Synechocystis sp. PCC6803 fatty
      acid synthesis (SACP) sequence, (AcpP BA000022)

<400> SEQUENCE: 12
ctcggctcca aaagctttg gg                                              22

<210> SEQ ID NO 13
<211> LENGTH: 20
<212> TYPE: DNA
<213> ORGANISM: Artificial
<220> FEATURE:
<223> OTHER INFORMATION: Based on Synechocystis sp. PCC6803 fatty acid
      synthesis (SACP) (AcpP BA000022)

<400> SEQUENCE: 13
gcatatgaat caggaaattt                                                20

<210> SEQ ID NO 14
<211> LENGTH: 31
<212> TYPE: DNA
<213> ORGANISM: Artificial
<220> FEATURE:
<223> OTHER INFORMATION: Based on Synechocystis sp. PCC6803 fatty acid
      synthesis (SACP) (AcpP BA000022)

<400> SEQUENCE: 14
cctcgagtaa tttactttcg atatgctcaa c                                   31

<210> SEQ ID NO 15
<211> LENGTH: 18
<212> TYPE: DNA
<213> ORGANISM: Artificial
<220> FEATURE:
<223> OTHER INFORMATION: Based on Synechocystis sp. PCC 6803 Slr0495
      sequence

<400> SEQUENCE: 15
tgtttaaact cacctgtg                                                  18

<210> SEQ ID NO 16

```
<211> LENGTH: 18
<212> TYPE: DNA
<213> ORGANISM: Artificial
<220> FEATURE:
<223> OTHER INFORMATION: Based on Synechocystis sp. PCC 6803 Slr0495
      sequence

<400> SEQUENCE: 16
cccaaggtaa cgaaacga                                                 18

<210> SEQ ID NO 17
<211> LENGTH: 26
<212> TYPE: DNA
<213> ORGANISM: Artificial
<220> FEATURE:
<223> OTHER INFORMATION: Based on Nostoc punctiforme ATCC 29133 PPT
      sequence

<400> SEQUENCE: 17
ggatccgcga tcgccagtct gagttc                                        26

<210> SEQ ID NO 18
<211> LENGTH: 27
<212> TYPE: DNA
<213> ORGANISM: Artificial
<220> FEATURE:
<223> OTHER INFORMATION: Based on Nostoc punctiforme ATCC 29133 reverse
      sequence

<400> SEQUENCE: 18
gagctctttg tgtagtagcg aattatc                                       27

<210> SEQ ID NO 19
<211> LENGTH: 22
<212> TYPE: DNA
<213> ORGANISM: Artificial
<220> FEATURE:
<223> OTHER INFORMATION: Based on Nodularia. Spumigena nchS sequence

<400> SEQUENCE: 19
catgaaagat atcacggcgc tt                                            22

<210> SEQ ID NO 20
<211> LENGTH: 23
<212> TYPE: DNA
<213> ORGANISM: Artificial
<220> FEATURE:
<223> OTHER INFORMATION: Based on Nodularia. Spumigena nchS sequence

<400> SEQUENCE: 20
gaagataaca agcttgtatt gcc                                           23

<210> SEQ ID NO 21
<211> LENGTH: 24
<212> TYPE: DNA
<213> ORGANISM: Artificial
<220> FEATURE:
<223> OTHER INFORMATION: Based on heterocyst hetMNI locus encoding the
      ArCP/ketoreductase HetM (ZP_00107100)

<400> SEQUENCE: 21
gccatggcta taaaacagtc tttc                                          24

<210> SEQ ID NO 22
<211> LENGTH: 22
<212> TYPE: DNA
<213> ORGANISM: Artificial
```

<220> FEATURE:
<223> OTHER INFORMATION: Based on the heterocyst hetMNI locus encoding
     the ArCP/ketoreductase HetM (ZP_00107100)

<400> SEQUENCE: 22
gggatccgag attcaagaaa cc                                              22

<210> SEQ ID NO 23
<211> LENGTH: 22
<212> TYPE: DNA
<213> ORGANISM: Artificial
<220> FEATURE:
<223> OTHER INFORMATION: Based on the heterocyst hetMNI locus encoding
     the ArCP/ketoreductase HetM (ZP_00107100)

<400> SEQUENCE: 23
tagctcgaga accatcttgc ac                                              22

<210> SEQ ID NO 24
<211> LENGTH: 23
<212> TYPE: DNA
<213> ORGANISM: Artificial
<220> FEATURE:
<223> OTHER INFORMATION: Baed on hybrid NRPS-PKS ndaC (AAO64404)
     sequence within the ndaS gene

<400> SEQUENCE: 24
ctcgagcagc ctctacaact gca                                             23

<210> SEQ ID NO 25
<211> LENGTH: 22
<212> TYPE: DNA
<213> ORGANISM: Artificial
<220> FEATURE:
<223> OTHER INFORMATION: Based on the hybrid NRPS-PKS ndaC (AAO64404)
     within the ndaS gene cluster

<400> SEQUENCE: 25
ggatccgcca ggagaacggc gg                                              22

<210> SEQ ID NO 26
<211> LENGTH: 22
<212> TYPE: DNA
<213> ORGANISM: Artificial
<220> FEATURE:
<223> OTHER INFORMATION: Based on the hybrid NRPS-PKS ndaC (AAO64404)
     sequence within the ndaS gene cluster

<400> SEQUENCE: 26
ggagctcttt tccaaacatt ct                                              22

<210> SEQ ID NO 27
<211> LENGTH: 26
<212> TYPE: DNA
<213> ORGANISM: Artificial
<220> FEATURE:
<223> OTHER INFORMATION: Based on hybrid NRPS-PKS ndaC (AAO64404)
     sequence within the ndaS gene cluster

<400> SEQUENCE: 27
gggatcctct aagcattcca tcagtc                                          26

<210> SEQ ID NO 28
<211> LENGTH: 20
<212> TYPE: DNA
<213> ORGANISM: Artificial
<220> FEATURE:

<223> OTHER INFORMATION: Based on Synechocystis sp. fatty acid synthesis
     acyl carrier sequence

<400> SEQUENCE: 28
gcatatgaat caggaaattt                                                  20

<210> SEQ ID NO 29
<211> LENGTH: 31
<212> TYPE: DNA
<213> ORGANISM: Artificial
<220> FEATURE:
<223> OTHER INFORMATION: Based on Synechocystis sp. fatty acid synthesis
     acyl carrier sequence

<400> SEQUENCE: 29
cctcgagtaa tttactttcg atatgctcaa c                                     31

<210> SEQ ID NO 30
<211> LENGTH: 16
<212> TYPE: DNA
<213> ORGANISM: Artificial
<220> FEATURE:
<223> OTHER INFORMATION: Based on Microcystis aeruginosa PCP sequence

<400> SEQUENCE: 30
ggatcctgaa caggga                                                      16

<210> SEQ ID NO 31
<211> LENGTH: 20
<212> TYPE: DNA
<213> ORGANISM: Artificial
<220> FEATURE:
<223> OTHER INFORMATION: Based on Microcystis aeruginosa PCP sequence

<400> SEQUENCE: 31
ctcgagatgg cgacggctcc                                                  20

<210> SEQ ID NO 32
<211> LENGTH: 21
<212> TYPE: DNA
<213> ORGANISM: Artificial
<220> FEATURE:
<223> OTHER INFORMATION: Based on Nostoc punctiforme NSOR10 NRPS PCP
     sequence

<400> SEQUENCE: 32
ggatcctaaa atctaggcta g                                                21

<210> SEQ ID NO 33
<211> LENGTH: 21
<212> TYPE: DNA
<213> ORGANISM: Artificial
<220> FEATURE:
<223> OTHER INFORMATION: Based on Nostoc punctiforme NSOR10 NRPS PCP
     sequence

<400> SEQUENCE: 33
gagctcaaat tgttatttct t                                                21

<210> SEQ ID NO 34
<211> LENGTH: 24
<212> TYPE: DNA
<213> ORGANISM: Artificial
<220> FEATURE:
<223> OTHER INFORMATION: Based on Nodularia spumigena NPPT sequence

<400> SEQUENCE: 34

```
tgcatatgac ggcgcttaat catt                                          24
```

<210> SEQ ID NO 35
<211> LENGTH: 23
<212> TYPE: DNA
<213> ORGANISM: Artificial
<220> FEATURE:
<223> OTHER INFORMATION: Based on Nodularia spumigena NPPT sequence

<400> SEQUENCE: 35

```
tctcgagtca gtattgccaa cac                                           23
```

<210> SEQ ID NO 36
<211> LENGTH: 26
<212> TYPE: DNA
<213> ORGANISM: Artificial
<220> FEATURE:
<223> OTHER INFORMATION: Based on nitrate inducible promoter PnirA from
      Synechococcus sp. strain PCC7942

<400> SEQUENCE: 36

```
ttctagatcc ctctcagatc aaaaag                                        26
```

<210> SEQ ID NO 37
<211> LENGTH: 24
<212> TYPE: DNA
<213> ORGANISM: Artificial
<220> FEATURE:
<223> OTHER INFORMATION: Based on nitrate inducible promoter PnirA
      sequence from Synechococcus sp. strain PCC7942

<400> SEQUENCE: 37

```
tgcatatggg attcatctgc ctac                                          24
```

<210> SEQ ID NO 38
<211> LENGTH: 155
<212> TYPE: PRT
<213> ORGANISM: Pseudomonas aeruginosa

<400> SEQUENCE: 38

Phe Asp Pro Ala Leu Leu Gln Pro Gly Asp Phe Ala Leu Ala Gly Ile
1               5                   10                  15

Gln Pro Pro Ala Asn Ile Leu Arg Ala Val Ala Lys Arg Gln Ala Glu
            20                  25                  30

Phe Leu Ala Gly Arg Leu Cys Ala Arg Ala Ala Leu Phe Ala Leu Asp
        35                  40                  45

Gly Arg Ala Gln Thr Pro Ala Val Gly Glu Asp Arg Ala Pro Val Trp
    50                  55                  60

Pro Ala Ala Ile Ser Gly Ser Ile Thr His Gly Asp Arg Trp Ala Ala
65                  70                  75                  80

Ala Leu Val Ala Ala Arg Gly Asp Trp Arg Gly Leu Gly Leu Asp Val
                85                  90                  95

Glu Thr Leu Leu Glu Ala Glu Arg Ala Arg Tyr Leu His Gly Glu Ile
            100                 105                 110

Leu Thr Glu Gly Glu Arg Leu Arg Phe Ala Asp Asp Leu Glu Arg Arg
        115                 120                 125

Thr Gly Leu Leu Val Thr Leu Ala Phe Ser Leu Lys Glu Ser Leu Phe
    130                 135                 140

Lys Ala Leu Tyr Pro Leu Val Gly Lys Arg Phe
145                 150                 155

<210> SEQ ID NO 39
<211> LENGTH: 160
<212> TYPE: PRT
<213> ORGANISM: Xanthomonas albicans

<400> SEQUENCE: 39

```
Phe Asp Thr Ala Gln Phe Asp Pro Gly Ala Phe Ala Ala Met Ala Ile
1               5                   10                  15

Ala Arg Pro Asp Ser Ile Ala Arg Ser Val Arg Lys Arg Gln Ala Glu
            20                  25                  30

Phe Leu Phe Gly Arg Leu Ala Ala Arg Leu Ala Leu Gln Glu Val Leu
        35                  40                  45

Gly Pro Ala Gln Ala Gln Ala Asp Ile Ala Ile Gly Ala Thr Arg Ala
    50                  55                  60

Pro Cys Trp Pro Ala Gly Ser Leu Gly Ser Ile Ser His Cys Glu Asp
65                  70                  75                  80

Tyr Ala Ala Ala Ile Ala Met Ala Ala Gly Thr Arg His Gly Val Gly
                85                  90                  95

Ile Asp Leu Glu Arg Pro Ile Thr Pro Ala Arg Ala Ala Leu Leu
            100                 105                 110

Ser Ile Ala Ile Asp Ala Asp Glu Ala Ala Arg Leu Ala Lys Ala Ala
        115                 120                 125

Asp Ala Gln Trp Pro Gly Asp Leu Leu Leu Thr Ala Leu Phe Ser Ala
    130                 135                 140

Lys Glu Ser Leu Phe Lys Ala Ala Tyr Ser Ala Val Gly Arg Tyr Phe
145                 150                 155                 160
```

<210> SEQ ID NO 40
<211> LENGTH: 153
<212> TYPE: PRT
<213> ORGANISM: Vibrio cholerae

<400> SEQUENCE: 40

```
Phe Asp Pro Gln Gln Phe Asp Glu Asp Gln Gln His Tyr Leu Ala Pro
1               5                   10                  15

Pro Thr Tyr His Ser Leu His Lys Ala Val Lys Arg Gln Ala Glu
            20                  25                  30

Phe Val Ala Gly Arg Lys Leu Ala Gln Gln Ala Leu Lys Gln Ile Gly
        35                  40                  45

Gln Gly Tyr Asp Arg Pro Ile Ala Ile Gly Thr His Arg Glu Pro Leu
    50                  55                  60

Trp Pro Ala Gly Ile Thr Gly Ser Ile Ala His Cys Asp Gly Trp Ala
65                  70                  75                  80

Val Cys Thr Val Leu Lys Ala Glu His Leu Ser Leu Gly Ile Asp Ile
                85                  90                  95

Glu His Arg Leu Ala His Gln Thr Ala Ser Glu Val Gln Ala Ile Ile
            100                 105                 110

Gly Thr Ala Gln Glu Trp Ala Leu Leu Ala Gln Gln Phe Asp Leu Ala
        115                 120                 125

Ser Ala Val Thr Leu Leu Phe Ser Ala Lys Glu Ser Leu Phe Lys Ala
    130                 135                 140

Leu Phe Pro Gln Val His Leu Tyr Leu
145                 150
```

<210> SEQ ID NO 41
<211> LENGTH: 154

-continued

<212> TYPE: PRT
<213> ORGANISM: Photorhabdus luminescens

<400> SEQUENCE: 41

Phe Asp Leu Ser His Tyr His Asp Glu Leu Phe Glu Gln Leu Asn Leu
1               5                   10                  15

Pro Phe Pro Ala Thr Leu Ala Lys Ala Val Asn Lys Arg Arg Ala Glu
            20                  25                  30

Tyr Leu Ala Ala Arg Tyr Cys Ala Arg Gln Leu Leu Ala Gln Leu Gly
        35                  40                  45

Gln Pro Glu Phe Asn Leu Leu Ser Gly His Asp Arg Ala Pro Ile Trp
    50                  55                  60

Pro Lys Asp Ile Cys Gly Ser Val Ser His Ser His Cys Ala Ile
65                  70                  75                  80

Val Leu Ala Ala Pro Gln Thr Asp Asn Arg Leu Ile Gly Val Asp Ile
                85                  90                  95

Glu Ala Ile Val Asn Arg Gln Asn Met Asp Glu Ile Thr Lys Met Ile
            100                 105                 110

Val Asn Asp Arg Glu Ile Gln Leu Leu Lys His Cys His Leu Pro Phe
        115                 120                 125

Glu Gln Ala Phe Thr Leu Ala Phe Ser Val Lys Glu Ser Leu Tyr Lys
    130                 135                 140

Ala Leu Tyr Pro Gln Ile Lys Arg Ser Leu
145                 150

<210> SEQ ID NO 42
<211> LENGTH: 146
<212> TYPE: PRT
<213> ORGANISM: Bacillus subtilis

<400> SEQUENCE: 42

Phe Met Thr Phe Ile Ser Pro Glu Lys Arg Glu Lys Cys Arg Arg Phe
1               5                   10                  15

Tyr His Lys Glu Asp Ala His Arg Thr Leu Leu Gly Asp Val Leu Val
            20                  25                  30

Arg Ser Val Ile Ser Arg Gln Tyr Gln Leu Asp Lys Ser Asp Ile Arg
        35                  40                  45

Phe Ser Thr Gln Glu Tyr Gly Lys Pro Cys Ile Pro Asp Leu Pro Asp
    50                  55                  60

Ala His Phe Asn Ile Ser His Ser Gly Arg Trp Val Ile Cys Ala Phe
65                  70                  75                  80

Asp Ser Gln Pro Ile Gly Ile Asp Ile Glu Lys Thr Lys Pro Ile Ser
                85                  90                  95

Leu Glu Ile Ala Lys Arg Phe Phe Ser Lys Thr Glu Tyr Ser Asp Leu
            100                 105                 110

Leu Ala Lys Asp Lys Asp Glu Gln Thr Asp Tyr Phe Tyr His Leu Trp
        115                 120                 125

Ser Met Lys Glu Ser Phe Ile Lys Gln Glu Gly Lys Gly Leu Ser Leu
    130                 135                 140

Pro Leu
145

<210> SEQ ID NO 43
<211> LENGTH: 151
<212> TYPE: PRT
<213> ORGANISM: Synechocystis PCC6803

```
<400> SEQUENCE: 43

Tyr Gln Ala Leu Leu Ser Ser Glu Glu Met Ala Arg Gly Glu Arg Tyr
1               5                   10                  15

Gln Arg Pro Gln Asp Lys Gln Arg Phe Leu Thr Met Arg Leu Ala Leu
            20                  25                  30

Arg Ile Leu Leu Ala Arg Gln Leu Asp Cys Leu Pro Gln Gln Leu Gln
        35                  40                  45

Phe Thr Tyr Gly Pro Gln Gly Lys Pro Glu Leu Val Asp Arg Glu Arg
    50                  55                  60

Arg Ser Pro Trp Phe Asn Val Ala His Ser Gly Asn Tyr Gly Leu Ile
65                  70                  75                  80

Gly Leu Ser Thr Glu Gly Ile Gly Val Asp Leu Gln Ile Met Leu
                85                  90                  95

Pro Lys Pro His Tyr Leu Lys Leu Ala Lys Arg Phe Phe Ala Pro Gln
            100                 105                 110

Glu Val Gln Gln Leu Glu Ser Leu Glu Gly Lys Arg Thr Lys Leu
        115                 120                 125

Phe Tyr Gln Leu Trp Thr Ala Lys Glu Ala Phe Leu Lys Ala Thr Gly
    130                 135                 140

Lys Gly Ile Ser Gly Gly Leu
145                 150

<210> SEQ ID NO 44
<211> LENGTH: 158
<212> TYPE: PRT
<213> ORGANISM: Caenorhabdus elegans

<400> SEQUENCE: 44

Ala Val Gln Ser Ile Thr Glu Glu Phe Gln Arg Ile Pro Glu Phe
1               5                   10                  15

Arg His Arg Glu Asp Ala Leu Ala Cys Leu Phe Gly Arg Leu Leu Leu
            20                  25                  30

Arg His Ser Ala Gln Lys Phe Ser Gly Glu Pro Trp Asn Thr Ile Arg
        35                  40                  45

Phe Glu Arg Thr Glu Arg Gly Lys Pro Phe Leu Ala Val Pro Ala Asp
    50                  55                  60

Thr Thr Phe Gly Leu Asn Val Ser His Gln Gly Asp Tyr Val Ala Phe
65                  70                  75                  80

Ala Ser Ser Cys Ser Ser Lys Val Gly Val Asp Val Met Arg Leu Asp
                85                  90                  95

Asn Glu Arg Asn Asn Lys Thr Ala Asp Glu Tyr Ile Asn Ser Met Ala
            100                 105                 110

Lys Ser Ala Ser Pro Glu Glu Leu Arg Met Met Arg Ser Gln Pro Thr
        115                 120                 125

Glu Ala Met Lys Met Thr Met Phe Tyr Arg Tyr Trp Cys Leu Lys Glu
    130                 135                 140

Ala Ile Leu Lys Ala Thr Gly Val Gly Ile Met Lys Asp Leu
145                 150                 155

<210> SEQ ID NO 45
<211> LENGTH: 167
<212> TYPE: PRT
<213> ORGANISM: Drosphilia melanogaster

<400> SEQUENCE: 45

Ala Val Ala Ser Ile Gln Pro Glu Glu Arg Ala Arg Leu Met Lys Phe
```

```
1               5                   10                  15
His Phe Ile Asp Asp Phe Leu Ser Ser Leu Ile Gly Arg Leu Phe Met
                20                  25                  30

Arg Lys Tyr Val Ser Thr Cys Ser Gly Leu Pro Ser Ala Glu Val Lys
                35                  40                  45

Phe Ala Arg Asp Val Arg Gly Lys Pro Tyr Trp Val Lys Gly Glu Asp
            50                  55                  60

Tyr Asp Gly Pro Pro Leu Ser Phe Asn Val Ser His Gln Gly Ser Leu
65                  70                  75                  80

Val Leu Leu Ala Gly Ile Ala Gly Glu Ser Ser Asp Pro Asp Phe Gly
                85                  90                  95

Ile Gly Thr Asp Val Met Lys Ile Glu Tyr Asn Gly Gly Lys Pro Leu
                100                 105                 110

Ser Glu Phe Phe Gly Leu Met Lys Ser Lys Phe Ser Ala Glu Glu Trp
                115                 120                 125

Ser Tyr Ile Gly Arg Pro His His Asp Glu Arg Glu Gln Val Lys Ala
                130                 135                 140

Phe Met Arg His Trp Cys Leu Lys Glu Ala Tyr Val Lys Glu Leu Gly
145                 150                 155                 160

Val Gly Ile Thr Val Asp Leu
                165

<210> SEQ ID NO 46
<211> LENGTH: 83
<212> TYPE: PRT
<213> ORGANISM: Artificial Sequence
<220> FEATURE:
<223> OTHER INFORMATION: Consensus sequence

<400> SEQUENCE: 46

Phe Asp Pro Val Lys Arg Ala Glu Phe Leu Gly Arg Ala Ala Leu Leu
1               5                   10                  15

Leu Glu Glu Asp Arg Arg Ile Arg Phe Gly Arg Ala Pro Trp Pro Ala
                20                  25                  30

Gly Ser Ile His Ala Gly Asp Glu Gly Lys Pro Ser His Gly Ala Gly
                35                  40                  45

Asp Lys Ile Glu Leu Asp Thr Leu Phe Ser Lys Glu Ser Leu Phe Lys
                50                  55                  60

Ala Leu Tyr Pro Val Leu Glu Leu Glu Phe Trp Lys Glu Ala Lys Gly
65                  70                  75                  80

Gly Ile Leu

<210> SEQ ID NO 47
<211> LENGTH: 237
<212> TYPE: PRT
<213> ORGANISM: Nodularia spumigena NSOR10

<400> SEQUENCE: 47

Met Leu Gln His Thr Trp Leu Pro Lys Pro Asn Leu Thr Leu Leu
1               5                   10                  15

Ser Asp Glu Val His Leu Trp Arg Ile Pro Leu Asp Gln Pro Glu Ser
                20                  25                  30

Gln Leu Gln Asp Leu Ala Ala Thr Leu Ser Ser Asp Glu Leu Ala Arg
                35                  40                  45

Ala Asn Arg Phe Tyr Phe Pro Glu His Arg Arg Arg Phe Thr Ala Gly
                50                  55                  60
```

```
Arg Gly Ile Leu Arg Ser Ile Leu Gly Gly Tyr Leu Gly Val Glu Pro
 65                  70                  75                  80

Gly Gln Val Lys Phe Asp Tyr Glu Ser Arg Gly Lys Pro Ile Leu Gly
                 85                  90                  95

Asp Arg Phe Ala Glu Ser Gly Leu Leu Phe Asn Leu Ser His Ser Gln
            100                 105                 110

Asn Leu Ala Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
            180                 185                 190

Ala Leu Thr Pro Thr Glu Pro Ala Lys Leu Gln Thr Ala Pro Ala Trp
        195                 200                 205

Ser Leu Leu Glu Leu Val Pro Asp Asp Asn Cys Val Ala Ala Val Ala
    210                 215                 220

Val Ala Gly Phe Gly Trp Gln Pro Lys Phe Trp His Tyr
225                 230                 235

<210> SEQ ID NO 48
<211> LENGTH: 246
<212> TYPE: PRT
<213> ORGANISM: Synechocystis sp. PCC 6803

<400> SEQUENCE: 48

Met Leu Pro Gln Pro Gln Ile Trp Leu Cys Pro Thr Asp Arg Pro Leu
  1               5                  10                  15

Ile Pro Gly Tyr Gln Ala Leu Leu Ser Ser Glu Glu Met Ala Arg Gly
                 20                  25                  30

Glu Arg Tyr Gln Arg Pro Gln Asp Lys Gln Arg Phe Leu Thr Met Arg
            35                  40                  45

Leu Ala Leu Arg Ile Leu Leu Ala Arg Gln Leu Asp Cys Leu Pro Gln
 50                  55                  60

Gln Leu Gln Phe Thr Tyr Gly Pro Gln Gly Lys Pro Glu Leu Val Asp
 65                  70                  75                  80

Arg Glu Arg Arg Ser Pro Trp Phe Asn Val Ala His Ser Gly Asn Tyr
                 85                  90                  95

Gly Leu Ile Gly Leu Ser Thr Glu Gly Glu Ile Gly Val Asp Leu Gln
            100                 105                 110

Ile Met Leu Pro Lys Pro His Tyr Leu Lys Leu Ala Lys Arg Phe Phe
        115                 120                 125

Ala Pro Gln Glu Val Gln Gln Leu Glu Ser Leu Glu Gly Glu Lys Arg
    130                 135                 140

Thr Lys Leu Phe Tyr Gln Leu Trp Thr Ala Lys Glu Ala Phe Leu Lys
145                 150                 155                 160

Ala Thr Gly Lys Gly Ile Ser Gly Gly Leu Asn Gln Val Ile Pro Asp
                165                 170                 175

Glu Asn Leu Ala Lys Tyr Gln Tyr Leu Pro Asp Ser Gly Asp Thr Asn
            180                 185                 190

His Trp Arg Leu Ser Ser Gln Pro Leu Leu Ala Asp Gln Gly Ser Asn
        195                 200                 205
```

Asp Asn Tyr Trp Met Ala Ile Ala Trp Cys Thr Asn Glu Val Asn Gln
                210                 215                 220

Val Glu Ser Asn Tyr Leu Pro Asn Ile Gln Pro Phe Gln Trp Pro Arg
225                 230                 235                 240

Asn Leu Asp Ser Leu Pro
                245

<210> SEQ ID NO 49
<211> LENGTH: 214
<212> TYPE: PRT
<213> ORGANISM: Bacillus subtilis P39135

<400> SEQUENCE: 49

Met Cys Leu Ser Ser Asn Val Asn Gln His Asn Asp Thr Thr Val Val
1               5                   10                  15

Val Gly Thr Ile Ser Ser Leu His Ser Arg Lys Glu Leu Tyr Ser
            20                  25                  30

Tyr Leu Ser Ser Asp Glu Arg Gln Arg Ala Glu Arg Met Lys Ser Ser
            35                  40                  45

Val Tyr Ala Glu Arg Phe Lys Leu Ile Arg Gly Tyr Leu Arg Phe Leu
50                  55                  60

Leu Ser Thr Val Leu Ala Leu Pro Pro Asn Gln Ile His Phe Thr Tyr
65                  70                  75                  80

Gly Lys Tyr Gly Lys Pro Ile Val Glu Asn Asn Asp Tyr Phe Phe Asn
                85                  90                  95

Val Ser His Ala Lys Asp Tyr Phe Leu Ile Gly Leu His Glu Thr Ala
            100                 105                 110

Val Leu Gly Val Asp Ile Glu Cys Pro Arg Pro Phe Pro Pro Lys Val
            115                 120                 125

His Pro Phe Phe Phe His Gln Asp Glu Ile Asn Leu Leu Ala Ser Val
130                 135                 140

Asp Pro Asp Gln Lys Met Arg Leu Trp Leu Ser Leu Trp Thr Arg Lys
145                 150                 155                 160

Glu Ala Leu Gly Lys Ala Val Gly Glu Gly Leu Ser Ser Asn Ile Gly
                165                 170                 175

Lys Gln Ser Val Leu Ser Asp Thr Ile His Tyr Asn Gly Arg Glu Tyr
            180                 185                 190

Val Leu Leu Thr Gln His Asp Pro Ser Tyr Val Lys Thr Ile Cys Leu
            195                 200                 205

Glu Gly Lys Ser Val Gln
            210

<210> SEQ ID NO 50
<211> LENGTH: 141
<212> TYPE: DNA
<213> ORGANISM: Anabaena cylindrica PCC 7122

<400> SEQUENCE: 50
aattggggta gatttggaat atattcgccc tatgtcggat gtagaaagtc ttgctaaacg      60
cttcttttta ccaaaagaat atgacgtaat aaaattactc tctcccgaac aacaacaaca    120 ggtattttt cgttactgga c                                               141

<210> SEQ ID NO 51
<211> LENGTH: 237
<212> TYPE: PRT
<213> ORGANISM: Anabaena variabilis ATCC 29413

<400> SEQUENCE: 51

```
Met Leu Gln His Thr Trp Leu Pro Lys Pro Asn Leu Thr Leu Leu
1               5                   10                  15

Ser Asp Glu Val His Leu Trp Arg Ile Pro Leu Asp Arg Pro Glu Ser
            20                  25                  30

Gln Leu Gln His Leu Ala Ala Thr Leu Ser Ser Asp Glu Leu Ala Arg
        35                  40                  45

Ala Asn Arg Phe Tyr Phe Pro Glu His Arg Gln Arg Phe Thr Ala Gly
    50                  55                  60

Arg Gly Ile Leu Arg Ser Ile Leu Gly Leu Tyr Leu Gly Val Glu Pro
65                  70                  75                  80

Lys Gln Val Lys Phe Glu Tyr Glu Ser Arg Gly Lys Pro Val Leu Gly
                85                  90                  95

Asp Arg Phe Ala Asp Ser Gly Leu Leu Phe Asn Leu Ser His Ser Gln
            100                 105                 110

Asn Leu Gly Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
            180                 185                 190

Ala Leu Thr Pro Thr Glu Pro Ala Lys Leu Gln Thr Thr Pro Ala Trp
        195                 200                 205

Ser Leu Leu Glu Leu Val Pro Asp Asp Asn Cys Val Ala Ala Val Ala
    210                 215                 220

Val Ala Gly Phe Gly Trp Gln Pro Lys Phe Trp Gln Tyr
225                 230                 235
```

<210> SEQ ID NO 52
<211> LENGTH: 251
<212> TYPE: PRT
<213> ORGANISM: Crocosphaera watsonii WH 8501

<400> SEQUENCE: 52

```
Met Leu Thr Trp Tyr Lys Lys Tyr Gln Ile Met Asn Ile Thr Trp Lys
1               5                   10                  15

Tyr Pro Pro Lys Asn Leu Thr Ile Asn Ala Thr Glu Ile His Ile Trp
            20                  25                  30

Lys Thr His Leu Glu Gln Ser Ala Ile Asp Phe Lys Ser Phe Asp
        35                  40                  45

Ile Leu Asn Glu Glu Lys Ile Lys Ala Gln Arg Phe Arg Phe Glu
    50                  55                  60

Lys His Gln Gln Arg Phe Thr Ile Ala Arg Ser Ser Leu Arg Arg Ile
65                  70                  75                  80

Leu Ser Leu Tyr Leu Trp Ile Ser Pro Gln Lys Ile Asp Phe Gln Tyr
                85                  90                  95

Asn Ala Tyr Gly Lys Pro Gln Leu Leu Asp Asn Ile Asn Lys Ile Asn
            100                 105                 110

Leu Gln Phe Asn Val Ser His Ser Glu Asn Ile Ala Ile Tyr Gly Ile
        115                 120                 125
```

Thr Cys His Asn Leu Ile Gly Val Asp Ile Glu Tyr Met Arg Pro Met
            130                 135                 140

Ala Glu Ala Glu Asn Leu Ala Lys Arg Phe Phe Ser Gln Lys Glu Phe
145                 150                 155                 160

Glu Gln Ile Ser Lys Leu Pro Ser Ala Glu Gln Asp Arg Glu Phe Phe
                165                 170                 175

Gln Leu Trp Thr Gly Lys Glu Ala Tyr Leu Lys Ala Ile Gly Lys Gly
            180                 185                 190

Ile Ser Gly Gly Leu Glu Lys Val Glu Ile Ser Pro His Glu Pro Arg
        195                 200                 205

Lys Phe Ile Arg Leu Pro Glu Ser Asn Pro Asn Tyr Asn Leu Val
210                 215                 220

Tyr Leu Thr Pro Glu Asn Asn Tyr Leu Ala Ala Ile Ala Val Glu Asn
225                 230                 235                 240

Lys Gln Gln Asn Tyr Gln Tyr Trp Gln Leu Asn
                245                 250

<210> SEQ ID NO 53
<211> LENGTH: 163
<212> TYPE: DNA
<213> ORGANISM: Cylindrospermum sp. CENA33
<220> FEATURE:
<221> NAME/KEY: misc_feature
<222> LOCATION: (93)..(93)
<223> OTHER INFORMATION: n is a, c, g, or t

<400> SEQUENCE: 53
tgggcgccaa attggggtag acctggagtg tattcgcccg gtgtctgatt tggaatccct      60
ggcagagcgg ttcttttttgc ctagagaatc tgntatggtg cgatcgcttc ccacaaatca    120
acaacaagaa gttttcttcc gttattggac atctaaagag gca                        163

<210> SEQ ID NO 54
<211> LENGTH: 255
<212> TYPE: PRT
<213> ORGANISM: Gloeobacter violaceus PCC 7421

<400> SEQUENCE: 54

Met Val Ala Ile Glu Ala Pro Trp Arg Pro Thr Ala Ala Pro Pro Val
1               5                   10                  15

Leu Thr Pro Ala Ala Val His Ile Trp Gln Ala Asp Leu Asp Trp Pro
            20                  25                  30

Ala Ala Pro Leu Pro Val Leu Glu Arg Thr Leu Cys Pro Gln Glu Arg
        35                  40                  45

Ser Arg Ala Glu Arg Phe Cys Phe Glu Gln His Arg Arg Phe Ile
    50                  55                  60

Val Gly Arg Ala Thr Leu Arg Met Leu Leu Gly Leu Tyr Leu Gln Ser
65                  70                  75                  80

Glu Pro Ala Cys Val Pro Ile Ser Tyr Gly Ala His Gly Lys Pro Leu
                85                  90                  95

Leu Ala Asp Gly Ala His Pro Leu Arg Phe Asn Leu Ser His Ser Gln
            100                 105                 110

Gly Lys Ala Val Tyr Ala Phe Ser Cys Gly Arg Glu Val Gly Val Asp
        115                 120                 125

Leu Glu Trp Asp Arg Pro Leu Ala Asn Phe Asp Gln Leu Ala Arg Val
    130                 135                 140

Ala Phe Ser Glu Asp Glu Asn Arg Val Phe Lys Ala Leu Ala Pro Tyr 145             150             155             160
Gln Arg Arg Ala Ala Phe Phe Arg Cys Trp Thr Arg Lys Glu Ala Tyr
                165                 170                 175

Ala Lys Ala Arg Gly Tyr Gly Phe Ala Leu Ala Pro Asp Arg Tyr Thr
                180                 185                 190

Val Ser Leu Ala Pro Asp Ala Pro Ala Leu Leu Gln Ser Arg Glu
                195                 200                 205

Glu Ser Gly Glu Ala Gly Arg Trp Val Leu Leu Asp Leu Leu Pro Trp
        210                 215                 220

Pro Asp Tyr Pro Ala Ala Leu Ala Val Glu Gly Ser Ser Gly Gln Val
225                 230                 235                 240

His Cys Trp His Ser Pro Glu Pro Ile Ser Arg Arg Ser Pro Arg
                    245                 250                 255

<210> SEQ ID NO 55
<211> LENGTH: 1625
<212> TYPE: PRT
<213> ORGANISM: Gloeobacter violaceus PCC 7421

<400> SEQUENCE: 55

Met Pro Met Asn Pro Ile Glu Pro Val Ala Ile Val Gly Met Ala Ala
1               5                   10                  15

Leu Phe Pro Lys Ala Ala Thr Val Gly Asp Phe Trp Gln Asn Ile Val
                20                  25                  30

Asp Lys Val Asp Ala Val Ser Glu Ala Pro Ala Ser Trp Ala Arg His
            35                  40                  45

Tyr Phe Asp Pro Asn Ser Lys Glu Gln Asp Arg Ile Tyr Thr Ser Lys
        50                  55                  60

Gly Gly Phe Leu Gly Glu Leu Ala Glu Phe Asp Pro Thr Glu Phe Gly
65                  70                  75                  80

Ile Met Pro Asn Thr Leu Asp Ala Ala Glu Pro Asp His Phe Ile Ala
                85                  90                  95

Leu Lys Leu Ala Arg Asp Ala Leu Ala Asp Ala Gly Tyr Leu Asp Arg
            100                 105                 110

Pro Phe Asn Arg Lys Lys Ala Gly Ile Ile Leu Gly His Gly Val Tyr
        115                 120                 125

Val Asn Arg Gly His Met Ala Met Leu Gln Gln Thr Leu Val Leu Asp
130                 135                 140

Gln Thr Met Asp Thr Leu Arg Arg Val Cys Pro Glu Leu Gly Glu Glu
145                 150                 155                 160

Ala Leu Ala Ala Val His Arg Ala Leu Arg Lys Ser Ala Pro Ala Phe
                165                 170                 175

Asn Ala Glu Val Val Pro Gly Met Val Pro Asn Val Ile Thr Gly Arg
            180                 185                 190

Ile Ala Asn Arg Leu Asp Leu Met Gly Pro Asn Tyr Leu Val Asp Ala
        195                 200                 205

Ala Cys Ala Ser Gly Leu Ile Val Val Glu Leu Ala Met Lys Glu Leu
    210                 215                 220

Ala Ser Gly Arg Cys Asp Leu Val Leu Ala Gly Gly Val Gln Ala Ser
225                 230                 235                 240

Leu Pro Pro Gln Tyr Asn Met Ala Phe Cys Gln Leu Gly Ala Leu Ser
                245                 250                 255

Arg Thr Asn Ile Arg Pro Phe Asp Arg Ala Ala Asp Gly Asn Val Met
            260                 265                 270

-continued

Gly Glu Gly Cys Gly Ile Leu Val Leu Lys Arg Leu Ala Asp Ala Glu
            275                 280                 285

Leu Asp Gly Asp Arg Ile Tyr Ala Val Val Arg Gly Val Gly Ser Ser
290                 295                 300

Ser Asn Gly Lys Ala Leu Gly Met Leu Ala Pro Arg Leu Glu Gly Glu
305                 310                 315                 320

Val Leu Ala Leu Glu Glu Ala Tyr Ser Leu Thr Gly Ile Asp Pro Ala
            325                 330                 335

Ser Val Asp Leu Val Glu Ala His Gly Thr Gly Ile Pro Val Gly Asp
            340                 345                 350

Arg Thr Glu Met Glu Ala Leu Ala Gln Val Tyr Gly Ala Arg Glu Gly
            355                 360                 365

Asp Leu Pro Arg Val Gly Met Gly Ser Val Lys Ser Met Ile Gly His
370                 375                 380

Cys Ile Pro Ala Ser Gly Ala Ala Ser Phe Ile Lys Met Ala Leu Ala
385                 390                 395                 400

Leu Tyr His Lys Val Leu Pro Pro Thr Leu Leu Asp Ala Val Asn Pro
            405                 410                 415

Glu Leu Gly Val Glu Lys Thr Pro Phe Tyr Leu Asn Asn Ala Thr Arg
            420                 425                 430

Pro Trp Val Ser Ala Asn Gln Arg Pro Arg Ala Gly Ile Asn Ala
            435                 440                 445

Phe Gly Phe Gly Gly Ile Asn Ala His Ala Ile Leu Glu Glu His Thr
            450                 455                 460

Pro Thr Gly Pro Asp Thr Val Leu His Arg Arg Trp Pro Ser Glu Leu
465                 470                 475                 480

Val Val Phe Ala Ala Asp Asp Arg Pro Gly Leu Ile Ala Lys Ile Glu
            485                 490                 495

Arg Thr Leu Val Val His Pro Thr Leu Pro Leu Ala Gln Ile Ala Cys
            500                 505                 510

Asn Gln Ala Ala Gly Thr Ala Gly Asp Tyr Arg Leu Ala Val Val Ala
            515                 520                 525

Lys Asp Arg Ala Asp Leu His Lys Lys Leu Arg Gln Ala Val Glu Lys
530                 535                 540

Leu Lys Glu Pro Gly Arg Val Arg Leu Arg Gly Gly Val Met Tyr Gly
545                 550                 555                 560

Glu Val Thr Ser Glu Met Ala Asp Ala Gln Thr Ala Met Ile Phe Pro
            565                 570                 575

Gly Glu Gly Cys Gln Tyr Pro Asn Met Leu Ala Asp Leu Cys Leu His
            580                 585                 590

Phe Pro Val Val Arg Glu Trp Phe Asp Phe Leu Asp Ser Ala Leu Gly
            595                 600                 605

Ala Asp Arg Pro His Pro Pro Ser Arg Tyr Ile Phe Pro Pro Thr
610                 615                 620

Ala Ile Asp Glu Gln Val Gln Glu Gln Thr His Arg Ala Ile Tyr Gln
625                 630                 635                 640

Met Glu Leu Ala Val Ala Ser Val Ala Thr Ala Ser Met Ala Leu Tyr
            645                 650                 655

Glu Leu Leu Gln Gln Phe Glu Ile Lys Ala Asp Val Met Val Gly His
            660                 665                 670

Ser Thr Gly Glu Leu Thr Ser Leu Val Ala Ser Gly Val Val Arg Leu
            675                 680                 685

Thr Asp Arg Ser Gln Met Met Glu Lys Leu Leu Leu Leu Asn Gly Leu

-continued

```
                690              695              700

Tyr Gln Arg Leu Glu Gln Met Asn Ile Val Pro Arg Gly Ala Leu Leu
705                  710              715                  720

Ala Val Gly Ala Val Lys Ser Asp Asp Leu Gln Gln Val Leu Ala Asp
                725              730                  735

Leu Glu Gly Arg Leu His Leu Ala Met Asp Asn Cys Pro Asn Gln Val
                740              745              750

Val Leu Phe Gly Asp Glu Gln Ala Val Thr Gln Ala Ser Glu Arg Leu
            755              760              765

Gln Ala Ser Gly Ala Ile Cys Ser Arg Leu Pro Phe Asp Arg Ala Tyr
770              775              780

His Thr Pro Leu Phe Glu Ala Gly Lys Val Leu Arg Gly Phe Tyr
785              790              795              800

Asp Ala Leu Asp Val Gly Pro Gly His Thr Pro Leu Phe Ser Cys Ala
                805              810              815

Ser Val Gly Leu Phe Pro Asp Asp Pro Glu Gly Ile Arg Thr Leu Gly
            820              825              830

Glu Arg Gln Trp Pro Ser Arg Val Arg Phe Arg Glu Thr Leu Glu Thr
        835              840              845

Leu Tyr Ser Gln Gly Val Arg His Phe Val Glu Val Gly Pro Ser Gly
850              855              860

Asn Leu Thr Gly Phe Val Asp Asp Val Leu Lys Gly Arg Asp Tyr Lys
865              870              875              880

Ala Val Pro Val Asn Ser Gln Arg Lys Ser Gly Leu Glu Gln Leu Gln
                885              890              895

His Leu Val Gly Gln Leu Phe Val Ser Gly Lys His Val Ser Phe Ala
            900              905              910

Pro Phe Tyr Ser Arg Arg Gly Leu Leu Pro Gln Pro Ala Pro Gly
        915              920              925

Glu Ala Gln Pro Lys Arg Arg Gly Arg Val Leu Asp Leu Thr Leu Pro
        930              935              940

His Met Glu Leu Pro Pro Asp Phe Val Leu Pro Glu Arg Gln Ala Pro
945              950              955              960

Ala Val Pro Val Pro Ala Pro Lys Ala Thr Thr Asn Gly Ser His Pro
                965              970              975

Pro Ser Leu Thr Ser Leu Thr Ala Ala Pro Ala Pro Val Ser Thr Leu
            980              985              990

Ala Pro Ser Gln Glu Pro Pro Val Ala Ala Leu Ala Thr Leu Glu Arg
            995              1000             1005

Ser Val Pro Ile Ala Glu Asp Pro Pro Asn Val Pro Ala Pro Ile
1010                 1015             1020

Gln Ala Pro Ala Asn Gly His Asp Leu Gly Ala Ala Ala Val Ile
1025                 1030             1035

Val Asp His Phe Ala Leu Met Gln Glu Phe Leu Ala Ser Gln Asp
1040                 1045             1050

Arg Met Leu Ser Ala Leu Leu Thr Gly Ala Pro Ala Gln Thr Ala
1055                 1060             1065

Glu Met Ala Val Ser Val Asp Pro Trp Pro Leu Leu Gly Gln Val
1070                 1075             1080

Ile His Leu Asp Val Gln Ser Leu Val Cys Arg Arg Arg Phe Thr
1085                 1090             1095

Ile Gly Glu Asp Ile Phe Leu Arg Asp His Thr Leu Gly Gly Asn
1100                 1105             1110
```

-continued

```
Pro Ser Ser Leu Gln Pro Ala Leu Leu Pro Leu Pro Ile Leu Pro
1115                1120                1125

Phe Thr Thr Ser Met Glu Leu Leu Ala Glu Ala Ala Val Tyr Leu
1130                1135                1140

Ala Gly Gly Asn Gly Val Val Thr Ala Met Ser Glu Val Arg Gly
1145                1150                1155

Phe Arg Trp Leu Ala Leu Asp Arg Gly Val Leu Thr Val Glu Ala
1160                1165                1170

Val Leu Arg Arg Leu Pro Asp Gly Arg Tyr Gln Ala Gln Leu Phe
1175                1180                1185

Gln Leu Ser Asp Glu Asp Ala Ser Val Arg Leu Pro Ala Phe Glu
1190                1195                1200

Ala Val Ile Ala Val Ala Ala Tyr Thr Ser Ser Pro Ala Pro
1205                1210                1215

Arg Asp Leu Asp Pro Gly Ala Leu Trp Pro Leu Ser Ala Glu Leu
1220                1225                1230

Ala Asp Asp Arg Leu Tyr Ser Thr Gly Met Phe His Gly Pro Arg
1235                1240                1245

Phe Gln Ser Leu Lys His Ile His Cys Cys Gly Glu Arg Gly Ile
1250                1255                1260

Gln Ala Asp Leu Gly Val Trp Gly Thr Gly Asp Phe Phe Ala Asp
1265                1270                1275

Gly Arg Pro Gly Val Phe Gln Leu Glu Gln Ser Leu Ile Asp Ala
1280                1285                1290

Ala Gly Gln Leu Ala Ala Phe Trp Leu Ser Gln Asp Ile Asp Ser
1295                1300                1305

Pro Asp Phe Ser Met Phe Pro Phe Gln Val Arg Ser Phe Glu Gln
1310                1315                1320

Phe Gly Ala Ser Pro Pro Ala Gly Thr Arg Leu Leu Cys Arg Cys
1325                1330                1335

Thr Ser Arg Tyr Leu Ser Glu Asn Ala Thr Glu Ser His Leu Asp
1340                1345                1350

Tyr Ile Asp Gly Glu Gly Arg Val Leu Tyr Arg Leu Thr Gly Trp
1355                1360                1365

Gln Ser Arg Phe Phe Leu Ser Pro Pro Arg Tyr Gln Asp Phe Arg
1370                1375                1380

Val Ala Pro Gln Val Asn Tyr Leu Ser Glu Pro Trp Met Gln Ala
1385                1390                1395

Glu Thr Gly Leu Phe Val Arg Arg Tyr Glu Asn Pro Asp Asp Tyr
1400                1405                1410

Leu Glu Glu Ser Trp Glu Ile Trp Lys Arg Val Thr Ala His Leu
1415                1420                1425

Ile Leu Asn Glu Ala Glu Arg Thr Tyr Trp Tyr Ala Leu Pro Glu
1430                1435                1440

Gln Gly Pro Arg Arg Arg Asp Trp Leu Leu Gly Arg Leu Ala Ala
1445                1450                1455

Lys Glu Ala Leu Arg Gln Trp Thr Glu Ala Ala Tyr Gly Leu Gln
1460                1465                1470

Leu Ala Pro Ala Asp Phe Glu Ile Leu Ser Asn Glu Leu Gly Lys
1475                1480                1485

Pro Met Val Ser Cys Pro Ala Leu Ala Ala Phe Gly Pro Leu Pro
1490                1495                1500
```

```
Glu  Ile  Ser  Ile  Ala  His  Ser  Glu  Gly  His  Ala  Val  Ala  Ala  Val
     1505                1510                1515

Ala  Tyr  Gly  Met  Ala  Leu  Gly  Ile  Asp  Leu  Gln  Arg  Leu  Glu  Arg
     1520                1525                1530

Leu  Gly  Ser  Thr  Asp  Trp  Leu  Thr  Ala  Ala  Phe  Asp  Pro  Ser  Glu
     1535                1540                1545

Leu  Ala  Leu  Val  Ser  Ser  Pro  Thr  Glu  Leu  Ala  Leu  Ile  Gly  Leu
     1550                1555                1560

Trp  Ser  Ala  Lys  Glu  Ala  Ala  Lys  Ala  Phe  Gly  Thr  Gly  Leu
     1565                1570                1575

Glu  Gly  Glu  Pro  Arg  Arg  Trp  Gln  Val  Val  Ala  Arg  Asn  Pro  Glu
     1580                1585                1590

Gly  Thr  Glu  Met  Thr  Val  Val  His  Gly  Glu  His  Arg  Phe  Ser  Val
     1595                1600                1605

Arg  Leu  Trp  Tyr  Ala  Pro  Asp  Glu  Val  Phe  Ala  Val  Cys  Gly  Trp
     1610                1615                1620

Gln  Pro
     1625

<210> SEQ ID NO 56
<211> LENGTH: 268
<212> TYPE: PRT
<213> ORGANISM: Gloeobacter violaceus PCC 7421

<400> SEQUENCE: 56

Met  Pro  Glu  Tyr  Asp  Arg  Ser  Leu  Trp  Arg  Pro  Ala  Pro  Arg  Gln  Pro
1                   5                   10                  15

Gly  Leu  Gly  Ala  Asp  Asp  Val  His  Val  Trp  Arg  Ala  Cys  Leu  Met  Gln
                20                  25                  30

Pro  Asp  Ala  Arg  Val  Leu  Glu  Leu  Val  Glu  Thr  Leu  Ser  Glu  Asp  Glu
            35                  40                  45

Arg  His  Arg  Ala  Glu  Arg  Tyr  Arg  Phe  Val  Gly  Asp  Lys  Arg  Arg  Phe
        50                  55                  60

Ile  Val  Ala  Arg  Gly  Leu  Leu  Arg  Arg  Ile  Leu  Arg  Cys  Tyr  Leu  Glu
65                  70                  75                  80

Ile  Pro  Ala  Ala  Gln  Ile  Arg  Phe  Ser  Tyr  Gly  Ile  Lys  Gly  Lys  Pro
                85                  90                  95

Ala  Leu  Ala  Leu  Pro  Gly  Cys  Thr  Leu  Gln  Phe  Asn  Leu  Ser  His  Ser
            100                 105                 110

Arg  Glu  Val  Val  Leu  Ile  Ala  Leu  Thr  Leu  Arg  Arg  Asp  Ile  Gly  Ile
        115                 120                 125

Asp  Leu  Glu  Leu  Val  Arg  Ser  Leu  Ala  Ala  Met  Asp  Gln  Met  Ala  Glu
    130                 135                 140

Arg  Phe  Phe  Ser  Ala  His  Glu  Lys  Gln  Met  Leu  Gly  Val  Leu  Ala  Pro
145                 150                 155                 160

Leu  Glu  Arg  Gln  Glu  Thr  Phe  Phe  Arg  Phe  Trp  Ala  Cys  Lys  Glu  Ala
                165                 170                 175

Tyr  Ile  Lys  Ala  Cys  Gly  Lys  Gly  Leu  Ala  Leu  Ala  Leu  Asp  Gln  Phe
            180                 185                 190

Asp  Val  Ala  Ile  Glu  Pro  Asp  Gly  Gly  Val  Ser  Leu  Leu  Ala  Asn  Arg
        195                 200                 205

Gln  Glu  Arg  Asp  Ala  His  Pro  Gly  His  Trp  Ala  Ile  Arg  Gln  Ile  Glu
    210                 215                 220

Pro  Gly  Lys  Asn  Tyr  Val  Ala  Ala  Val  Ala  Val  Gly  Asp  Ala  Ala  Trp
225                 230                 235                 240
```

```
Asn Leu Arg Cys Trp Gln Trp Gln Asp Asp His Phe Asn Trp Glu Glu
            245                 250                 255

Asp Cys His Gln Asp Ser Cys Gln Thr Tyr Asp Glu
        260                 265

<210> SEQ ID NO 57
<211> LENGTH: 204
<212> TYPE: DNA
<213> ORGANISM: Nodularia harveyana UTEX B 2093

<400> SEQUENCE: 57
atttgtctca ttcccagggg ttagctctgt gtgcggtgaa ttatcacggt caaatcggca      60
taaatttaga gtgtattcgc cccatgtctg atgtggaagc cctggccaaa aggttttttt     120
taccgataaa atatgcttta atgcgatcgc tatctcctca ccaacagcaa gaaatatttt     180
ttcgttattg gacttgtaaa gagg                                            204

<210> SEQ ID NO 58
<211> LENGTH: 144
<212> TYPE: DNA
<213> ORGANISM: Nodularia spumigena BY1

<400> SEQUENCE: 58
atgaagaaga tagccgttgt ctgaaggatg tagaagcccg tgagaaaagg acgttgttac      60
tgcgagaata tgacgtagct gcgagcgcta tctgatcacc aacagcaaga aatatattac     120
aggtatggga cttgtaaaga ggca                                            144

<210> SEQ ID NO 59
<211> LENGTH: 212
<212> TYPE: DNA
<213> ORGANISM: Nodularia spumigena L575

<400> SEQUENCE: 59
tttaacttgt ctcattccca ggggttagct ctgtgtgcag tgaattatca caatcgaatt      60
gggatagatt tagaatatat tcgccggatg tctgatgtag aagcccttgc caaaaggttc     120
tttttaccgc gagaatatga cgtagtgcga tcgctatctg atcaccaaca gcaagaaata     180
tttttccgtt attggacgtt gtaaagaggc aa                                   212

<210> SEQ ID NO 60
<211> LENGTH: 166
<212> TYPE: DNA
<213> ORGANISM: Nodularia spumigena NSBR01

<400> SEQUENCE: 60
gaatttgaca accgtttggg atcatttaga atatattcgc cgaatgtctg atgtggaagc      60
ccttgccaaa aggttctttt taccgcgaga atatgacgta gtgcgatcgc tatctgatca     120
ccaacagcaa gaaatatttt tccgttattg gacttgtaaa gaggca                    166

<210> SEQ ID NO 61
<211> LENGTH: 205
<212> TYPE: DNA
<213> ORGANISM: Nodularia spumigena NSLA01

<400> SEQUENCE: 61
cttgtctcat tcccaggggt tagctctgtg tgcagtgaat tatcacaatc gaattgggat      60
agatttagaa tatattcgcc gaatgtctga tgtggaagcc cttgccaaaa ggttcttttt     120
```

```
accgcgagaa tatgacgtag tgcgatcgct atctgatcac caacagcaag aaatatttt    180 ccgttattgg acttgtaaag aggca                                         205
```

<210> SEQ ID NO 62
<211> LENGTH: 205
<212> TYPE: DNA
<213> ORGANISM: Nodularia spumigena NSLA02A4

<400> SEQUENCE: 62

```
cttgtctcat tcccaggggt tagctctgtg tgcagtgaat tatcatcatc gaattgggat    60
agatttagaa tatattcgcg caatgtctga tgtggaatgc cttgccaaaa ggttctttt   120 accgcgagaa tatgacgtag tgcgatcgct atctgatcac caacagcaag aaatatttt   180 ccgttattga cttgtgaaaa aggca                                         205
```

<210> SEQ ID NO 63
<211> LENGTH: 214
<212> TYPE: DNA
<213> ORGANISM: Nodularia spumigena

<400> SEQUENCE: 63

```
tggtttaact tgtctcattg ccaggggtta tgctctgtgt gcagggactt atcacaatcg    60
aattgggata gatttagaat atattcgccg aatgtctgat gtggaagccc ttgccaaaag   120 gttctttta ccgcgagaat atgacgtagt gcgatcgcta tctgatcacc aacagcaaga   180 aatattttc cgttattgga cttgtaaaga ggca                                214
```

<210> SEQ ID NO 64
<211> LENGTH: 122
<212> TYPE: DNA
<213> ORGANISM: Nostoc piscinale CENA21

<400> SEQUENCE: 64

```
ttggtattga tttagagtat atgcgctctg tgtcggattt ggaggcgctt gctcaaaggt    60 tcttttacc gagagaatat gagttagtgc gatcgcttcc tcctcatcaa caacaagaag   120
ca                                                                  122
```

<210> SEQ ID NO 65
<211> LENGTH: 239
<212> TYPE: PRT
<213> ORGANISM: Nostoc punctiforme PCC 73102

<400> SEQUENCE: 65

```
Met Thr Ala Thr His His Leu Trp Leu Pro Ala Ser Thr Asp Leu Thr
1               5                   10                  15

Leu Leu Ser Asp Glu Ile His Val Trp Arg Ile Glu Leu Asp Gln Pro
            20                  25                  30

Glu Leu Gln Leu Gln Asn Leu Ala Ala Thr Leu Ser Ser Asp Glu Met
        35                  40                  45

Ala Arg Ala Glu Arg Phe Tyr Phe Gln Glu His Arg Gln Arg Phe Ile
    50                  55                  60

Ala Gly Arg Gly Ile Leu Arg Thr Ile Leu Gly Arg Tyr Leu Gly Ile
65                  70                  75                  80

Gln Pro Leu Gln Val Gln Phe Asn Tyr Gln Gln Arg Gly Lys Pro Val
                85                  90                  95

Leu Ala Asp Thr Phe Ala Asp Ser Gly Leu Glu Phe Asn Leu Ser His
            100                 105                 110
```

Ser Gln Gly Met Gly Leu Cys Ala Val Asn Cys Thr His Pro Ile Gly
            115                 120                 125

Val Asp Leu Glu Tyr Ile Arg Ser Met Ser Asp Ile Glu Ala Leu Ala
    130                 135                 140

Lys Arg Phe Phe Leu Pro Arg Glu Tyr Glu Met Leu Arg Ser Leu Ser
145                 150                 155                 160

Pro Asn Gln Gln Glu Val Phe Phe Arg Tyr Trp Thr Cys Lys Glu
                165                 170                 175

Ala Tyr Leu Lys Ala Thr Gly Asp Gly Leu Ser Gln Leu Glu Gln Val
                180                 185                 190

Glu Val Leu Leu Thr Pro Thr Glu Pro Ala Lys Leu Gln Ile Leu Glu
        195                 200                 205

Asp Trp Ser Leu Phe Glu Leu Val Pro Thr Asn Asn Tyr Val Ala Ala
    210                 215                 220

Val Ala Ile Ala Asn Tyr Gly Trp Asn Leu Lys Cys Trp Gln Tyr
225                 230                 235

<210> SEQ ID NO 66
<211> LENGTH: 251
<212> TYPE: PRT
<213> ORGANISM: Nostoc punctiforme PCC 73102

<400> SEQUENCE: 66

Met Ile Ala Val Asp Thr Val Asp Cys Leu Trp Arg Pro Pro Thr
1               5                   10                  15

Asn Trp Ser Val Leu Gly Glu Asp Val His Val Trp Cys Thr Phe Leu
        20                  25                  30

Asn Gln Ser Thr Ser Arg Val Glu Thr Leu Ala Glu Leu Leu Ser Gln
        35                  40                  45

Asp Glu Arg Thr Arg Ser Glu Arg Phe Tyr Leu Glu Arg Asp Lys Lys
    50                  55                  60

Arg Tyr Ile Val Gly Arg Gly Leu Leu Arg Thr Ile Leu Gly Ser Tyr
65                  70                  75                  80

Leu Gly Thr Asn Ala Ser Gln Leu Gln Phe Cys Tyr Gly Ser His Gly
                85                  90                  95

Lys Pro Val Leu Ala Glu Thr Ser Gly Gly Asn Thr Leu Ser Phe Asn
                100                 105                 110

Leu Ser His Ser His Glu Leu Val Leu Tyr Ala Val Thr Arg Gln Arg
            115                 120                 125

Glu Ile Gly Val Asp Ile Glu Tyr Met Arg Pro Ile Ser Asp Phe Glu
    130                 135                 140

Gln Val Ala Glu Arg Cys Phe Ser Asp Arg Glu Lys Asp Val Phe Arg
145                 150                 155                 160

Lys Leu Pro Gln Asp Glu Lys Leu Gly Ala Phe Phe Asn Cys Trp Thr
                165                 170                 175

Arg Lys Glu Ala Tyr Leu Lys Ala Thr Gly Gln Gly Leu Val Phe Pro
                180                 185                 190

Met Asp Gln Leu Asp Val Ser Leu Ser Gln Asn Glu Pro Val Gln Leu
        195                 200                 205

Tyr Ser Ile Asn Gly Asp Arg Ser Thr Val Ile Arg Trp Ser Leu Gln
    210                 215                 220

Ala Phe Ile Pro Ala Leu Ser Tyr Val Gly Ala Leu Ala Val Glu Gly
225                 230                 235                 240

Arg Asp Trp His Leu Lys Cys Trp Gln Trp Glu
                245                 250

<210> SEQ ID NO 67
<211> LENGTH: 300
<212> TYPE: PRT
<213> ORGANISM: Nostoc punctiforme PCC 73102

<400> SEQUENCE: 67

Met Pro Pro Ser Thr Thr His Leu Pro Glu Phe Ala Gln Cys Leu Pro
1               5                   10                  15

Thr Ile Ala Ala Met His Ile Asp Ile Gly Gly Glu Leu Ala Val His
            20                  25                  30

Ala Lys Asp Tyr Leu Ser Ala Lys Glu Leu Ala Tyr Phe His Gln Phe
        35                  40                  45

Lys His Pro Arg Arg Arg Tyr Glu Trp Phe Thr Ala Arg Leu Val Cys
    50                  55                  60

Lys Leu Leu Phe Ser Arg Tyr Leu Ser Asn Thr His Leu Ala Asn Ser
65                  70                  75                  80

Asn Ser Val Trp Pro Pro Thr Ile Gln Lys Leu Gly Cys Asn Asp Ile
                85                  90                  95

Ala Thr Val Leu Pro Ile Val Tyr Arg Ser Ile Glu Ile Leu Pro Ser
            100                 105                 110

Asn Pro Ser Leu Lys Gly Ala Pro Gln Leu Phe Trp Gln Gly Asn Ile
        115                 120                 125

Leu Ser Ala Met Tyr Leu Ser Ile Ser His Ala Gly Gly Leu Ala Ile
    130                 135                 140

Ala Ser Leu Ser Ser Ser Gly Pro Val Gly Leu Asp Leu Glu Glu Pro
145                 150                 155                 160

Ile Ser His Cys Pro Asn Phe Tyr Glu Ser Tyr Phe Ser Lys Gln Glu
                165                 170                 175

Thr Leu Trp Val Gln Gln Ile Lys Asp Glu Leu Ser Ile Ser Gln
            180                 185                 190

Leu Tyr Thr Leu Leu Trp Thr Leu Lys Glu Ser Tyr Leu Lys Thr Gly
        195                 200                 205

Ile Ser Pro Ile Asn Asn Ile Cys Asp Phe Ala Asn Leu Glu Ile Lys
    210                 215                 220

Ile Asp Thr Ser Leu Phe Thr Val Ser Lys His Leu Pro Lys Ile Gly
225                 230                 235                 240

Phe Asn Ser Gln Leu His Ile Leu Lys Leu Gln Phe Ser Tyr Ala Lys
                245                 250                 255

Ser Thr Phe Ala Pro Tyr Ala Phe Ser Ile Met Ala Asn Leu Ile
            260                 265                 270

Leu Ser Ile Val Ala Phe Glu Leu Asn Thr His Leu Glu Asn Val Leu
        275                 280                 285

Lys Val Leu Arg Glu Asp Asn Ser Leu Leu His Lys
    290                 295                 300

<210> SEQ ID NO 68
<211> LENGTH: 237
<212> TYPE: PRT
<213> ORGANISM: Nostoc sp. PCC 7120

<400> SEQUENCE: 68

Met Leu Gln His Thr Trp Leu Pro Lys Pro Pro Asn Leu Thr Leu Leu
1               5                   10                  15

Ser Asp Glu Val His Leu Trp Arg Ile Pro Leu Asp Gln Pro Glu Ser
            20                  25                  30

```
Gln Leu Gln Asp Leu Ala Ala Thr Leu Ser Ser Asp Glu Leu Ala Arg
        35                  40                  45

Ala Asn Arg Phe Tyr Phe Pro Glu His Arg Arg Phe Thr Ala Gly
 50                  55                  60

Arg Gly Ile Leu Arg Ser Ile Leu Gly Gly Tyr Leu Gly Val Glu Pro
 65                  70                  75                  80

Gly Gln Val Lys Phe Asp Tyr Glu Ser Arg Gly Lys Pro Ile Leu Gly
                 85                  90                  95

Asp Arg Phe Ala Glu Ser Gly Leu Leu Phe Asn Leu Ser His Ser Gln
                100                 105                 110

Asn Leu Ala Leu Cys Ala Val Asn Tyr Thr Arg Gln Ile Gly Ile Asp
                115                 120                 125

Leu Glu Tyr Leu Arg Pro Thr Ser Asp Leu Glu Ser Leu Ala Lys Arg
130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
                180                 185                 190

Ala Leu Thr Pro Thr Glu Pro Ala Lys Leu Gln Thr Ala Pro Ala Trp
                195                 200                 205

Ser Leu Leu Glu Leu Val Pro Asp Asp Asn Cys Val Ala Ala Val Ala
                210                 215                 220

Val Ala Gly Phe Gly Trp Gln Pro Lys Phe Trp His Tyr
225                 230                 235

<210> SEQ ID NO 69
<211> LENGTH: 218
<212> TYPE: PRT
<213> ORGANISM: Prochlorococcus marinus subsp. marinus str. CCMP1375

<400> SEQUENCE: 69

Met Arg Leu Thr Asp Ile Gln Lys Pro Arg Val Leu Pro Leu Trp Ile
 1               5                  10                  15

Phe Pro Met Asp Ser Pro Leu Lys Glu Ile Ser Ile Ser Glu Glu Lys
                 20                  25                  30

Ile Ala Asn Ser Leu His Pro Arg Ala Lys Glu Tyr Lys His Ala
         35                  40                  45

Arg Ser Tyr Val Arg Phe Ala Leu Ser Gln Phe Phe Lys Leu Asn Pro
 50                  55                  60

Leu Glu Ile Pro Leu Lys Ala Ser Ile Gly Lys Ala Pro Leu Leu Gly
 65                  70                  75                  80

Asn Asn Leu Gly His Val Ser Phe Ser His Cys Asn Asp Ala Leu Leu
                 85                  90                  95

Ile Gly Trp Ser Pro Thr Lys Leu Gly Val Asp Ile Glu Arg Ser Asp
                100                 105                 110

Arg Ala Leu Ser Ala Glu Gly Ile Ser Glu Arg Phe Phe His Lys Tyr
                115                 120                 125

Asp Gln Asn Asn Leu Lys Ser Leu Asn Asn Glu Asp Phe Arg Lys Lys
                130                 135                 140

Val Leu Glu Gln Trp Val Ile Lys Glu Ala Ala Ile Lys Trp Gln Arg
145                 150                 155                 160

Gly Thr Leu Ser Lys Asp Leu Lys Asn Trp His Ile Lys Asn Lys Ser
```

-continued

```
                165                 170                 175
Asn Val Ala Ile His Gln Thr Leu Asn His Glu Val Lys Ile Gln Thr
            180                 185                 190
Thr Ile Tyr Arg Ser Trp Ile Ile Ala Ile Ala Ser Asn Asp Asn Gln
        195                 200                 205
Gly Lys Gly Asp Leu Met Ile Cys Ala Asn
    210                 215

<210> SEQ ID NO 70
<211> LENGTH: 218
<212> TYPE: PRT
<213> ORGANISM: Prochlorococcus marinus subsp. pastoris str. CCMP1986

<400> SEQUENCE: 70

Met Thr Leu Leu Asn Asn Tyr Glu Tyr Lys Ile Pro Lys Ile Trp Phe
1               5                   10                  15
His Glu Ile Lys Gly Val Gln Asp Val Ala Thr Leu Asn Glu Leu Glu
            20                  25                  30
Ile Ala Asn Lys Leu Ser Arg His Arg Ala Asn Ile Phe Leu Glu Ser
        35                  40                  45
Arg Ala Tyr Ile Arg Gln Cys Leu Gly Asn Leu Phe Asn Leu Asn Pro
    50                  55                  60
Leu Glu Val Pro Ile Ile Ala Asn Pro Gly Glu Pro Pro Glu Leu Pro
65                  70                  75                  80
Lys Gly Met Gly Tyr Cys Ser Phe Ser His Cys Asn Asp Ala Ile Ile
                85                  90                  95
Leu Val Trp His Glu Arg Lys Ile Gly Ile Asp Ile Glu Arg Leu Asp
            100                 105                 110
Arg Asn Phe Asn Tyr Glu Lys Leu Ala Lys Lys Tyr Phe Phe Lys Ser
        115                 120                 125
Asn Ser Leu Asn Thr Thr Ser Glu Ser Tyr Arg Lys Thr Ile Leu Asn
    130                 135                 140
Gln Trp Cys Ala Val Glu Ala Ala Ile Lys Trp Asp His Gly Lys Leu
145                 150                 155                 160
Ala Glu Asp Ile Lys Glu Trp Gln Tyr Ser Glu Asn Asp Lys Ile Leu
                165                 170                 175
Phe His Asn Lys Lys Leu Lys Leu Lys Phe Thr Gln Ile Asn Leu
            180                 185                 190
Tyr Lys Trp Thr Ile Ser Leu Ala Tyr Lys Asp Thr Ser His Phe Ile
        195                 200                 205
Pro Asn Ile Ile Cys Ser Ser Lys Met Val
    210                 215

<210> SEQ ID NO 71
<211> LENGTH: 217
<212> TYPE: PRT
<213> ORGANISM: Prochlorococcus marinus str. MIT 9313

<400> SEQUENCE: 71

Met Pro Leu Pro Leu Asn Ser Arg Ser Val Leu Ala Leu Trp Leu Phe
1               5                   10                  15
Pro Met Gln Ala Pro Leu Met Pro Ile Ser Pro Glu Glu Gln Trp
            20                  25                  30
Ala Gly Arg Leu Ser Ala Arg Arg Ser Arg Gln Phe Arg Gln Ser Arg
        35                  40                  45
Gly Tyr Val Arg Asp Ala Leu Ala Asp Leu Trp Gln Val Ser Ala Leu
```

```
              50                  55                  60
Glu Ile Pro Leu Gln Ala Pro Pro Gly Lys Pro Pro Glu Leu Ala Asn
 65                  70                  75                  80

Gly Trp Gly Tyr Ile Ser Phe Ser His Cys Gln Asp Ala Leu Leu Val
                 85                  90                  95

Gly Trp Ser Pro Gln Arg Val Gly Val Asp Leu Glu Arg Ser Asp Arg
            100                 105                 110

Pro Ile Ala Ala Glu Leu Leu Ala Arg Arg Tyr Phe Cys Ala Asp Asp
        115                 120                 125

Gln Ser Ala Leu Cys His Leu Arg Gly Ala Ala Leu Arg Asp Ala Val
    130                 135                 140

Leu Glu Gln Trp Leu Ser Lys Glu Ala Ala Ile Lys Trp Gln Arg Gly
145                 150                 155                 160

Ser Leu Ala Ala Asp Leu Ile His Trp Arg Cys Gly Val Asp Ser Val
                165                 170                 175

Phe Ala Val His Glu Val Leu Gly His Gln Val Asp Val His Arg Ile
            180                 185                 190

His His Asn Leu Trp Ser Met Ala Val Val Ser Asp Phe Ser Ala Met
        195                 200                 205

Ser Asn Ala Pro Met Leu Cys Leu Val
    210                 215

<210> SEQ ID NO 72
<211> LENGTH: 259
<212> TYPE: PRT
<213> ORGANISM: Synechococcus elongatus PCC 7942

<400> SEQUENCE: 72

Met Gln Arg Pro Asn Pro Ser Asp Ala Val Pro Val Pro Ser Ile Pro
  1               5                  10                  15

Ser Cys Asp Arg Gly Pro Ile Pro Asn Pro Val Thr Trp Arg Thr Ser
                 20                  25                  30

Pro Glu Pro Leu Phe Leu Ser Ala Gln Thr Val His Leu Trp Arg Cys
            35                  40                  45

Ser Leu Thr Arg Ser Leu Ser Ser Ala Glu Gln Ala Ile Val Ala Ala
    50                  55                  60

Asp Cys Asp Arg Ala Gln Ala Tyr Gly Ser Asn Arg Arg His Gln Phe
 65                  70                  75                  80

Leu Cys Gly Arg Trp Trp Leu Arg Gln Leu Leu Ser Leu Tyr Leu Pro
                 85                  90                  95

Glu Glu Pro Ala Asp Phe Arg Phe Gln Leu Ser Pro Thr Gly Lys Pro
            100                 105                 110

Glu Leu Pro Gln Ser Asn Leu Cys Phe Asn Leu Ser His Ser Gly Ser
        115                 120                 125

Thr Leu Leu Ile Ala Ile Ala Trp Gln Pro Val Gly Val Asp Val Glu
    130                 135                 140

Gln Pro Arg Ser Arg Ser Trp Leu Ala Leu Ala Arg Arg Tyr Phe Pro
145                 150                 155                 160

Ser Ala Glu Leu Ala Ala Met Gln Gln Ser Thr Asp Cys Asp Arg Trp
                165                 170                 175

Gly Leu Ala Ser Trp Val Cys Lys Glu Ala Trp Ile Lys Ala Gln Gly
            180                 185                 190

Arg Thr Leu Ala Asn Ser Leu Arg His Leu Gln Cys Ala Trp Thr Ala
        195                 200                 205
```

```
Asn Gly Gln Pro Arg Leu Ser Gly Leu Gly Ser Glu Ser Gln Val
    210                 215                 220

Gln Leu Leu Gln Val Asp Pro Gln Glu Gln Leu Trp Ala Ala Ile Ala
225                 230                 235                 240

Met Pro Ala Gly Trp Asn Tyr Gln Thr Trp Thr Ala Ala Ile Ile Arg
                245                 250                 255

Lys Asn His

<210> SEQ ID NO 73
<211> LENGTH: 218
<212> TYPE: PRT
<213> ORGANISM: Synechococcus sp. WH 8102

<400> SEQUENCE: 73

Met Glu Pro Pro Leu Leu Gly Ser Arg Ser Val Thr Ala Leu Trp Leu
1               5                   10                  15

Ile Pro Glu His Gln Asp Leu Pro Ser Asp Val Glu Leu Ser Pro Val
                20                  25                  30

Glu Ala Gly Trp Met Asp Gly Met Ala Met Ser Arg Ala Val Ala Phe
            35                  40                  45

Arg Arg Ser Arg Leu Trp Met Arg Arg Cys Leu Ala Asp Cys Phe Glu
    50                  55                  60

Val Asp Pro Ala Thr Val Pro Leu Gln Ala Pro Gly Glu Pro Pro
65                  70                  75                  80

Thr Leu Ala Asp Gly Trp Gly Cys Leu Ser Leu Ser His Cys Cys Asp
                85                  90                  95

Ala Val Leu Val Ala Trp Ser Pro Asp Ala Val Gly Val Asp Leu Glu
            100                 105                 110

Arg Cys Asp Arg Cys Phe Pro Ala Ala Ala Leu Ala Asp Arg Phe Tyr
        115                 120                 125

Cys Ala Glu Asp Arg Arg Glu Leu Asp Gly Leu Ala Gly Glu Thr Leu
    130                 135                 140

Arg Met Ala Val Leu Lys Gln Trp Val Ala Lys Glu Ala Leu Ile Lys
145                 150                 155                 160

Met Gln Arg Gly Ser Leu Ala Leu Asp Leu Ser Arg Trp Arg Cys Gly
                165                 170                 175

Ala Asp Ala Cys Gln Gly Leu His Pro Asp Leu Glu His Pro Val Pro
            180                 185                 190

Val His Arg Leu Gln Leu Glu Gly Trp Leu Met Ala Val Ala Gly Ala
        195                 200                 205

Ala Gly Gln Val Gly Pro Ile Cys Leu Ala
    210                 215

<210> SEQ ID NO 74
<211> LENGTH: 246
<212> TYPE: PRT
<213> ORGANISM: Synechocystis sp. PCC 6803

<400> SEQUENCE: 74

Met Leu Pro Gln Pro Gln Ile Trp Leu Cys Pro Thr Asp Arg Pro Leu
1               5                   10                  15

Ile Pro Gly Tyr Gln Ala Leu Leu Ser Ser Glu Met Ala Arg Gly
                20                  25                  30

Glu Arg Tyr Gln Arg Pro Gln Asp Lys Gln Arg Phe Leu Thr Met Arg
            35                  40                  45

Leu Ala Leu Arg Ile Leu Leu Ala Arg Gln Leu Asp Cys Leu Pro Gln
```

```
                50                  55                  60
Gln Leu Gln Phe Thr Tyr Gly Pro Gln Gly Lys Pro Glu Leu Val Asp
 65                  70                  75                  80

Arg Glu Arg Arg Ser Pro Trp Phe Asn Val Ala His Ser Gly Asn Tyr
                 85                  90                  95

Gly Leu Ile Gly Leu Ser Thr Glu Gly Ile Gly Val Asp Leu Gln
            100                 105                 110

Ile Met Leu Pro Lys Pro His Tyr Leu Lys Leu Ala Lys Arg Phe Phe
            115                 120                 125

Ala Pro Gln Glu Val Gln Gln Leu Glu Ser Leu Glu Gly Gly Lys Arg
            130                 135                 140

Thr Lys Leu Phe Tyr Gln Leu Trp Thr Ala Lys Glu Ala Phe Leu Lys
145                 150                 155                 160

Ala Thr Gly Lys Gly Ile Ser Gly Gly Leu Asn Gln Val Ile Pro Asp
                165                 170                 175

Glu Asn Leu Ala Lys Tyr Gln Tyr Leu Pro Asp Ser Gly Asp Thr Asn
            180                 185                 190

His Trp Arg Leu Ser Ser Gln Pro Leu Leu Ala Asp Gln Gly Ser Asn
            195                 200                 205

Asp Asn Tyr Trp Met Ala Ile Ala Trp Cys Thr Asn Glu Val Asn Gln
            210                 215                 220

Val Glu Ser Asn Tyr Leu Pro Asn Ile Gln Pro Phe Gln Trp Pro Arg
225                 230                 235                 240

Asn Leu Asp Ser Leu Pro
                245

<210> SEQ ID NO 75
<211> LENGTH: 126
<212> TYPE: DNA
<213> ORGANISM: Synechocystis sp. PCC 7008

<400> SEQUENCE: 75
ctgcgttgca attagctaaa cgttttttg ccccagagga aaatatgtta ttacgatcct    60
tacaggacaa tgaacaaatc caagccttt atcaactttg acaggaaga aggcaaatgg   120 cagata                                                              126

<210> SEQ ID NO 76
<211> LENGTH: 195
<212> TYPE: PRT
<213> ORGANISM: Thermosynechococcus elongatus BP-1

<400> SEQUENCE: 76

Met Trp Asp Cys Pro Leu Pro Pro Ile Val Val Pro Gln Trp Arg Ala
 1               5                  10                  15

Pro His Pro Asn Leu Thr Leu Asp Ser Ser Ala Leu His Leu Trp Trp
                20                  25                  30

Leu Thr Leu Pro Pro Asp Val Pro Arg Gly Val Ile Leu Arg Ala Tyr
            35                  40                  45

Leu Arg Arg Tyr Gln Pro Asn Leu Gly Glu Arg Pro Leu Pro Arg Ala
        50                  55                  60

Ala Gly Gly Lys Pro Tyr Leu Asn Gly Leu Glu Phe Asn Trp Ser His
 65                  70                  75                  80

Ser Gly Asn Leu Ala Val Leu Ala Val Ser Gly Arg Ala Ala Val Gly
                85                  90                  95

Val Asp Val Glu Ile Leu Arg Leu Cys Pro Gln Arg Ala Ala Ile Ser
```

```
                100             105             110
Arg Arg Phe Phe Gly Ala Ala Leu Gln Gln Arg Ile Leu Glu Gly Gly
        115                 120                 125

Asp Arg Ser Phe Leu Gln Ala Trp Thr Tyr Tyr Glu Ala Trp Leu Lys
130                 135                 140

Ala Gln Gly Ile Gly Val Trp Gln Arg Thr Ala Ala Gln Ser Leu Glu
145                 150                 155                 160

His Trp Val Ala Ser Phe Pro Val Gly Asp Arg Ala Ile Ala Ser Val
                165                 170                 175

Val Val Leu Thr Pro Thr Pro Gln Cys Phe Phe Phe Arg Pro Glu
            180                 185                 190

Ala Met Ala
        195

<210> SEQ ID NO 77
<211> LENGTH: 255
<212> TYPE: PRT
<213> ORGANISM: Gloeobacter violaceus PCC 7421

<400> SEQUENCE: 77

Met Val Ala Ile Glu Ala Pro Trp Arg Pro Thr Ala Ala Pro Pro Val
1               5                   10                  15

Leu Thr Pro Ala Ala Val His Ile Trp Gln Ala Asp Leu Asp Trp Pro
            20                  25                  30

Ala Ala Pro Leu Pro Val Leu Glu Arg Thr Leu Cys Pro Gln Glu Arg
        35                  40                  45

Ser Arg Ala Glu Arg Phe Cys Phe Glu Gln His Arg Arg Arg Phe Ile
    50                  55                  60

Val Gly Arg Ala Thr Leu Arg Met Leu Leu Gly Leu Tyr Leu Gln Ser
65                  70                  75                  80

Glu Pro Ala Cys Val Pro Ile Ser Tyr Gly Ala His Gly Lys Pro Leu
                85                  90                  95

Leu Ala Asp Gly Ala His Pro Leu Arg Phe Asn Leu Ser His Ser Gln
            100                 105                 110

Gly Lys Ala Val Tyr Ala Phe Ser Cys Gly Arg Glu Val Gly Val Asp
        115                 120                 125

Leu Glu Trp Asp Arg Pro Leu Ala Asn Phe Asp Gln Leu Ala Arg Val
130                 135                 140

Ala Phe Ser Glu Asp Glu Asn Arg Val Phe Lys Ala Leu Ala Pro Tyr
145                 150                 155                 160

Gln Arg Arg Ala Ala Phe Phe Arg Cys Trp Thr Arg Lys Glu Ala Tyr
                165                 170                 175

Ala Lys Ala Arg Gly Tyr Gly Phe Ala Leu Ala Pro Asp Arg Tyr Thr
            180                 185                 190

Val Ser Leu Ala Pro Asp Ala Pro Ala Leu Leu Gln Ser Arg Glu
        195                 200                 205

Glu Ser Gly Glu Ala Gly Arg Trp Val Leu Leu Asp Leu Leu Pro Trp
210                 215                 220

Pro Asp Tyr Pro Ala Ala Leu Ala Val Glu Gly Ser Ser Gly Gln Val
225                 230                 235                 240

His Cys Trp His Ser Pro Glu Pro Ile Ser Arg Arg Ser Pro Arg
                245                 250                 255

<210> SEQ ID NO 78
<211> LENGTH: 251
```

```
<212> TYPE: PRT
<213> ORGANISM: Nostoc punctiforme PCC 73102

<400> SEQUENCE: 78

Met Ile Ala Val Asp Thr Val Asp Cys Leu Trp Arg Pro Pro Thr
1               5                   10                  15

Asn Trp Ser Val Leu Gly Glu Asp Val His Val Trp Cys Thr Phe Leu
            20                  25                  30

Asn Gln Ser Thr Ser Arg Val Glu Thr Leu Ala Glu Leu Leu Ser Gln
        35                  40                  45

Asp Glu Arg Thr Arg Ser Glu Arg Phe Tyr Leu Glu Arg Asp Lys Lys
    50                  55                  60

Arg Tyr Ile Val Gly Arg Gly Leu Leu Arg Thr Ile Leu Gly Ser Tyr
65                  70                  75                  80

Leu Gly Thr Asn Ala Ser Gln Leu Gln Phe Cys Tyr Gly Ser His Gly
                85                  90                  95

Lys Pro Val Leu Ala Glu Thr Ser Gly Gly Asn Thr Leu Ser Phe Asn
            100                 105                 110

Leu Ser His Ser His Glu Leu Val Leu Tyr Ala Val Thr Arg Gln Arg
        115                 120                 125

Glu Ile Gly Val Asp Ile Glu Tyr Met Arg Pro Ile Ser Asp Phe Glu
    130                 135                 140

Gln Val Ala Glu Arg Cys Phe Ser Asp Arg Glu Lys Asp Val Phe Arg
145                 150                 155                 160

Lys Leu Pro Gln Asp Glu Lys Leu Gly Ala Phe Phe Asn Cys Trp Thr
                165                 170                 175

Arg Lys Glu Ala Tyr Leu Lys Ala Thr Gly Gln Gly Leu Val Phe Pro
            180                 185                 190

Met Asp Gln Leu Asp Val Ser Leu Ser Gln Asn Glu Pro Val Gln Leu
        195                 200                 205

Tyr Ser Ile Asn Gly Asp Arg Ser Thr Val Ile Arg Trp Ser Leu Gln
    210                 215                 220

Ala Phe Ile Pro Ala Leu Ser Tyr Val Gly Ala Leu Ala Val Glu Gly
225                 230                 235                 240

Arg Asp Trp His Leu Lys Cys Trp Gln Trp Glu
                245                 250

<210> SEQ ID NO 79
<211> LENGTH: 268
<212> TYPE: PRT
<213> ORGANISM: Gloeobacter violaceus PCC 7421

<400> SEQUENCE: 79

Met Pro Glu Tyr Asp Arg Ser Leu Trp Arg Pro Ala Pro Arg Gln Pro
1               5                   10                  15

Gly Leu Gly Ala Asp Asp Val His Val Trp Arg Ala Cys Leu Met Gln
            20                  25                  30

Pro Asp Ala Arg Val Leu Glu Leu Val Glu Thr Leu Ser Glu Asp Glu
        35                  40                  45

Arg His Arg Ala Glu Arg Tyr Arg Phe Val Gly Asp Lys Arg Arg Phe
    50                  55                  60

Ile Val Ala Arg Gly Leu Leu Arg Arg Ile Leu Arg Cys Tyr Leu Glu
65                  70                  75                  80

Ile Pro Ala Ala Gln Ile Arg Phe Ser Tyr Gly Ile Lys Gly Lys Pro
                85                  90                  95
```

```
Ala Leu Ala Leu Pro Gly Cys Thr Leu Gln Phe Asn Leu Ser His Ser
            100                 105                 110

Arg Glu Val Val Leu Ile Ala Leu Thr Leu Arg Arg Asp Ile Gly Ile
        115                 120                 125

Asp Leu Glu Leu Val Arg Ser Leu Ala Ala Met Asp Gln Met Ala Glu
    130                 135                 140

Arg Phe Phe Ser Ala His Glu Lys Gln Met Leu Gly Val Leu Ala Pro
145                 150                 155                 160

Leu Glu Arg Gln Glu Thr Phe Phe Arg Phe Trp Ala Cys Lys Glu Ala
                165                 170                 175

Tyr Ile Lys Ala Cys Gly Lys Gly Leu Ala Leu Ala Leu Asp Gln Phe
            180                 185                 190

Asp Val Ala Ile Glu Pro Asp Gly Gly Val Ser Leu Leu Ala Asn Arg
        195                 200                 205

Gln Glu Arg Asp Ala His Pro Gly His Trp Ala Ile Arg Gln Ile Glu
    210                 215                 220

Pro Gly Lys Asn Tyr Val Ala Val Ala Val Gly Asp Ala Ala Trp
225                 230                 235                 240

Asn Leu Arg Cys Trp Gln Trp Gln Asp Asp His Phe Asn Trp Glu Glu
                245                 250                 255

Asp Cys His Gln Asp Ser Cys Gln Thr Tyr Asp Glu
            260                 265

<210> SEQ ID NO 80
<211> LENGTH: 246
<212> TYPE: PRT
<213> ORGANISM: Synechocystis sp. PCC 6803

<400> SEQUENCE: 80

Met Leu Pro Gln Pro Gln Ile Trp Leu Cys Pro Thr Asp Arg Pro Leu
1               5                   10                  15

Ile Pro Gly Tyr Gln Ala Leu Leu Ser Ser Glu Glu Met Ala Arg Gly
            20                  25                  30

Glu Arg Tyr Gln Arg Pro Gln Asp Lys Gln Arg Phe Leu Thr Met Arg
        35                  40                  45

Leu Ala Leu Arg Ile Leu Leu Ala Arg Gln Leu Asp Cys Leu Pro Gln
    50                  55                  60

Gln Leu Gln Phe Thr Tyr Gly Pro Gln Gly Lys Pro Glu Leu Val Asp
65                  70                  75                  80

Arg Glu Arg Arg Ser Pro Trp Phe Asn Val Ala His Ser Gly Asn Tyr
                85                  90                  95

Gly Leu Ile Gly Leu Ser Thr Glu Gly Glu Ile Gly Val Asp Leu Gln
            100                 105                 110

Ile Met Leu Pro Lys Pro His Tyr Leu Lys Leu Ala Lys Arg Phe Phe
        115                 120                 125

Ala Pro Gln Glu Val Gln Gln Leu Glu Ser Leu Glu Gly Glu Lys Arg
    130                 135                 140

Thr Lys Leu Phe Tyr Gln Leu Trp Thr Ala Lys Glu Ala Phe Leu Lys
145                 150                 155                 160

Ala Thr Gly Lys Gly Ile Ser Gly Gly Leu Asn Gln Val Ile Pro Asp
                165                 170                 175

Glu Asn Leu Ala Lys Tyr Gln Tyr Leu Pro Asp Ser Gly Asp Thr Asn
            180                 185                 190

His Trp Arg Leu Ser Ser Gln Pro Leu Leu Ala Asp Gln Gly Ser Asn
        195                 200                 205
```

```
Asp Asn Tyr Trp Met Ala Ile Ala Trp Cys Thr Asn Glu Val Asn Gln
            210                 215                 220

Val Glu Ser Asn Tyr Leu Pro Asn Ile Gln Pro Phe Gln Trp Pro Arg
225                 230                 235                 240

Asn Leu Asp Ser Leu Pro
                245

<210> SEQ ID NO 81
<211> LENGTH: 126
<212> TYPE: DNA
<213> ORGANISM: Synechocystis sp. PCC 7008

<400> SEQUENCE: 81
ctgcgttgca attagctaaa cgttttttg ccccagagga aaatatgtta ttacgatcct      60
tacaggacaa tgaacaaatc caagccttt atcaactttg acaggaaga aggcaaatgg     120 cagata                                                              126

<210> SEQ ID NO 82
<211> LENGTH: 251
<212> TYPE: PRT
<213> ORGANISM: Crocosphaera watsonii WH 8501

<400> SEQUENCE: 82

Met Leu Thr Trp Tyr Lys Lys Tyr Gln Ile Met Asn Ile Thr Trp Lys
1               5                   10                  15

Tyr Pro Pro Lys Asn Leu Thr Ile Asn Ala Thr Glu Ile His Ile Trp
            20                  25                  30

Lys Thr His Leu Glu Gln Ser Ala Ile Asp Phe Lys Glu Ser Phe Asp
        35                  40                  45

Ile Leu Asn Glu Glu Glu Lys Ile Lys Ala Gln Arg Phe Arg Phe Glu
    50                  55                  60

Lys His Gln Gln Arg Phe Thr Ile Ala Arg Ser Ser Leu Arg Arg Ile
65                  70                  75                  80

Leu Ser Leu Tyr Leu Trp Ile Ser Pro Gln Lys Ile Asp Phe Gln Tyr
                85                  90                  95

Asn Ala Tyr Gly Lys Pro Gln Leu Leu Asp Asn Ile Asn Lys Ile Asn
            100                 105                 110

Leu Gln Phe Asn Val Ser His Ser Glu Asn Ile Ala Ile Tyr Gly Ile
        115                 120                 125

Thr Cys His Asn Leu Ile Gly Val Asp Ile Glu Tyr Met Arg Pro Met
    130                 135                 140

Ala Glu Ala Glu Asn Leu Ala Lys Arg Phe Phe Ser Gln Lys Glu Phe
145                 150                 155                 160

Glu Gln Ile Ser Lys Leu Pro Ser Ala Glu Gln Asp Arg Glu Phe Phe
                165                 170                 175

Gln Leu Trp Thr Gly Lys Glu Ala Tyr Leu Lys Ala Ile Gly Lys Gly
            180                 185                 190

Ile Ser Gly Gly Leu Glu Lys Val Glu Ile Ser Pro His Glu Pro Arg
        195                 200                 205

Lys Phe Ile Arg Leu Pro Glu Ser Asn Pro Asn Tyr Asn Leu Val
    210                 215                 220

Tyr Leu Thr Pro Glu Asn Asn Tyr Leu Ala Ala Ile Ala Val Glu Asn
225                 230                 235                 240

Lys Gln Gln Asn Tyr Gln Tyr Trp Gln Leu Asn
                245                 250
```

<210> SEQ ID NO 83
<211> LENGTH: 245
<212> TYPE: PRT
<213> ORGANISM: Trichodesmium erythraeum IMS101

<400> SEQUENCE: 83

```
Met Leu Leu Asp Gln Ala Glu Lys Lys Phe Glu Leu Ser Glu Asn Asn
1               5                   10                  15

Val His Ile Trp Ser Thr Asn Leu Lys Leu Ser Ser Asp Lys Ile Glu
            20                  25                  30

Glu Leu Ser Thr Ile Leu Ser Pro Asp Glu Lys Asn Arg Ala Asn Lys
        35                  40                  45

Phe Tyr Phe Glu Lys Asp Lys Asn Arg Phe Ile Ile Ala Arg Gly Thr
    50                  55                  60

Leu Arg Thr Ile Leu Ser Arg Tyr Leu Asn Ile Glu Pro Lys Lys Leu
65                  70                  75                  80

Gln Phe Thr Tyr Ser Asp Arg Gly Lys Pro Tyr Leu Lys Asn Thr Ser
                85                  90                  95

Ile Leu Phe Asn Leu Ser His Ser Gln Asp Leu Ala Leu Tyr Gly Ile
            100                 105                 110

Thr Lys Ile Asn Leu Ile Gly Ile Asp Leu Glu Tyr Ile Arg Pro Met
        115                 120                 125

Asn Asp Ala Val Asn Leu Ala Lys Arg Phe Phe Ser Leu Gln Glu Tyr
    130                 135                 140

Lys Leu Ile Ser Gln Leu Pro Pro Gln Lys Gln Gln Glu Thr Phe Phe
145                 150                 155                 160

Lys Ile Trp Thr Cys Lys Glu Ala Tyr Leu Lys Ala Thr Gly Asp Gly
                165                 170                 175

Leu Ala Gly His Leu Glu Lys Val Glu Ile Cys Leu Thr Pro Glu Lys
            180                 185                 190

Pro Val Glu Phe Phe Ser Ile Asn Gly Asp Ile Glu Ala Ala Ser His
        195                 200                 205

Trp Tyr Leu Tyr Gln Phe Ile Pro Gln Pro Asn Tyr Ile Ala Ala Val
    210                 215                 220

Val Val Ala Glu Lys Asn Gln Lys Leu Ser Phe Trp Gln Ile Asn Asn
225                 230                 235                 240

Thr Asp Ile Val Phe
                245
```

<210> SEQ ID NO 84
<211> LENGTH: 239
<212> TYPE: PRT
<213> ORGANISM: Nostoc punctiforme PCC 73102

<400> SEQUENCE: 84

```
Met Thr Ala Thr His His Leu Trp Leu Pro Ala Ser Thr Asp Leu Thr
1               5                   10                  15

Leu Leu Ser Asp Glu Ile His Val Trp Arg Ile Glu Leu Asp Gln Pro
            20                  25                  30

Glu Leu Gln Leu Gln Asn Leu Ala Ala Thr Leu Ser Ser Asp Glu Met
        35                  40                  45

Ala Arg Ala Glu Arg Phe Tyr Phe Gln Glu His Arg Gln Arg Phe Ile
    50                  55                  60

Ala Gly Arg Gly Ile Leu Arg Thr Ile Leu Gly Arg Tyr Leu Gly Ile
65                  70                  75                  80
```

Gln Pro Leu Gln Val Gln Phe Asn Tyr Gln Gln Arg Gly Lys Pro Val
                    85                  90                  95

Leu Ala Asp Thr Phe Ala Asp Ser Gly Leu Glu Phe Asn Leu Ser His
                100                 105                 110

Ser Gln Gly Met Gly Leu Cys Ala Val Asn Cys Thr His Pro Ile Gly
            115                 120                 125

Val Asp Leu Glu Tyr Ile Arg Ser Met Ser Asp Ile Glu Ala Leu Ala
    130                 135                 140

Lys Arg Phe Phe Leu Pro Arg Glu Tyr Glu Met Leu Arg Ser Leu Ser
145                 150                 155                 160

Pro Asn Gln Gln Gln Glu Val Phe Phe Arg Tyr Trp Thr Cys Lys Glu
                165                 170                 175

Ala Tyr Leu Lys Ala Thr Gly Asp Gly Leu Ser Gln Leu Glu Gln Val
            180                 185                 190

Glu Val Leu Leu Thr Pro Thr Glu Pro Ala Lys Leu Gln Ile Leu Glu
        195                 200                 205

Asp Trp Ser Leu Phe Glu Leu Val Pro Thr Asn Asn Tyr Val Ala Ala
    210                 215                 220

Val Ala Ile Ala Asn Tyr Gly Trp Asn Leu Lys Cys Trp Gln Tyr
225                 230                 235

<210> SEQ ID NO 85
<211> LENGTH: 122
<212> TYPE: DNA
<213> ORGANISM: Nostoc piscinale CENA21

<400> SEQUENCE: 85
ttggtattga tttagagtat atgcgctctg tgtcggattt ggaggcgctt gctcaaaggt      60 tcttttacc gagagaatat gagttagtgc atcgcttcc tcctcatcaa caacaagaag       120
ca                                                                    122

<210> SEQ ID NO 86
<211> LENGTH: 204
<212> TYPE: DNA
<213> ORGANISM: Nodularia harveyana UTEX B 2093

<400> SEQUENCE: 86
atttgtctca ttcccagggg ttagctctgt gtgcggtgaa ttatcacggt caaatcggca      60
taaatttaga gtgtattcgc cccatgtctg atgtggaagc cctggccaaa aggttttttt     120
taccgataaa atatgcttta atgcgatcgc tatctcctca ccaacagcaa gaaatatttt     180
ttcgttattg gacttgtaaa gagg                                            204

<210> SEQ ID NO 87
<211> LENGTH: 144
<212> TYPE: DNA
<213> ORGANISM: Nodularia spumigena BY1

<400> SEQUENCE: 87
atgaagaaga tagccgttgt ctgaaggatg tagaagcccg tgagaaaagg acgttgttac      60
tgcgagaata tgacgtagct gcgagcgcta tctgatcacc aacagcaaga aatatattac     120
aggtatggga cttgtaaaga ggca                                            144

<210> SEQ ID NO 88
<211> LENGTH: 205
<212> TYPE: DNA

<213> ORGANISM: Nodularia spumigena NSLA02A4

<400> SEQUENCE: 88

| | |
|---|---|
| cttgtctcat tcccagggt tagctctgtg tgcagtgaat tatcatcatc gaattgggat | 60 |
| agatttagaa tatattcgcg caatgtctga tgtggaatgc cttgccaaaa ggttcttttt | 120 |
| accgcgagaa tatgacgtag tgcgatcgct atctgatcac caacagcaag aaatatttt | 180 |
| ccgttattga cttgtgaaaa aggca | 205 |

<210> SEQ ID NO 89
<211> LENGTH: 205
<212> TYPE: DNA
<213> ORGANISM: Nodularia spumigena NSLA01

<400> SEQUENCE: 89

| | |
|---|---|
| cttgtctcat tcccagggt tagctctgtg tgcagtgaat tatcacaatc gaattgggat | 60 |
| agatttagaa tatattcgcc gaatgtctga tgtggaagcc cttgccaaaa ggttcttttt | 120 |
| accgcgagaa tatgacgtag tgcgatcgct atctgatcac caacagcaag aaatatttt | 180 |
| ccgttattgg acttgtaaag aggca | 205 |

<210> SEQ ID NO 90
<211> LENGTH: 212
<212> TYPE: DNA
<213> ORGANISM: Nodularia spumigena L575

<400> SEQUENCE: 90

| | |
|---|---|
| tttaacttgt ctcattccca ggggttagct ctgtgtgcag tgaattatca caatcgaatt | 60 |
| gggatagatt tagaatatat tcgccggatg tctgatgtag aagcccttgc caaaaggttc | 120 |
| tttttaccgc gagaatatga cgtagtgcga tcgctatctg atcaccaaca gcaagaaata | 180 |
| ttttttccgtt attggacgtt gtaaagaggc aa | 212 |

<210> SEQ ID NO 91
<211> LENGTH: 166
<212> TYPE: DNA
<213> ORGANISM: Nodularia spumigena NSBR01

<400> SEQUENCE: 91

| | |
|---|---|
| gaatttgaca accgtttggg atcatttaga atatattcgc cgaatgtctg atgtggaagc | 60 |
| ccttgccaaa aggttctttt taccgcgaga atatgacgta gtgcgatcgc tatctgatca | 120 |
| ccaacagcaa gaaatatttt tccgttattg acttgtaaa gaggca | 166 |

<210> SEQ ID NO 92
<211> LENGTH: 237
<212> TYPE: PRT
<213> ORGANISM: Nostoc sp. PCC 7120

<400> SEQUENCE: 92

Met Leu Gln His Thr Trp Leu Pro Lys Pro Pro Asn Leu Thr Leu Leu
1               5                   10                  15

Ser Asp Glu Val His Leu Trp Arg Ile Pro Leu Asp Gln Pro Glu Ser
            20                  25                  30

Gln Leu Gln Asp Leu Ala Ala Thr Leu Ser Ser Asp Leu Ala Arg
        35                  40                  45

Ala Asn Arg Phe Tyr Phe Pro Glu His Arg Arg Phe Thr Ala Gly
    50                  55                  60

Arg Gly Ile Leu Arg Ser Ile Leu Gly Gly Tyr Leu Gly Val Glu Pro

```
                    65                  70                  75                  80
Gly Gln Val Lys Phe Asp Tyr Glu Ser Arg Gly Lys Pro Ile Leu Gly
                85                  90                  95

Asp Arg Phe Ala Glu Ser Gly Leu Leu Phe Asn Leu Ser His Ser Gln
            100                 105                 110

Asn Leu Ala Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
            180                 185                 190

Ala Leu Thr Pro Thr Glu Pro Ala Lys Leu Gln Thr Ala Pro Ala Trp
        195                 200                 205

Ser Leu Leu Glu Leu Val Pro Asp Asp Asn Cys Val Ala Ala Val Ala
    210                 215                 220

Val Ala Gly Phe Gly Trp Gln Pro Lys Phe Trp His Tyr
225                 230                 235

<210> SEQ ID NO 93
<211> LENGTH: 237
<212> TYPE: PRT
<213> ORGANISM: Anabaena variabilis ATCC 29413

<400> SEQUENCE: 93

Met Leu Gln His Thr Trp Leu Pro Lys Pro Asn Leu Thr Leu Leu
1               5                   10                  15

Ser Asp Glu Val His Leu Trp Arg Ile Pro Leu Asp Arg Pro Glu Ser
            20                  25                  30

Gln Leu Gln His Leu Ala Ala Thr Leu Ser Ser Asp Glu Leu Ala Arg
        35                  40                  45

Ala Asn Arg Phe Tyr Phe Pro Glu His Arg Gln Arg Phe Thr Ala Gly
    50                  55                  60

Arg Gly Ile Leu Arg Ser Ile Leu Gly Leu Tyr Leu Gly Val Glu Pro
65                  70                  75                  80

Lys Gln Val Lys Phe Glu Tyr Glu Ser Arg Gly Lys Pro Val Leu Gly
                85                  90                  95

Asp Arg Phe Ala Asp Ser Gly Leu Leu Phe Asn Leu Ser His Ser Gln
            100                 105                 110

Asn Leu Gly Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
            180                 185                 190

Ala Leu Thr Pro Thr Glu Pro Ala Lys Leu Gln Thr Ala Pro Ala Trp
        195                 200                 205
```

```
Ser Leu Leu Glu Leu Val Pro Asp Asp Asn Cys Val Ala Ala Val Ala
    210                 215                 220

Val Ala Gly Phe Gly Trp Gln Pro Lys Phe Trp Gln Tyr
225                 230                 235

<210> SEQ ID NO 94
<211> LENGTH: 163
<212> TYPE: DNA
<213> ORGANISM: Cylindrospermum sp. CENA33
<220> FEATURE:
<221> NAME/KEY: misc_feature
<222> LOCATION: (93)..(93)
<223> OTHER INFORMATION: n is a, c, g, or t

<400> SEQUENCE: 94
tgggcgccaa attggggtag acctggagtg tattcgcccg gtgtctgatt tggaatccct    60
ggcagagcgg ttcttttttgc ctagagaatc tgntatggtg cgatcgcttc ccacaaatca   120
acaacaagaa gttttcttcc gttattggac atctaaagag gca                      163

<210> SEQ ID NO 95
<211> LENGTH: 141
<212> TYPE: DNA
<213> ORGANISM: Anabaena cylindrica PCC 7122

<400> SEQUENCE: 95
aattggggta gatttggaat atattcgccc tatgtcggat gtagaaagtc ttgctaaacg    60
cttcttttta ccaaaagaat atgacgtaat aaaattactc tctcccgaac aacaacaaca   120
ggtatttttt cgttactgga c                                              141

<210> SEQ ID NO 96
<211> LENGTH: 218
<212> TYPE: PRT
<213> ORGANISM: Prochlorococcus marinus subsp. pastoris str. CCMP1986

<400> SEQUENCE: 96

Met Thr Leu Leu Asn Asn Tyr Glu Tyr Lys Ile Pro Lys Ile Trp Phe
1               5                   10                  15

His Glu Ile Lys Gly Val Gln Asp Val Ala Thr Leu Asn Glu Leu Glu
            20                  25                  30

Ile Ala Asn Lys Leu Ser Arg His Arg Ala Asn Ile Phe Leu Glu Ser
        35                  40                  45

Arg Ala Tyr Ile Arg Gln Cys Leu Gly Asn Leu Phe Asn Leu Asn Pro
    50                  55                  60

Leu Glu Val Pro Ile Ile Ala Asn Pro Gly Glu Pro Pro Glu Leu Pro
65                  70                  75                  80

Lys Gly Met Gly Tyr Cys Ser Phe Ser His Cys Asn Asp Ala Ile Ile
                85                  90                  95

Leu Val Trp His Glu Arg Lys Ile Gly Ile Asp Ile Glu Arg Leu Asp
            100                 105                 110

Arg Asn Phe Asn Tyr Glu Lys Leu Ala Lys Lys Tyr Phe Phe Lys Ser
        115                 120                 125

Asn Ser Leu Asn Thr Thr Ser Glu Ser Tyr Arg Lys Thr Ile Leu Asn
    130                 135                 140

Gln Trp Cys Ala Val Glu Ala Ala Ile Lys Trp Asp His Gly Lys Leu
145                 150                 155                 160

Ala Glu Asp Ile Lys Glu Trp Gln Tyr Ser Glu Asn Asp Lys Ile Leu
                165                 170                 175
```

```
Phe His Asn Lys Lys Leu Lys Leu Lys Phe Thr Gln Ile Asn Leu
            180                 185                 190

Tyr Lys Trp Thr Ile Ser Leu Ala Tyr Lys Asp Thr Ser His Phe Ile
        195                 200                 205

Pro Asn Ile Ile Cys Ser Ser Lys Met Val
    210                 215

<210> SEQ ID NO 97
<211> LENGTH: 218
<212> TYPE: PRT
<213> ORGANISM: Prochlorococcus marinus subsp. marinus str. CCMP1375

<400> SEQUENCE: 97

Met Arg Leu Thr Asp Ile Gln Lys Pro Arg Val Leu Pro Leu Trp Ile
1               5                   10                  15

Phe Pro Met Asp Ser Pro Leu Lys Glu Ile Ser Ile Ser Glu Glu Lys
            20                  25                  30

Ile Ala Asn Ser Leu His Pro Arg Arg Ala Lys Glu Tyr Lys His Ala
        35                  40                  45

Arg Ser Tyr Val Arg Phe Ala Leu Ser Gln Phe Phe Lys Leu Asn Pro
    50                  55                  60

Leu Glu Ile Pro Leu Lys Ala Ser Ile Gly Lys Ala Pro Leu Leu Gly
65                  70                  75                  80

Asn Asn Leu Gly His Val Ser Phe Ser His Cys Asn Asp Ala Leu Leu
                85                  90                  95

Ile Gly Trp Ser Pro Thr Lys Leu Gly Val Asp Ile Glu Arg Ser Asp
            100                 105                 110

Arg Ala Leu Ser Ala Glu Gly Ile Ser Glu Arg Phe Phe His Lys Tyr
        115                 120                 125

Asp Gln Asn Asn Leu Lys Ser Leu Asn Asn Glu Asp Phe Arg Lys Lys
    130                 135                 140

Val Leu Glu Gln Trp Val Ile Lys Glu Ala Ala Ile Lys Trp Gln Arg
145                 150                 155                 160

Gly Thr Leu Ser Lys Asp Leu Lys Asn Trp His Ile Lys Asn Lys Ser
                165                 170                 175

Asn Val Ala Ile His Gln Thr Leu Asn His Glu Val Lys Ile Gln Thr
            180                 185                 190

Thr Ile Tyr Arg Ser Trp Ile Ile Ala Ile Ala Ser Asn Asp Asn Gln
        195                 200                 205

Gly Lys Gly Asp Leu Met Ile Cys Ala Asn
    210                 215

<210> SEQ ID NO 98
<211> LENGTH: 218
<212> TYPE: PRT
<213> ORGANISM: Synechococcus sp. WH 8102

<400> SEQUENCE: 98

Met Glu Pro Pro Leu Leu Gly Ser Arg Ser Val Thr Ala Leu Trp Leu
1               5                   10                  15

Ile Pro Glu His Gln Asp Leu Pro Ser Asp Val Glu Leu Ser Pro Val
            20                  25                  30

Glu Ala Gly Trp Met Asp Gly Met Ala Met Ser Arg Ala Val Ala Phe
        35                  40                  45

Arg Arg Ser Arg Leu Trp Met Arg Cys Leu Ala Asp Cys Phe Glu
    50                  55                  60
```

```
Val Asp Pro Ala Thr Val Pro Leu Gln Ala Pro Pro Gly Glu Pro Pro
 65                  70                  75                  80

Thr Leu Ala Asp Gly Trp Gly Cys Leu Ser Leu Ser His Cys Cys Asp
                 85                  90                  95

Ala Val Leu Val Ala Trp Ser Pro Asp Ala Val Gly Val Asp Leu Glu
            100                 105                 110

Arg Cys Asp Arg Cys Phe Pro Ala Ala Leu Ala Asp Arg Phe Tyr
        115                 120                 125

Cys Ala Glu Asp Arg Arg Glu Leu Asp Gly Leu Ala Gly Glu Thr Leu
130                 135                 140

Arg Met Ala Val Leu Lys Gln Trp Val Ala Lys Glu Ala Leu Ile Lys
145                 150                 155                 160

Met Gln Arg Gly Ser Leu Ala Leu Asp Leu Ser Arg Trp Arg Cys Gly
                165                 170                 175

Ala Asp Ala Cys Gln Gly Leu His Pro Asp Leu Glu His Pro Val Pro
            180                 185                 190

Val His Arg Leu Gln Leu Glu Gly Trp Leu Met Ala Val Ala Gly Ala
        195                 200                 205

Ala Gly Gln Val Gly Pro Ile Cys Leu Ala
    210                 215

<210> SEQ ID NO 99
<211> LENGTH: 217
<212> TYPE: PRT
<213> ORGANISM: Prochlorococcus marinus str. MIT 9313

<400> SEQUENCE: 99

Met Pro Leu Pro Leu Asn Ser Arg Ser Val Leu Ala Leu Trp Leu Phe
  1               5                  10                  15

Pro Met Gln Ala Pro Leu Met Pro Ile Ser Pro Glu Glu Glu Gln Trp
                 20                  25                  30

Ala Gly Arg Leu Ser Ala Arg Arg Ser Arg Gln Phe Arg Gln Ser Arg
             35                  40                  45

Gly Tyr Val Arg Asp Ala Leu Ala Asp Leu Trp Gln Val Ser Ala Leu
 50                  55                  60

Glu Ile Pro Leu Gln Ala Pro Pro Gly Lys Pro Pro Glu Leu Ala Asn
 65                  70                  75                  80

Gly Trp Gly Tyr Ile Ser Phe Ser His Cys Gln Asp Ala Leu Leu Val
                 85                  90                  95

Gly Trp Ser Pro Gln Arg Val Gly Val Asp Leu Glu Arg Ser Asp Arg
            100                 105                 110

Pro Ile Ala Ala Glu Leu Leu Ala Arg Arg Tyr Phe Cys Ala Asp Asp
        115                 120                 125

Gln Ser Ala Leu Cys His Leu Arg Gly Ala Ala Leu Arg Asp Ala Val
130                 135                 140

Leu Glu Gln Trp Leu Ser Lys Glu Ala Ala Ile Lys Trp Gln Arg Gly
145                 150                 155                 160

Ser Leu Ala Ala Asp Leu Ile His Trp Arg Cys Gly Val Asp Ser Val
                165                 170                 175

Phe Ala Val His Glu Val Leu Gly His Gln Val Asp Val His Arg Ile
            180                 185                 190

His His Asn Leu Trp Ser Met Ala Val Val Ser Asp Phe Ser Ala Met
        195                 200                 205

Ser Asn Ala Pro Met Leu Cys Leu Val
    210                 215
```

<210> SEQ ID NO 100
<211> LENGTH: 1625
<212> TYPE: PRT
<213> ORGANISM: Gloeobacter violaceus PCC 7421

<400> SEQUENCE: 100

```
Met Pro Met Asn Pro Ile Glu Pro Val Ala Ile Val Gly Met Ala Ala
1               5                   10                  15

Leu Phe Pro Lys Ala Ala Thr Val Gly Asp Phe Trp Gln Asn Ile Val
            20                  25                  30

Asp Lys Val Asp Ala Val Ser Glu Ala Pro Ala Ser Trp Ala Arg His
        35                  40                  45

Tyr Phe Asp Pro Asn Ser Lys Glu Gln Asp Arg Ile Tyr Thr Ser Lys
    50                  55                  60

Gly Gly Phe Leu Gly Glu Leu Ala Glu Phe Asp Pro Thr Glu Phe Gly
65                  70                  75                  80

Ile Met Pro Asn Thr Leu Asp Ala Ala Glu Pro Asp His Phe Ile Ala
                85                  90                  95

Leu Lys Leu Ala Arg Asp Ala Leu Ala Asp Ala Gly Tyr Leu Asp Arg
            100                 105                 110

Pro Phe Asn Arg Lys Lys Ala Gly Ile Ile Leu Gly His Gly Val Tyr
        115                 120                 125

Val Asn Arg Gly His Met Ala Met Leu Gln Gln Thr Leu Val Leu Asp
    130                 135                 140

Gln Thr Met Asp Thr Leu Arg Arg Val Cys Pro Glu Leu Gly Glu Glu
145                 150                 155                 160

Ala Leu Ala Ala Val His Arg Ala Leu Arg Lys Ser Ala Pro Ala Phe
                165                 170                 175

Asn Ala Glu Val Val Pro Gly Met Val Pro Asn Val Ile Thr Gly Arg
            180                 185                 190

Ile Ala Asn Arg Leu Asp Leu Met Gly Pro Asn Tyr Leu Val Asp Ala
        195                 200                 205

Ala Cys Ala Ser Gly Leu Ile Val Val Glu Leu Ala Met Lys Glu Leu
    210                 215                 220

Ala Ser Gly Arg Cys Asp Leu Val Leu Ala Gly Gly Val Gln Ala Ser
225                 230                 235                 240

Leu Pro Pro Gln Tyr Asn Met Ala Phe Cys Gln Leu Gly Ala Leu Ser
                245                 250                 255

Arg Thr Asn Ile Arg Pro Phe Asp Arg Ala Ala Asp Gly Asn Val Met
            260                 265                 270

Gly Glu Gly Cys Gly Ile Leu Val Leu Lys Arg Leu Ala Asp Ala Glu
        275                 280                 285

Leu Asp Gly Asp Arg Ile Tyr Ala Val Val Arg Gly Val Gly Ser Ser
    290                 295                 300

Ser Asn Gly Lys Ala Leu Gly Met Leu Ala Pro Arg Leu Glu Gly Glu
305                 310                 315                 320

Val Leu Ala Leu Glu Glu Ala Tyr Ser Leu Thr Gly Ile Asp Pro Ala
                325                 330                 335

Ser Val Asp Leu Val Glu Ala His Gly Thr Gly Ile Pro Val Gly Asp
            340                 345                 350

Arg Thr Glu Met Glu Ala Leu Ala Gln Val Tyr Gly Ala Arg Glu Gly
        355                 360                 365

Asp Leu Pro Arg Val Gly Met Gly Ser Val Lys Ser Met Ile Gly His
```

-continued

```
            370                 375                 380
Cys Ile Pro Ala Ser Gly Ala Ala Ser Phe Ile Lys Met Ala Leu Ala
385                 390                 395                 400

Leu Tyr His Lys Val Leu Pro Pro Thr Leu Leu Asp Ala Val Asn Pro
                405                 410                 415

Glu Leu Gly Val Glu Lys Thr Pro Phe Tyr Leu Asn Asn Ala Thr Arg
                420                 425                 430

Pro Trp Val Ser Ala Asn Gln Arg Pro Arg Ala Gly Ile Asn Ala
                435                 440                 445

Phe Gly Phe Gly Gly Ile Asn Ala His Ala Ile Leu Glu Glu His Thr
450                 455                 460

Pro Thr Gly Pro Asp Thr Val Leu His Arg Arg Trp Pro Ser Glu Leu
465                 470                 475                 480

Val Val Phe Ala Ala Asp Asp Arg Pro Gly Leu Ile Ala Lys Ile Glu
                485                 490                 495

Arg Thr Leu Val Val His Pro Thr Leu Pro Leu Ala Gln Ile Ala Cys
                500                 505                 510

Asn Gln Ala Ala Gly Thr Ala Gly Asp Tyr Arg Leu Ala Val Val Ala
                515                 520                 525

Lys Asp Arg Ala Asp Leu His Lys Lys Leu Arg Gln Ala Val Glu Lys
530                 535                 540

Leu Lys Glu Pro Gly Arg Val Arg Leu Arg Gly Gly Val Met Tyr Gly
545                 550                 555                 560

Glu Val Thr Ser Glu Met Ala Asp Ala Gln Thr Ala Met Ile Phe Pro
                565                 570                 575

Gly Glu Gly Cys Gln Tyr Pro Asn Met Leu Ala Asp Leu Cys Leu His
                580                 585                 590

Phe Pro Val Val Arg Glu Trp Phe Asp Phe Leu Asp Ser Ala Leu Gly
                595                 600                 605

Ala Asp Arg Pro His Pro Pro Ser Arg Tyr Ile Phe Pro Pro Thr
610                 615                 620

Ala Ile Asp Glu Gln Val Gln Glu Gln Thr His Arg Ala Ile Tyr Gln
625                 630                 635                 640

Met Glu Leu Ala Val Ala Ser Val Ala Thr Ala Ser Met Ala Leu Tyr
                645                 650                 655

Glu Leu Leu Gln Gln Phe Glu Ile Lys Ala Asp Val Met Val Gly His
                660                 665                 670

Ser Thr Gly Glu Leu Thr Ser Leu Val Ala Ser Gly Val Val Arg Leu
                675                 680                 685

Thr Asp Arg Ser Gln Met Met Glu Lys Leu Leu Leu Asn Gly Leu
690                 695                 700

Tyr Gln Arg Leu Glu Gln Met Asn Ile Val Pro Arg Gly Ala Leu Leu
705                 710                 715                 720

Ala Val Gly Ala Val Lys Ser Asp Asp Leu Gln Gln Val Leu Ala Asp
                725                 730                 735

Leu Glu Gly Arg Leu His Leu Ala Met Asp Asn Cys Pro Asn Gln Val
                740                 745                 750

Val Leu Phe Gly Asp Glu Gln Ala Val Thr Gln Ala Ser Glu Arg Leu
                755                 760                 765

Gln Ala Ser Gly Ala Ile Cys Ser Arg Leu Pro Phe Asp Arg Ala Tyr
                770                 775                 780

His Thr Pro Leu Phe Glu Glu Ala Gly Lys Val Leu Arg Gly Phe Tyr
785                 790                 795                 800
```

-continued

```
Asp Ala Leu Asp Val Gly Pro Gly His Thr Pro Leu Phe Ser Cys Ala
                805                 810                 815
Ser Val Gly Leu Phe Pro Asp Pro Glu Gly Ile Arg Thr Leu Gly
            820                 825                 830
Glu Arg Gln Trp Pro Ser Arg Val Arg Phe Arg Glu Thr Leu Glu Thr
                835                 840                 845
Leu Tyr Ser Gln Gly Val Arg His Phe Val Glu Val Gly Pro Ser Gly
                850                 855                 860
Asn Leu Thr Gly Phe Val Asp Asp Val Leu Lys Gly Arg Asp Tyr Lys
865                 870                 875                 880
Ala Val Pro Val Asn Ser Gln Arg Lys Ser Gly Leu Glu Gln Leu Gln
                885                 890                 895
His Leu Val Gly Gln Leu Phe Val Ser Gly Lys His Val Ser Phe Ala
                900                 905                 910
Pro Phe Tyr Ser Arg Arg Gly Leu Leu Pro Gln Pro Pro Ala Pro Gly
                915                 920                 925
Glu Ala Gln Pro Lys Arg Arg Gly Arg Val Leu Asp Leu Thr Leu Pro
                930                 935                 940
His Met Glu Leu Pro Pro Asp Phe Val Leu Pro Glu Arg Gln Ala Pro
945                 950                 955                 960
Ala Val Pro Val Pro Ala Pro Lys Ala Thr Thr Asn Gly Ser His Pro
                965                 970                 975
Pro Ser Leu Thr Ser Leu Thr Ala Ala Pro Ala Pro Val Ser Thr Leu
                980                 985                 990
Ala Pro Ser Gln Glu Pro Pro Val Ala Ala Leu Ala Thr Leu Glu Arg
                995                 1000                1005
Ser Val Pro Ile Ala Glu Asp Pro Pro Asn Val Pro Ala Pro Ile
    1010                1015                1020
Gln Ala Pro Ala Asn Gly His Asp Leu Gly Ala Ala Ala Val Ile
    1025                1030                1035
Val Asp His Phe Ala Leu Met Gln Glu Phe Leu Ala Ser Gln Asp
    1040                1045                1050
Arg Met Leu Ser Ala Leu Leu Thr Gly Ala Pro Ala Gln Thr Ala
    1055                1060                1065
Glu Met Ala Val Ser Val Asp Pro Trp Pro Leu Leu Gly Gln Val
    1070                1075                1080
Ile His Leu Asp Val Gln Ser Leu Val Cys Arg Arg Arg Phe Thr
    1085                1090                1095
Ile Gly Glu Asp Ile Phe Leu Arg Asp His Thr Leu Gly Gly Asn
    1100                1105                1110
Pro Ser Ser Leu Gln Pro Ala Leu Leu Pro Leu Pro Ile Leu Pro
    1115                1120                1125
Phe Thr Thr Ser Met Glu Leu Leu Ala Glu Ala Ala Val Tyr Leu
    1130                1135                1140
Ala Gly Gly Asn Gly Val Val Thr Ala Met Ser Glu Val Arg Gly
    1145                1150                1155
Phe Arg Trp Leu Ala Leu Asp Arg Gly Val Leu Thr Val Glu Ala
    1160                1165                1170
Val Leu Arg Arg Leu Pro Asp Gly Arg Tyr Gln Ala Gln Leu Phe
    1175                1180                1185
Gln Leu Ser Asp Glu Asp Ala Ser Val Arg Leu Pro Ala Phe Glu
    1190                1195                1200
```

```
Ala Val Ile Ala Val Ala Ala Ala Tyr Thr Ser Ser Pro Ala Pro
1205                1210                1215

Arg Asp Leu Asp Pro Gly Ala Leu Trp Pro Leu Ser Ala Glu Leu
1220                1225                1230

Ala Asp Asp Arg Leu Tyr Ser Thr Gly Met Phe His Gly Pro Arg
1235                1240                1245

Phe Gln Ser Leu Lys His Ile His Cys Cys Gly Glu Arg Gly Ile
1250                1255                1260

Gln Ala Asp Leu Gly Val Trp Gly Thr Gly Asp Phe Phe Ala Asp
1265                1270                1275

Gly Arg Pro Gly Val Phe Gln Leu Glu Gln Ser Leu Ile Asp Ala
1280                1285                1290

Ala Gly Gln Leu Ala Ala Phe Trp Leu Ser Gln Asp Ile Asp Ser
1295                1300                1305

Pro Asp Phe Ser Met Phe Pro Phe Gln Val Arg Ser Phe Glu Gln
1310                1315                1320

Phe Gly Ala Ser Pro Pro Ala Gly Thr Arg Leu Leu Cys Arg Cys
1325                1330                1335

Thr Ser Arg Tyr Leu Ser Glu Asn Ala Thr Glu Ser His Leu Asp
1340                1345                1350

Tyr Ile Asp Gly Glu Gly Arg Val Leu Tyr Arg Leu Thr Gly Trp
1355                1360                1365

Gln Ser Arg Phe Phe Leu Ser Pro Pro Arg Tyr Gln Asp Phe Arg
1370                1375                1380

Val Ala Pro Gln Val Asn Tyr Leu Ser Glu Pro Trp Met Gln Ala
1385                1390                1395

Glu Thr Gly Leu Phe Val Arg Arg Tyr Glu Asn Pro Asp Asp Tyr
1400                1405                1410

Leu Glu Glu Ser Trp Glu Ile Trp Lys Arg Val Thr Ala His Leu
1415                1420                1425

Ile Leu Asn Glu Ala Glu Arg Thr Tyr Trp Tyr Ala Leu Pro Glu
1430                1435                1440

Gln Gly Pro Arg Arg Arg Asp Trp Leu Leu Gly Arg Leu Ala Ala
1445                1450                1455

Lys Glu Ala Leu Arg Gln Trp Thr Glu Ala Ala Tyr Gly Leu Gln
1460                1465                1470

Leu Ala Pro Ala Asp Phe Glu Ile Leu Ser Asn Glu Leu Gly Lys
1475                1480                1485

Pro Met Val Ser Cys Pro Ala Leu Ala Ala Phe Gly Pro Leu Pro
1490                1495                1500

Glu Ile Ser Ile Ala His Ser Glu Gly His Ala Val Ala Ala Val
1505                1510                1515

Ala Tyr Gly Met Ala Leu Gly Ile Asp Leu Gln Arg Leu Glu Arg
1520                1525                1530

Leu Gly Ser Thr Asp Trp Leu Thr Ala Ala Phe Asp Pro Ser Glu
1535                1540                1545

Leu Ala Leu Val Ser Ser Pro Thr Glu Leu Ala Leu Ile Gly Leu
1550                1555                1560

Trp Ser Ala Lys Glu Ala Ala Lys Ala Phe Gly Thr Gly Leu
1565                1570                1575

Glu Gly Glu Pro Arg Arg Trp Gln Val Val Ala Arg Asn Pro Glu
1580                1585                1590
```

```
Gly Thr Glu Met Thr Val Val His Gly Glu His Arg Phe Ser Val
    1595                1600                1605

Arg Leu Trp Tyr Ala Pro Asp Glu Val Phe Ala Val Cys Gly Trp
    1610                1615                1620

Gln Pro
    1625

<210> SEQ ID NO 101
<211> LENGTH: 300
<212> TYPE: PRT
<213> ORGANISM: Nostoc punctiforme PCC 73102

<400> SEQUENCE: 101

Met Pro Pro Ser Thr His Leu Pro Glu Phe Ala Gln Cys Leu Pro
1               5                   10                  15

Thr Ile Ala Ala Met His Ile Asp Ile Gly Gly Glu Leu Ala Val His
                20                  25                  30

Ala Lys Asp Tyr Leu Ser Ala Lys Glu Leu Ala Tyr Phe His Gln Phe
                35                  40                  45

Lys His Pro Arg Arg Arg Tyr Glu Trp Phe Thr Ala Arg Leu Val Cys
    50                  55                  60

Lys Leu Leu Phe Ser Arg Tyr Leu Ser Asn Thr His Leu Ala Asn Ser
65              70                  75                  80

Asn Ser Val Trp Pro Pro Thr Ile Gln Lys Leu Gly Cys Asn Asp Ile
                85                  90                  95

Ala Thr Val Leu Pro Ile Val Tyr Arg Ser Ile Glu Ile Leu Pro Ser
                100                 105                 110

Asn Pro Ser Leu Lys Gly Ala Pro Gln Leu Phe Trp Gln Gly Asn Ile
                115                 120                 125

Leu Ser Ala Met Tyr Leu Ser Ile Ser His Ala Gly Gly Leu Ala Ile
    130                 135                 140

Ala Ser Leu Ser Ser Ser Gly Pro Val Gly Leu Asp Leu Glu Glu Pro
145                 150                 155                 160

Ile Ser His Cys Pro Asn Phe Tyr Glu Ser Tyr Phe Ser Lys Gln Glu
                165                 170                 175

Thr Leu Trp Val Gln Gln Gln Ile Lys Asp Glu Leu Ser Ile Ser Gln
                180                 185                 190

Leu Tyr Thr Leu Leu Trp Thr Leu Lys Glu Ser Tyr Leu Lys Thr Gly
    195                 200                 205

Ile Ser Pro Ile Asn Asn Ile Cys Asp Phe Ala Asn Leu Glu Ile Lys
    210                 215                 220

Ile Asp Thr Ser Leu Phe Thr Val Ser Lys His Leu Pro Lys Ile Gly
225                 230                 235                 240

Phe Asn Ser Gln Leu His Ile Leu Lys Leu Gln Phe Ser Tyr Ala Lys
                245                 250                 255

Ser Thr Phe Ala Pro Tyr Ala Ala Phe Ser Ile Met Ala Asn Leu Ile
                260                 265                 270

Leu Ser Ile Val Ala Phe Glu Leu Asn Thr His Leu Glu Asn Val Leu
                275                 280                 285

Lys Val Leu Arg Glu Asp Asn Ser Leu Leu His Lys
                290                 295                 300

<210> SEQ ID NO 102
<211> LENGTH: 195
<212> TYPE: PRT
```

<213> ORGANISM: Thermosynechococcus elongatus BP-1

<400> SEQUENCE: 102

```
Met Trp Asp Cys Pro Leu Pro Pro Ile Val Pro Gln Trp Arg Ala
 1               5                  10                  15

Pro His Pro Asn Leu Thr Leu Asp Ser Ser Ala Leu His Leu Trp Trp
                 20                  25                  30

Leu Thr Leu Pro Pro Asp Val Pro Arg Gly Val Ile Leu Arg Ala Tyr
             35                  40                  45

Leu Arg Arg Tyr Gln Pro Asn Leu Gly Glu Arg Pro Leu Pro Arg Ala
         50                  55                  60

Ala Gly Gly Lys Pro Tyr Leu Asn Gly Leu Glu Phe Asn Trp Ser His
 65                  70                  75                  80

Ser Gly Asn Leu Ala Val Leu Ala Val Ser Gly Arg Ala Ala Val Gly
                 85                  90                  95

Val Asp Val Glu Ile Leu Arg Leu Cys Pro Gln Arg Ala Ala Ile Ser
            100                 105                 110

Arg Arg Phe Phe Gly Ala Ala Leu Gln Gln Arg Ile Leu Glu Gly Gly
        115                 120                 125

Asp Arg Ser Phe Leu Gln Ala Trp Thr Tyr Tyr Glu Ala Trp Leu Lys
130                 135                 140

Ala Gln Gly Ile Gly Val Trp Gln Arg Thr Ala Ala Gln Ser Leu Glu
145                 150                 155                 160

His Trp Val Ala Ser Phe Pro Val Gly Asp Arg Ala Ile Ala Ser Val
                165                 170                 175

Val Val Leu Thr Pro Thr Pro Pro Gln Cys Phe Phe Pro Arg Pro Glu
            180                 185                 190

Ala Met Ala
        195
```

<210> SEQ ID NO 103
<211> LENGTH: 259
<212> TYPE: PRT
<213> ORGANISM: Synechococcus elongatus PCC 7942

<400> SEQUENCE: 103

```
Met Gln Arg Pro Asn Pro Ser Asp Ala Val Pro Val Pro Ser Ile Pro
 1               5                  10                  15

Ser Cys Asp Arg Gly Pro Ile Pro Asn Pro Val Thr Trp Arg Thr Ser
                 20                  25                  30

Pro Glu Pro Leu Phe Leu Ser Ala Gln Thr Val His Leu Trp Arg Cys
             35                  40                  45

Ser Leu Thr Arg Ser Leu Ser Ser Ala Glu Gln Ala Ile Val Ala Ala
         50                  55                  60

Asp Cys Asp Arg Ala Gln Ala Tyr Gly Ser Asn Arg Arg His Gln Phe
 65                  70                  75                  80

Leu Cys Gly Arg Trp Trp Leu Arg Gln Leu Ser Leu Tyr Leu Pro
                 85                  90                  95

Glu Glu Pro Ala Asp Phe Arg Phe Gln Leu Ser Pro Thr Gly Lys Pro
            100                 105                 110

Glu Leu Pro Gln Ser Asn Leu Cys Phe Asn Leu Ser His Ser Gly Ser
        115                 120                 125

Thr Leu Leu Ile Ala Ile Ala Trp Gln Pro Val Gly Val Asp Val Glu
130                 135                 140

Gln Pro Arg Ser Arg Ser Trp Leu Ala Leu Ala Arg Arg Tyr Phe Pro
```

-continued

```
              145                 150                 155                 160
         Ser Ala Glu Leu Ala Ala Met Gln Gln Ser Thr Asp Cys Asp Arg Trp
                         165                 170                 175
         Gly Leu Ala Ser Trp Val Cys Lys Glu Ala Trp Ile Lys Ala Gln Gly
                         180                 185                 190
         Arg Thr Leu Ala Asn Ser Leu Arg His Leu Gln Cys Ala Trp Thr Ala
                         195                 200                 205
         Asn Gly Gln Pro Arg Leu Ser Gly Leu Gly Ser Glu Glu Ser Gln Val
                         210                 215                 220
         Gln Leu Leu Gln Val Asp Pro Gln Gln Leu Trp Ala Ala Ile Ala
         225                 230                 235                 240
         Met Pro Ala Gly Trp Asn Tyr Gln Thr Trp Thr Ala Ala Ile Ile Arg
                         245                 250                 255
         Lys Asn His

<210> SEQ ID NO 104
<211> LENGTH: 242
<212> TYPE: PRT
<213> ORGANISM: Chlorobium tepidum TLS

<400> SEQUENCE: 104

Met Met Ile Ile Ser Lys Glu Ala Val Thr Leu Ile His Thr Asp Thr
1               5                   10                  15
His Ile Ala Gly Ile Pro Glu Glu Lys Leu Phe Glu Thr Leu Thr Asp
                20                  25                  30
Glu Glu Lys Glu Lys Ala Asp Arg Phe Arg Phe Asp Asn Asp Arg His
                35                  40                  45
Asn Phe Leu Leu Arg Arg Gly Leu Leu Arg Leu Leu Leu Gly Glu Thr
    50                  55                  60
Leu Ser Ile Glu Pro Ser Leu Ile Arg Phe Ser Ser Thr Gln Val Gly
65                  70                  75                  80
Lys Pro Phe Met Thr Phe Pro Glu Asn Thr Gly Leu Tyr Phe Asn Leu
                85                  90                  95
Ser His Ser Gly Arg Gln Ile Val Tyr Ala Phe Ser Lys His Pro Glu
                100                 105                 110
Met Gly Val Asp Ile Glu Arg Ile Arg Thr Val Asp Asp Ile Asp Leu
                115                 120                 125
Leu Ala Arg Lys Tyr Phe Ser Ala Glu Glu Tyr Ala Ile Ile Val Asn
                130                 135                 140
Leu Pro Ser Arg Glu Lys Asn Lys Ala Phe Ile Arg Ile Trp Ser Ile
145                 150                 155                 160
Lys Glu Ala Leu Ile Lys Ala Ser Gly Trp Pro Leu Glu His Gly Leu
                165                 170                 175
Ala Ala Phe Asp Val Ala Thr Gln Tyr Arg Met Thr Arg Phe Lys Met
                180                 185                 190
Pro Phe Gly Ala Asn Arg Ser Leu Thr Cys Ile Thr Pro Val Phe Asp
                195                 200                 205
Tyr Met Cys Gly Phe Ala Thr Ala Leu Ala Ile Gln Leu Asp Asn Asn
                210                 215                 220
Glu Pro Leu Asn Leu Arg Arg Tyr Ser Leu Gln Asn Gly Glu Tyr Ile
225                 230                 235                 240
Glu Leu
```